(12) United States Patent
Augustine

(10) Patent No.: US 12,097,152 B2
(45) Date of Patent: Sep. 24, 2024

(54) PATIENT SECUREMENT SYSTEM FOR THE SURGICAL TRENDELENBURG POSITION

(71) Applicant: Augustine Biomedical and Design, LLC, Eden Prairie, MN (US)

(72) Inventor: Scott D. Augustine, Deephaven, MN (US)

(73) Assignee: Augustine Biomedical and Design, LLC, Eden Prairie, MN (US)

( * ) Notice: Subject to any disclaimer, the term of this patent is extended or adjusted under 35 U.S.C. 154(b) by 0 days.

(21) Appl. No.: 18/496,580

(22) Filed: Oct. 27, 2023

(65) Prior Publication Data

US 2024/0050300 A1     Feb. 15, 2024

Related U.S. Application Data

(63) Continuation of application No. 18/165,576, filed on Feb. 7, 2023, now Pat. No. 11,801,188, which is a
(Continued)

(51) Int. Cl.
*A61G 13/04*     (2006.01)
*A61G 13/12*     (2006.01)
(Continued)

(52) U.S. Cl.
CPC ......... *A61G 13/126* (2013.01); *A61G 13/04* (2013.01); *A61G 13/122* (2013.01);
(Continued)

(58) Field of Classification Search
CPC .... A61G 13/126; A61G 13/04; A61G 13/122; A61G 13/1235; A61G 7/005;
(Continued)

(56) References Cited

U.S. PATENT DOCUMENTS 2,140,213 A    12/1938   Tegarty
2,403,676 A     7/1946   Modlinski
(Continued)

FOREIGN PATENT DOCUMENTS

CA    3019306 A1    10/2017
DE    3343664 C1     3/1985
(Continued)

OTHER PUBLICATIONS

Moritz and Henriques, "Studies of Thermal Injury: The Relative Importance of Time and Surface Temperature in the Causation of Cutaneous Burns," Am. J. Pathology, vol. 23, 1947, pp. 695-720.
(Continued)

*Primary Examiner* — Fredrick C Conley
(74) *Attorney, Agent, or Firm* — Fredrikson & Byron, P.A.

(57) ABSTRACT

A patient securing overlay is provided that includes a sheet of fabric for supporting a patient's torso on a surgical table. The sheet of fabric has an upper surface configured to face the patient and a lower surface configured to face a surgical table mattress or underbody support. The sheet of fabric includes friction enhancing elements applied to at least a portion of the upper surface thereof. The sheet of fabric can include an extension at a foot end of the sheet of fabric that provides material to be tucked under a foot end of the surgical table mattress or underbody support for securing the foot end of the sheet of fabric to the surgical table mattress or underbody support. The extension can include one or more friction enhancing elements.

23 Claims, 37 Drawing Sheets

Related U.S. Application Data continuation of application No. 17/857,589, filed on Jul. 5, 2022, now Pat. No. 11,576,833, which is a continuation of application No. 17/564,540, filed on Dec. 29, 2021, now Pat. No. 11,382,817, which is a continuation of application No. 17/233,528, filed on Apr. 18, 2021, now Pat. No. 11,278,463, which is a continuation of application No. 16/941,823, filed on Jul. 29, 2020, now Pat. No. 10,993,866, which is a continuation of application No. 16/780,136, filed on Feb. 3, 2020, now Pat. No. 10,765,580.

(60) Provisional application No. 62/824,911, filed on Mar. 27, 2019.

(51) Int. Cl.
  B32B 3/30 (2006.01)
  B32B 5/24 (2006.01)
  B32B 7/12 (2006.01)
  A61G 7/005 (2006.01)
  A61G 13/10 (2006.01)

(52) U.S. Cl.
  CPC ............ A61G 13/1235 (2013.01); B32B 3/30 (2013.01); B32B 5/245 (2013.01); B32B 7/12 (2013.01); A61G 7/005 (2013.01); A61G 13/101 (2013.01); A61G 2200/32 (2013.01); B32B 2266/0235 (2013.01); B32B 2266/0278 (2013.01); B32B 2305/022 (2013.01); B32B 2307/744 (2013.01); B32B 2535/00 (2013.01)

(58) Field of Classification Search
  CPC .... A61G 13/101; A61G 2200/32; B32B 3/30; B32B 5/245; B32B 7/12; B32B 2266/0235; B32B 2266/0278; B32B 2305/022; B32B 2307/744; B32B 2535/00
  See application file for complete search history.

(56) References Cited

U.S. PATENT DOCUMENTS

| | | | |
|---|---|---|---|
| 2,497,186 A | 2/1950 | Pedersen | |
| 2,635,175 A | 4/1953 | Wilson | |
| 2,706,768 A | 4/1955 | Julius | |
| 2,715,674 A | 8/1955 | Abbott et al. | |
| 2,873,352 A | 2/1959 | Franco | |
| 2,948,802 A | 8/1960 | Shaw | |
| 2,982,976 A | 5/1961 | Ferolito | |
| 3,008,152 A | 11/1961 | Seidenberg | |
| 3,134,891 A | 5/1964 | Marina | |
| 3,137,871 A | 6/1964 | Florio | |
| 3,340,549 A | 9/1967 | Gerd | |
| 3,380,087 A | 4/1968 | Petty et al. | |
| 3,423,574 A | 1/1969 | Shomphe et al. | |
| 3,548,147 A | 12/1970 | Owers | |
| 3,582,456 A | 6/1971 | Stolki | |
| 3,634,655 A | 1/1972 | Jordan | |
| 3,690,325 A | 9/1972 | Kenny | |
| 3,780,262 A | 12/1973 | Rudd | |
| 3,808,403 A | 4/1974 | Gunma et al. | |
| 3,839,621 A | 10/1974 | Hariu | |
| 3,854,156 A | 12/1974 | Williams | |
| 3,874,504 A | 4/1975 | Verakas | |
| 3,900,654 A | 8/1975 | Stinger | |
| 3,936,661 A | 2/1976 | Furuishi et al. | |
| 4,061,898 A | 12/1977 | Murray et al. | |
| 4,118,531 A | 10/1978 | Hauser | |
| 4,149,066 A | 4/1979 | Niibe | |
| 4,186,294 A | 1/1980 | Bender | |
| 4,250,398 A | 2/1981 | De Fonsoet et al. | |
| 4,270,040 A | 5/1981 | Mcmullan et al. | |
| 4,358,668 A | 11/1982 | Mcmullan et al. | |
| 4,363,947 A | 12/1982 | Bergersen | |
| 4,423,308 A | 12/1983 | Callaway et al. | |
| 4,479,795 A | 10/1984 | Mustacich et al. | |
| 4,495,402 A | 1/1985 | Burdick et al. | |
| 4,534,886 A | 8/1985 | Kraus et al. | |
| 4,536,433 A * | 8/1985 | Sagi | B32B 27/32 5/924 |
| 4,582,564 A | 4/1986 | Shanefield et al. | |
| 4,626,664 A | 12/1986 | Grise | |
| 4,658,119 A | 4/1987 | Endo et al. | |
| 4,660,388 A | 4/1987 | Greene, Jr. | |
| 4,661,689 A | 4/1987 | Harrison | |
| 4,676,247 A | 6/1987 | Van Cleve | |
| 4,682,447 A | 7/1987 | Osborn | |
| 4,691,762 A | 9/1987 | Elkins et al. | |
| 4,719,335 A | 1/1988 | Batliwalla et al. | |
| 4,747,409 A | 5/1988 | Silen | |
| 4,764,665 A | 8/1988 | Orban et al. | |
| 4,798,936 A | 1/1989 | Johnson, Sr. | |
| 4,899,749 A | 2/1990 | Laroco | |
| 4,912,306 A | 3/1990 | Grise et al. | |
| 4,930,317 A | 6/1990 | Klein | |
| 4,941,961 A | 7/1990 | Noguchi et al. | |
| 4,989,283 A | 2/1991 | Krouskop | |
| 4,991,242 A | 2/1991 | Brown | |
| 5,008,515 A | 4/1991 | Mccormack | |
| 5,010,233 A | 4/1991 | Henschen et al. | |
| 5,023,433 A | 6/1991 | Gordon | |
| 5,032,705 A | 7/1991 | Batcheller et al. | |
| 5,072,598 A | 12/1991 | Dibrell | |
| 5,074,285 A | 12/1991 | Wright | |
| 5,086,629 A | 2/1992 | Dibrell | |
| 5,148,002 A | 9/1992 | Kuo et al. | |
| 5,179,743 A | 1/1993 | Lanman | |
| 5,255,390 A | 10/1993 | Gross et al. | |
| 5,320,164 A | 6/1994 | Szczesuil et al. | |
| 5,352,870 A | 10/1994 | Daugherty et al. | |
| 5,380,580 A | 1/1995 | Rogers et al. | |
| 5,383,918 A | 1/1995 | Panetta | |
| 5,395,399 A | 3/1995 | Rosenwald | |
| 5,422,462 A | 6/1995 | Kishimoto | |
| 5,443,056 A | 8/1995 | Smith et al. | |
| 5,473,783 A | 12/1995 | Allen | |
| 5,496,358 A | 3/1996 | Rosenwald | |
| 5,534,021 A | 7/1996 | Dvoretzky | |
| 5,605,144 A | 2/1997 | Simmons | |
| 5,638,438 A | 6/1997 | Keen | |
| 5,704,081 A | 1/1998 | Bollinger | |
| 5,723,845 A | 3/1998 | Partington et al. | |
| 5,755,275 A | 5/1998 | Rose et al. | |
| 5,773,275 A | 6/1998 | Anderson et al. | |
| 5,815,864 A | 10/1998 | Sloop | |
| 5,817,145 A | 10/1998 | Augustine et al. | |
| 5,824,996 A | 10/1998 | Kochman et al. | |
| 5,835,983 A | 11/1998 | Mcmahen et al. | |
| 5,878,620 A | 3/1999 | Gilbert et al. | |
| 5,881,410 A | 3/1999 | Yamada | |
| 5,895,973 A | 4/1999 | Fessenden | |
| 5,928,274 A | 7/1999 | Augustine | |
| 5,932,129 A | 8/1999 | Hyatt | |
| 5,948,303 A | 9/1999 | Larson | |
| 5,964,792 A | 10/1999 | Augustine | |
| 5,966,763 A | 10/1999 | Thomas et al. | |
| 5,970,542 A | 10/1999 | Mays | |
| 5,974,605 A | 11/1999 | Dickerhoff et al. | |
| 5,986,243 A | 11/1999 | Campf | |
| 6,030,412 A | 2/2000 | Klatz et al. | |
| 6,038,722 A | 3/2000 | Giori et al. | |
| 6,053,910 A | 4/2000 | Fleenor | |
| 6,054,331 A | 4/2000 | Woo et al. | |
| 6,078,026 A | 6/2000 | West | |
| 6,084,217 A | 7/2000 | Bulgajewski | |
| 6,093,910 A | 7/2000 | Mcclintock et al. | |
| 6,147,333 A | 11/2000 | Mattson | |
| 6,149,674 A | 11/2000 | Borders | |
| 6,172,344 B1 | 1/2001 | Gordon et al. | |
| 6,180,929 B1 | 1/2001 | Pearce | |
| 6,184,496 B1 | 2/2001 | Pearce | |

(56) References Cited

U.S. PATENT DOCUMENTS

| | | |
|---|---|---|
| 6,189,487 B1 | 2/2001 | Owen et al. |
| 6,210,427 B1 | 4/2001 | Augustine et al. |
| 6,214,000 B1 | 4/2001 | Fleenor et al. |
| 6,215,111 B1 | 4/2001 | Rock et al. |
| 6,229,123 B1 | 5/2001 | Kochman et al. |
| 6,229,126 B1 | 5/2001 | Ulrich et al. |
| 6,235,049 B1 | 5/2001 | Nazerian |
| 6,240,623 B1 | 6/2001 | Johansson |
| 6,292,957 B1 | 9/2001 | Thompson |
| 6,348,678 B1 | 2/2002 | Loyd et al. |
| 6,373,034 B1 | 4/2002 | Rock et al. |
| 6,403,935 B2 | 6/2002 | Kochman et al. |
| 6,416,534 B1 | 7/2002 | Montagnino et al. |
| 6,434,328 B2 | 8/2002 | Rutherford |
| 6,452,138 B1 | 9/2002 | Kochman et al. |
| 6,452,139 B1 | 9/2002 | Benoit et al. |
| 6,483,087 B2 | 11/2002 | Gardner et al. |
| 6,493,889 B2 | 12/2002 | Kocurek |
| 6,544,258 B2 | 4/2003 | Fleenor et al. |
| 6,565,593 B2 | 5/2003 | Diana |
| 6,578,219 B1 * | 6/2003 | Gabel ............... A61G 7/05738 5/601 |
| 6,582,456 B1 | 6/2003 | Hand et al. |
| 6,705,388 B1 | 3/2004 | Sorgo |
| 6,713,733 B2 | 3/2004 | Kochman et al. |
| 6,723,115 B1 | 4/2004 | Daly |
| 6,728,978 B1 | 5/2004 | Nordin |
| 6,730,115 B1 | 5/2004 | Heaton |
| 6,755,852 B2 | 6/2004 | Lachenbruch et al. |
| 6,770,848 B2 | 8/2004 | Haas et al. |
| 6,770,854 B1 | 8/2004 | Keane |
| 6,839,922 B1 | 1/2005 | Foggett et al. |
| 6,872,758 B2 | 3/2005 | Simpson et al. |
| 6,924,467 B2 | 8/2005 | Ellis et al. |
| 6,933,469 B2 | 8/2005 | Ellis et al. |
| 6,961,969 B2 * | 11/2005 | Nichols ............... A63B 21/4037 5/420 |
| 6,967,309 B2 | 11/2005 | Wyatt et al. |
| 6,974,935 B2 | 12/2005 | O'Grady |
| 7,013,509 B2 | 3/2006 | Hickman |
| 7,020,912 B2 | 4/2006 | Berge |
| 7,022,950 B2 | 4/2006 | Haas et al. |
| 7,049,559 B2 | 5/2006 | Ishii et al. |
| 7,053,344 B1 | 5/2006 | Surjan et al. |
| 7,107,629 B2 | 9/2006 | Miros et al. |
| 7,161,120 B1 | 1/2007 | Stroud et al. |
| 7,176,419 B2 | 2/2007 | Ellis et al. |
| 7,181,790 B2 | 2/2007 | Wirtz |
| 7,183,524 B2 | 2/2007 | Naylor et al. |
| 7,228,578 B2 | 6/2007 | Linnane |
| 7,268,320 B2 | 9/2007 | Rock et al. |
| 7,282,676 B1 | 10/2007 | Bouchier et al. |
| 7,287,289 B1 * | 10/2007 | Hagopian ............... A61G 13/08 5/691 |
| 7,375,308 B2 | 5/2008 | Ferguson |
| 7,543,344 B2 | 6/2009 | Augustine et al. |
| 7,714,255 B2 | 5/2010 | Augustine et al. |
| 7,851,729 B2 | 12/2010 | Augustine et al. |
| 8,062,343 B2 | 11/2011 | Augustine et al. |
| 8,065,763 B2 | 11/2011 | Brykalski et al. |
| 8,084,722 B2 | 12/2011 | Haas et al. |
| 8,170,685 B2 | 5/2012 | Docherty et al. |
| 8,283,602 B2 | 10/2012 | Augustine et al. |
| 8,288,693 B2 | 10/2012 | Weiss et al. |
| 8,291,612 B2 | 10/2012 | Ferguson |
| 8,418,297 B2 | 4/2013 | Mikkelsen et al. |
| 8,464,720 B1 | 6/2013 | Pigazzi et al. |
| 8,511,314 B2 | 8/2013 | Pigazzi et al. |
| 8,604,391 B2 | 12/2013 | Augustine et al. |
| 8,624,164 B2 | 1/2014 | Deibel et al. |
| 8,698,044 B2 | 4/2014 | Burr et al. |
| 8,772,676 B2 | 7/2014 | Augustine et al. |
| 8,876,812 B2 | 11/2014 | Aramayo |
| 9,161,876 B2 | 10/2015 | Pigazzi et al. |
| 9,375,343 B2 | 6/2016 | Marshall et al. |
| 9,750,656 B1 | 9/2017 | Pigazzi et al. |
| 9,782,287 B2 | 10/2017 | Pigazzi et al. |
| 9,931,262 B2 | 4/2018 | Pigazzi et al. |
| 9,945,080 B2 | 4/2018 | Caterina et al. |
| 9,949,883 B1 | 4/2018 | Pigazzi et al. |
| 9,962,122 B2 | 5/2018 | Augustine et al. |
| 10,045,902 B2 | 8/2018 | Pigazzi et al. |
| 10,201,935 B2 | 2/2019 | Augustine et al. |
| 10,206,248 B2 | 2/2019 | Augustine et al. |
| 10,413,469 B2 | 9/2019 | Chua |
| 10,765,580 B1 | 9/2020 | Augustine |
| 10,959,675 B2 | 3/2021 | Augustine et al. |
| 10,980,694 B2 | 4/2021 | Augustine |
| 10,993,866 B2 | 5/2021 | Augustine |
| 11,026,856 B1 | 6/2021 | Bergad |
| 11,103,188 B2 | 8/2021 | Augustine et al. |
| 11,278,463 B2 | 3/2022 | Augustine |
| 2001/0020303 A1 | 9/2001 | Endo et al. |
| 2001/0040014 A1 | 11/2001 | Green et al. |
| 2001/0044971 A1 | 11/2001 | Borders et al. |
| 2002/0005398 A1 | 1/2002 | Gillner et al. |
| 2002/0018877 A1 | 2/2002 | Woodall et al. |
| 2002/0047007 A1 | 4/2002 | Loyd, Sr. et al. |
| 2002/0073489 A1 | 6/2002 | Totton et al. |
| 2002/0117495 A1 | 8/2002 | Kochman et al. |
| 2002/0124312 A1 | 9/2002 | Yoon |
| 2003/0023292 A1 | 1/2003 | Gammons et al. |
| 2003/0069621 A1 | 4/2003 | Kushnir |
| 2003/0091889 A1 | 5/2003 | Sotomura et al. |
| 2003/0192121 A1 | 10/2003 | Fleming et al. |
| 2003/0195596 A1 | 10/2003 | Augustine et al. |
| 2003/0208848 A1 | 11/2003 | Flick et al. |
| 2004/0149711 A1 | 8/2004 | Wyatt et al. |
| 2004/0164499 A1 | 8/2004 | Murakami et al. |
| 2004/0174056 A1 | 9/2004 | Gryp et al. |
| 2004/0193237 A1 | 9/2004 | Krueger |
| 2004/0237206 A1 | 12/2004 | Webster et al. |
| 2005/0016982 A1 | 1/2005 | Campf et al. |
| 2005/0016993 A1 | 1/2005 | Koskey |
| 2005/0051537 A1 | 3/2005 | Lewis |
| 2005/0061122 A1 | 3/2005 | Behringer |
| 2005/0061681 A1 | 3/2005 | Lim et al. |
| 2005/0103353 A1 | 5/2005 | Grahn et al. |
| 2005/0150763 A1 | 7/2005 | Butters et al. |
| 2006/0085919 A1 | 4/2006 | Kramer et al. |
| 2006/0120054 A1 | 6/2006 | Buschke |
| 2006/0142828 A1 | 6/2006 | Schorr et al. |
| 2006/0191675 A1 | 8/2006 | Fletcher et al. |
| 2006/0210766 A1 | 9/2006 | Press et al. |
| 2006/0247745 A1 | 11/2006 | Thompson |
| 2006/0260060 A1 | 11/2006 | Apperson et al. |
| 2006/0261055 A1 | 11/2006 | Child et al. |
| 2007/0012675 A1 | 1/2007 | Devroy |
| 2007/0023053 A1 | 2/2007 | Bowen et al. |
| 2007/0049997 A1 | 3/2007 | Fields et al. |
| 2007/0056096 A1 | 3/2007 | Assink |
| 2007/0068916 A1 | 3/2007 | Augustine et al. |
| 2007/0068928 A1 | 3/2007 | Augustine et al. |
| 2007/0068929 A1 | 3/2007 | Augustine et al. |
| 2007/0068930 A1 | 3/2007 | Augustine et al. |
| 2007/0068931 A1 | 3/2007 | Augustine et al. |
| 2007/0068932 A1 | 3/2007 | Hewes et al. |
| 2007/0080155 A1 | 4/2007 | Augustine et al. |
| 2007/0093883 A1 | 4/2007 | Anderson et al. |
| 2007/0101996 A1 | 5/2007 | Carstens |
| 2007/0106353 A1 | 5/2007 | Carstens |
| 2007/0106355 A1 | 5/2007 | Carstens |
| 2007/0108190 A1 | 5/2007 | Ferguson |
| 2007/0142891 A1 | 6/2007 | Stanley |
| 2007/0152479 A1 | 7/2007 | Howman et al. |
| 2007/0164010 A1 | 7/2007 | Rock et al. |
| 2007/0243452 A1 | 10/2007 | Weidman et al. |
| 2007/0272673 A1 | 11/2007 | Keane |
| 2007/0284356 A1 | 12/2007 | Findlay |
| 2008/0021530 A1 | 1/2008 | Castellani et al. |
| 2008/0083721 A1 | 4/2008 | Kaiserman et al. |
| 2008/0127414 A1 | 6/2008 | Allen |
| 2008/0173629 A1 | 7/2008 | Deibel et al. |
| 2008/0203080 A1 | 8/2008 | Fung |

(56) References Cited

U.S. PATENT DOCUMENTS

| | | |
|---|---|---|
| 2008/0217587 A1 | 9/2008 | Gaudiana et al. |
| 2008/0249521 A1 | 10/2008 | Dunning et al. |
| 2008/0249524 A1 | 10/2008 | Dunning |
| 2008/0255641 A1 | 10/2008 | Ellis |
| 2008/0281310 A1 | 11/2008 | Dunning et al. |
| 2008/0281311 A1 | 11/2008 | Dunning et al. |
| 2008/0283513 A1 | 11/2008 | Ferguson et al. |
| 2009/0036884 A1 | 2/2009 | Gregg et al. |
| 2009/0078690 A1 | 3/2009 | Lee et al. |
| 2009/0095735 A1 | 4/2009 | Resheff |
| 2009/0099630 A1 | 4/2009 | Augustine et al. |
| 2009/0099631 A1 | 4/2009 | Augustine et al. |
| 2009/0163984 A1 | 6/2009 | Robinson et al. |
| 2009/0198230 A1 | 8/2009 | Behnke et al. |
| 2009/0222996 A1 | 9/2009 | Balonick et al. |
| 2010/0078807 A1 | 4/2010 | Schulz |
| 2010/0089896 A1 | 4/2010 | Bar |
| 2010/0119704 A1 | 5/2010 | Hemmelgarn et al. |
| 2010/0161016 A1 | 6/2010 | Augustine et al. |
| 2010/0168825 A1 | 7/2010 | Barbknecht |
| 2010/0183814 A1 | 7/2010 | Rios et al. |
| 2010/0200558 A1 | 8/2010 | Liu et al. |
| 2010/0204763 A1 | 8/2010 | Augustine et al. |
| 2010/0213189 A1 | 8/2010 | Keite-Telgenbuescher et al. |
| 2010/0222457 A1 | 9/2010 | Wallner |
| 2010/0224612 A1 | 9/2010 | Asami et al. |
| 2010/0275377 A1 | 11/2010 | West |
| 2010/0279086 A1 | 11/2010 | Park et al. |
| 2010/0283295 A1 | 11/2010 | Smith et al. |
| 2010/0325796 A1 | 12/2010 | Lachenbruch et al. |
| 2011/0031230 A1 | 2/2011 | Kim |
| 2011/0047706 A1 | 3/2011 | Hiebert |
| 2011/0092930 A1 | 4/2011 | Poorman |
| 2011/0099900 A1 | 5/2011 | Weder |
| 2011/0226751 A1 | 9/2011 | Lazanja et al. |
| 2011/0233185 A1 | 9/2011 | Augustine et al. |
| 2012/0065716 A1 | 3/2012 | Gill et al. |
| 2012/0111846 A1 | 5/2012 | Hammerschmidt |
| 2012/0140375 A1 | 6/2012 | Kim et al. |
| 2012/0222192 A1 | 9/2012 | Carey et al. |
| 2012/0238842 A1 | 9/2012 | Colvin, Jr. et al. |
| 2012/0238901 A1 | 9/2012 | Augustine |
| 2012/0255124 A1 | 10/2012 | West |
| 2012/0273475 A1 | 11/2012 | An |
| 2012/0279953 A1 | 11/2012 | Augustine et al. |
| 2013/0036551 A1 | 2/2013 | Mcgann |
| 2013/0327339 A1* | 12/2013 | Chua ............... A61G 13/04 128/845 |
| 2014/0074086 A1 | 3/2014 | Macintyre-Ellis et al. |
| 2014/0263265 A1 | 9/2014 | Augustine et al. |
| 2014/0312027 A1 | 10/2014 | Augustine et al. |
| 2014/0316494 A1 | 10/2014 | Augustine et al. |
| 2014/0316495 A1 | 10/2014 | Augustine et al. |
| 2015/0047120 A1 | 2/2015 | Partridge et al. |
| 2015/0143628 A1 | 5/2015 | Fowler et al. |
| 2015/0148874 A1 | 5/2015 | Augustine et al. |
| 2015/0216610 A1 | 8/2015 | Augustine |
| 2015/0257953 A1 | 9/2015 | Trabucco |
| 2015/0289817 A1 | 10/2015 | Augustine et al. |
| 2015/0290027 A1 | 10/2015 | Augustine et al. |
| 2015/0290062 A1 | 10/2015 | Augustine et al. |
| 2015/0290065 A1 | 10/2015 | Augustine et al. |
| 2015/0297435 A1 | 10/2015 | Visco |
| 2015/0327332 A1 | 11/2015 | Augustine et al. |
| 2015/0366367 A1 | 12/2015 | Augustine et al. |
| 2015/0373781 A1 | 12/2015 | Augustine et al. |
| 2016/0143091 A1 | 5/2016 | Augustine et al. |
| 2016/0279007 A1 | 9/2016 | Flatt |
| 2018/0140493 A1 | 5/2018 | Shandas et al. |
| 2019/0091085 A1 | 3/2019 | Emerson et al. |
| 2019/0091086 A1 | 3/2019 | Emerson et al. |
| 2019/0099288 A1 | 4/2019 | Vergara et al. |
| 2019/0262169 A1 | 8/2019 | Vergara et al. |

FOREIGN PATENT DOCUMENTS

| | | | |
|---|---|---|---|
| DE | 10065592 | A1 | 7/2002 |
| DE | 102004011128 | A1 | 9/2005 |
| EP | 787476 | A2 | 8/1997 |
| EP | 1374822 | A1 | 1/2004 |
| EP | 2662063 | A1 | 11/2013 |
| EP | 3207912 | A2 | 8/2017 |
| GB | 586745 | A | 3/1947 |
| GB | 969253 | A | 9/1964 |
| JP | 2001248060 | A | 9/2001 |
| JP | 2018157923 | A | 10/2018 |
| WO | 9923992 | A1 | 5/1999 |
| WO | 9925155 | A1 | 5/1999 |
| WO | 0135878 | A2 | 5/2001 |
| WO | 0195841 | A2 | 12/2001 |
| WO | 0232661 | A2 | 4/2002 |
| WO | 2004093758 | A1 | 11/2004 |
| WO | 2007041389 | A1 | 4/2007 |
| WO | 2008089412 | A1 | 7/2008 |
| WO | 2010107724 | A1 | 9/2010 |
| WO | 2012125916 | A2 | 9/2012 |
| WO | 2013134477 | A1 | 9/2013 |
| WO | 2015157674 | A2 | 10/2015 |
| WO | 2015157684 | A1 | 10/2015 |
| WO | 2017184949 | A1 | 10/2017 |

OTHER PUBLICATIONS

Stoll & Greene, "Relationship Between Pain and Tissue Damage Due to Thermal Radiation," J. Applied Physiology, vol. 14, No. 3, 1959, pp. 373-383.

Lenhardt et al., "Local warming and insertion of peripheral venous cannulas: single blinded prospective randomised controlled trial and single blinded randomised crossover trial," British Medical Journal 325:409, Aug. 2002, 4 pages.

Bair Hugger brochure, retrieved from http://www.bairhugger.com/arizanthealthcare/pdf/600755A.pdf, 2003, 6 pages.

Eeon TexTM Conductive Textiles, Product Details, www.eeonyx.com/prodte.html, Sep. 19, 2006, pp. 1-5.

International Patent Application No. PCT/US2015/060659, International Search Report and Written Opinion mailed Feb. 5, 2016, 12 pages.

International Search Report and the Written Opinion of the International Searching Authority, or the Declaration for International Pat. App. No. PCT/US2015/025374, Nov. 9, 2015, 5 pages, European Patent Office, Rijswijk, The Netherlands.

International Search Report and the Written Opinion of the International Searching Authority, or the Declaration for International Pat. App. No. PCT/US2015/025392, Jul. 16, 2015, 13 pages, European Patent Office, Rijswijk, The Netherlands.

Invitation to Pay Additional Fees and, Where Applicable, Protest Fee for International Pat. App. No. PCT/US2015/025374, Jul. 20, 2015, 5 pages, European Patent Office, Rijswijk, The Netherlands.

Supplementary European Search Report for EP Pat. App. No. 12757173, May 22, 2015, 9 pages, European Patent Office, Munich, Germany.

HDPatientWarming "WaffleGrip(TM) Trendelenburg Positioning System", Jul. 9, 2018, pp. 1-6, Retrieved from the Internet: URL:https://www.youtube.com/watch?v=tP0X2T711Hk&feature=youtu.be [retrieved on May 28, 2020].

International Patent Application No. PCT/US2020/023021, International Search Report and Written Opinion mailed Jun. 9, 2020, 17 pages.

U.S. Appl. No. 90/014,744, Decision Granting Ex Parte Reexamination dated Jun. 9, 2021, 14 pages.

* cited by examiner

PATIENT SECUREMENT SYSTEM FOR THE SURGICAL TRENDELENBURG POSITION

CROSS-REFERENCE TO RELATED APPLICATIONS

This application is a continuation of U.S. application Ser. No. 18/165,576, filed Feb. 7, 2023, which is a continuation of U.S. application Ser. No. 17/857,589, filed Jul. 5, 2022 and which issued as U.S. Pat. No. 11,576,833 on Feb. 14, 2023, which is a continuation of U.S. application Ser. No. 17/564,540, filed Dec. 29, 2021 and which issued as U.S. Pat. No. 11,382,817 on Jul. 12, 2022, which is a continuation of U.S. application Ser. No. 17/233,528, filed Apr. 18, 2021 and which issued as U.S. Pat. No. 11,278,463 on Mar. 22, 2022, which is a continuation of U.S. application Ser. No. 16/941,823, filed Jul. 29, 2020 and which issued as U.S. Pat. No. 10,993,866 on May 4, 2021, which is a continuation of U.S. application Ser. No. 16/780,136, filed Feb. 3, 2020 and which issued as U.S. Pat. No. 10,765,580 on Sep. 8, 2020, which claims priority to U.S. Provisional Patent Application No. 62/824,911, filed Mar. 27, 2019, the entire contents of each of which are incorporated herein by reference.

BACKGROUND OF THE INVENTION

Keeping the patient from sliding off of a surgical table when the table is tilted into a steep, head-down (Trendelenburg) position, is a constant challenge for surgical personnel and a danger for the patient. This problem has gotten worse in recent years with the advent of laparoscopic surgery and particularly with the advent of robotic surgery. In both of these instances, the patients are regularly placed into the steep Trendelenburg position so that gravity can move the internal organs out of the way of the laparoscopes. Depending on the angle or steepness of the head-down Trendelenburg positioning, the patient's weight, and the make-up of the support surface (e.g., bed sheets), patients can be at risk of sliding off of the head end of the surgical table in the Trendelenburg position. This is especially true for pelvic surgery (e.g. rectal, gynecological, and urological), where the head of the surgical table may be tilted as much as 45° downward in order to use gravity to move the bowels and other internal organs away from the pelvis to improve the view of the surgical site.

Many types of patient securement devices have been tried over the years. In general, there are several categories of securement devices, including: straps and tape; shoulder bolsters; foam surgical table overlays; bean bags that mold around the patient; and gel pads that stick to the patient. Straps and tape across the chest have proven to not be secure. Straps over the shoulders have resulted in stretch injuries to the nerves of the brachial plexus. Similarly, bolsters of foam or bean bags at the patient's shoulders that are secured to the side rails of the bed have also resulted in stretch injuries to the nerves of the brachial plexus and are not recommended by the Association for Operating Room Nurses. Gel pads are cold and messy because everything sticks to them.

Foam surgical table overlays have become the standard securement devices. The foam is generally sized to cover the section of the surgical table that supports the patient's torso and head. Irrespective of the foam's coefficient of friction against the patient's skin, the smooth surface of the surgical mattress usually creates a lower coefficient of friction between the foam and the mattress than the coefficient of friction between the foam and the patient. Therefore, unwanted slipping is most likely to occur between the mattress and the foam surgical table overlay. In order to improve the connection between the mattress and the foam surgical table overlay, the foam overlay is typically taped or strapped to the side rails of the surgical table. However, tape sticking to a foam surgical table overlay or straps glued to a foam surgical table overlay as described in U.S. Pat. No. 8,464,720, for example, have a significant risk of becoming unattached when the weight of a 400 pound patient is applied at a 45° head-down angle. Either the adhesive fails or the top layer of foam pulls away from the foam surgical table overlay while still being adhered to the tape.

Some known devices, as described in U.S. Pat. No. 10,045,902 for example, advocate for the use of thicker foam pads, such as viscoelastic pads having a thickness in the range of from three-fourths of an inch to three inches or greater to permit formation of a depression having a depth sufficient to assist in holding a patient on the pad. In the present disclosure, we refer to the formation of a depression having a depth sufficient to assist in holding a patient on the pad as a "bolster effect." The disadvantage of any securement device relying wholly or in part on a bolster effect is that bolster-type securement can be overpowered by excessive weight and rounded shaped shoulders that are common with obesity. Therefore, securement devices that rely in part on a bolster effect must provide instructions for use that limit both the weight of the patient and the angle of decline.

Patients in the Trendelenburg position, especially for robotic surgery, conventionally have their arms tucked along the sides of their bodies. Certain conventional arm protection and securing devices are cumbersome, bulky, expensive, and prevent heating of the arms. Known methods of tucking the arms at the patient's sides with or without an arm protection device rely on wrapping the arms in a draw sheet and tucking the ends of the draw sheet under the patient. The tucked ends of the draw sheet can easily become un-tucked, simply pulling out from under the patient and allowing the arm to fall toward the floor, which may cause nerve injuries.

Robotic surgeries can usually take longer to perform than open surgeries and thus the patients frequently get more hypothermic in the cold operating rooms. With the patient's arm tucked at their sides, the only skin surface area available for conventional forced-air warming, is the top of the shoulders and the head and thus forced-air warming is ineffective. As a result, most patients operated in either the Trendelenburg position or the supine position with their arms tucked and warmed with forced-air warming, become very hypothermic. The same increased risk of hypothermia is experienced by other patients positioned with their arms tucked but not in the Trendelenburg (head down) position.

It would be desirable to provide reliable, safe, and convenient patient securement devices to stabilize the patient on the surgical table for the Trendelenburg and other unusual positions. It would also be desirable to provide improved patient warming devices for use during surgery in the Trendelenburg position. In addition, it would be desirable to provide better arm protection and securing devices for use during surgery in the Trendelenburg position. Still further, it would be desirable to provide better patient warming devices, better arm protection, and better arm securing devices for use during surgery in the flat supine position with the patient's arms tucked.

SUMMARY OF THE INVENTION

The underbody support mattresses and blankets of this disclosure are intended for use in medical settings generally.

These include the operating room, the emergency room, the intensive care unit, hospital rooms, nursing homes, and other medical treatment locations.

Various embodiments include flexible and conformable heated underbody supports including mattresses, mattress overlays, and pads for providing therapeutic warming to a person, such as to a patient in an operating room setting. In various embodiments, the heated underbody support is maximally flexible and conformable allowing the heated surface to deform and accommodate the person without reducing the accommodation ability of any underlying mattress, for example.

In some embodiments, a sheet of fabric or other material that has been at least partially coated on both sides with friction-enhancing elements, such as high-friction plastic or rubber, may be interposed between the patient and the underbody support in order to increase the coefficient of friction therebetween. An example of such friction-enhancing elements may be a PVC foam or silicone rubber applied as a pattern of three-dimensional raised dots onto a sheet of fabric.

In some embodiments, heated blankets may be positioned along the side edges of the underbody support and held in place by attaching them to a base film layer that crosses the surgical mattress from side to side. In some embodiments, heated blankets may be attached to the side edges of the underbody support. The heated blankets may be wrapped around the patient's arms to provide additional heating as well as support, securement, and protection of the arms and hands.

Certain embodiments provide a patient securing overlay with securement to a surgical table mattress or underbody support for use during surgery in the Trendelenburg position. The patient securing overlay includes a sheet of fabric configured to support a patient's torso on a surgical table. The sheet of fabric has an upper surface configured to face the patient and a lower surface configured to face the surgical table mattress or underbody support. The sheet of fabric includes friction enhancing elements applied to at least a portion of the upper surface. The sheet of fabric includes an extension at a foot end of the sheet of fabric that provides material to be tucked under a foot end of the surgical table mattress or underbody support for securing the foot end of the sheet of fabric to the surgical table mattress or underbody support. The extension at the foot end of the sheet of fabric includes one or more friction enhancing elements that improve the friction bond between the sheet of fabric and either an underside of the surgical table mattress or underbody support. The extension at the foot end of the sheet of fabric is narrower than the sheet of fabric and anchors against a perineal cutout in the surgical table mattress or the underbody support such that the extension stretches to create a force vector that is directly opposite a force vector associated with the patient sliding down an incline of the surgical table when the surgical table is in the Trendelenburg position.

Certain other embodiments provide a patient securing overlay with securement to an unheated underbody support for use during surgery in the Trendelenburg position. The patient securing overlay includes an unheated underbody support that is secured to side rails of a surgical table, and a sheet of fabric that is configured to support a patient's torso on the surgical table. The sheet of fabric has an upper surface configured to face the patient and a lower surface configured to face the unheated underbody support. The sheet of fabric includes friction enhancing elements applied to at least a portion of the upper surface thereof. The sheet of fabric also includes an extension at the foot end of the sheet of fabric that provides material to be tucked under a foot end of the unheated underbody support for securing the foot end of the sheet of fabric to the unheated underbody support. The extension at the foot end includes an anchor that comprises a planar sheet of material that comprises plastic, metal, or fiberboard. The anchor is removably insertable between a bottom of the unheated underbody support and a top of the surgical table mattress at the foot end of the unheated underbody support. The extension of the sheet of fabric at the foot end anchors against the foot end of the unheated underbody support such that the extension stretches to create a force vector that is directly opposite the force vector associated with the patient sliding down an incline of the surgical table when the surgical table is in the Trendelenburg position.

Certain other embodiments provide a patient securing overlay with adjustable securement to a surgical table mattress for use during surgery in the Trendelenburg position. The patient securing overlay includes a sheet of fabric configured to support a patient's torso on a surgical table. The sheet of fabric has an upper surface configured to face the patient and a lower surface configured to face the surgical table mattress. The sheet of fabric includes friction enhancing elements applied to at least a portion of its upper surface. The sheet of fabric includes an extension at the foot end of the sheet of fabric that provides material to be tucked under a foot end of the surgical table mattress for securing the foot end of the sheet of fabric to the surgical table mattress. The extension at the foot end of the sheet of fabric is narrower than the sheet of fabric and includes an anchor that comprises a planar sheet of material that comprises plastic, metal, or fiberboard. The anchor is removably insertable between a bottom of the surgical table mattress and a top of the surgical table at the foot end of a section of the surgical table mattress that is configured to support the patient's torso. The extension of the sheet of fabric at the foot end of the sheet of fabric anchors against a perineal cutout in the surgical table mattress such that the extension stretches to create a force vector that is directly opposite a force vector associated with the patient sliding down an incline of the surgical table when the surgical table is in the Trendelenburg position.

DETAILED DESCRIPTION OF PREFERRED EMBODIMENTS

The following detailed description is exemplary in nature and is not intended to limit the scope, applicability, or configuration of the invention in any way. Rather, the following description provides practical illustrations for implementing various exemplary embodiments. Examples of constructions, materials, dimensions, and manufacturing processes are provided for selected elements, and all other elements employ that which is known to those of skill in the field. Those skilled in the art will recognize that many of the examples provided have suitable alternatives that can be utilized.

Figure 1:
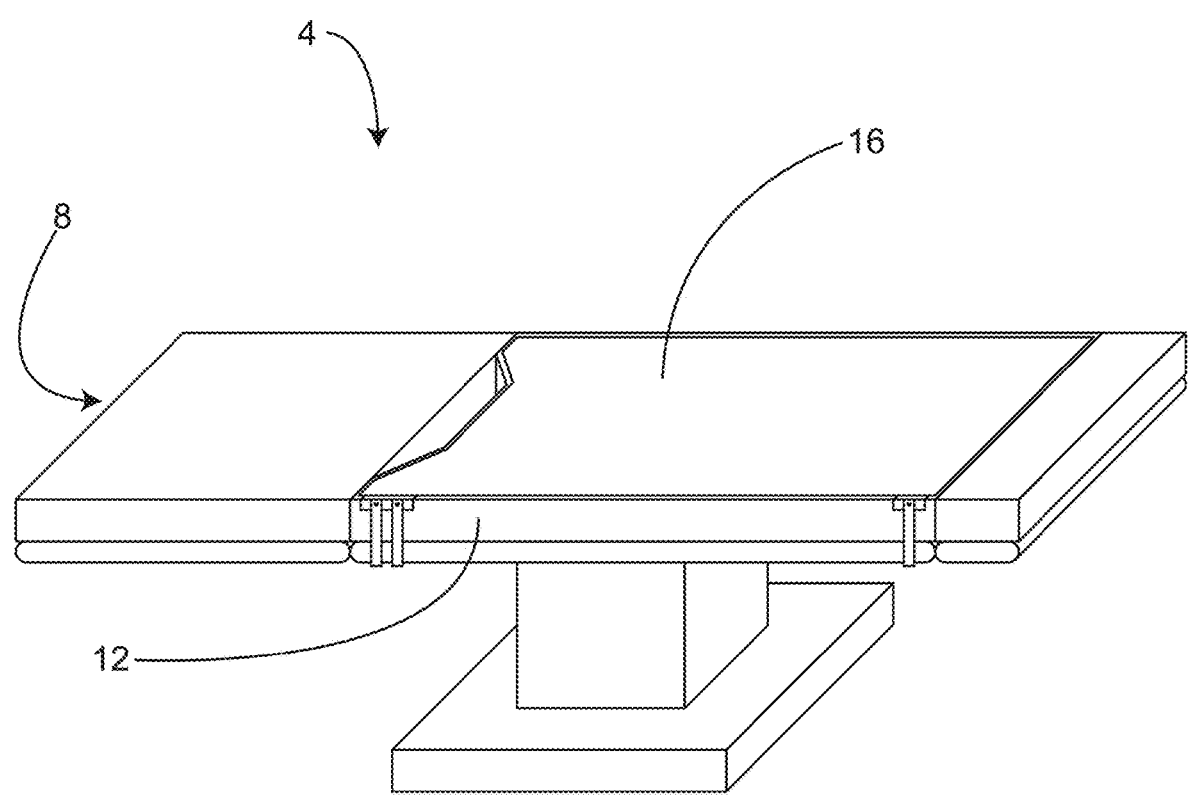
FIG. 1 is a perspective view of an underbody support attached to a surgical table in accordance with illustrative embodiments.

In some embodiments, as shown in FIG. 1, embodiments include underbody supports such as heated underbody supports, including heated mattresses, heated mattress overlays, and heated pads. The term underbody support may be considered to encompass any surface situated below and supporting a user in a generally recumbent position, such as a patient who may be undergoing surgery, including heated mattresses, heated mattress overlays and heated pads.

Heated mattress overlay embodiments may be identical to heated pad embodiments, with the only difference being whether or not they are used on top of a mattress. Furthermore, the difference between heated pad embodiments and heated mattress embodiments may be the amount of support and accommodation they provide, and some pads may be insufficiently supportive to be used alone like a mattress. As such, the various aspects which are described herein apply to mattresses, mattress overlay and pad embodiments, even if only one type of support is shown in the specific example.

While there is repeated reference to "heated underbody supports" in this disclosure, skilled artisans will appreciate that the heat feature is not a necessary component of every embodiment. Non-heated underbody support embodiments are also anticipated.

In some embodiments, the heated underbody support includes a heater assembly and a layer of compressible material. The heater assembly may include a heating element including a sheet of conductive fabric having a top surface, a bottom surface, a first edge, an opposing second edge, a length, and a width. The conductive fabric may include threads separately and individually coated with an electrically conductive or semi-conductive material, with the coated threads of the fabric being able to slide relative to each other such that the sheet is flexible and stretchable. In some embodiments, the conductive fabric may be made with threads that are conductive such as carbon fiber. In some embodiments, the sheet is made with conductive ink applied to a polymeric film such as polyester film and is therefore not made with conductive fabric. In some embodiments, the heater is made of conductive film such as carbon or graphite-loaded plastic film.

The heater assembly may also include a first bus bar extending along the entire first edge of the heating element and adapted to receive a supply of electrical power, a second bus bar extending along the entire second edge of the heating element, and a temperature sensor. The layer of compressible material may be adapted to conform to a person's body under pressure from a person resting upon the support and adapted to return to an original shape when pressure is removed. It may be located beneath the heater assembly and may have a top surface and an opposing bottom surface, a length, and a width, with the length and width of the layer being approximately the same as the length and width of the heater assembly.

In some embodiments, the bus bars may be braided wire. In some embodiments, it may be desirable to coat the bus bars with a flexible rubber material such as silicone rubber, during construction of the heater. While braided wire is relatively tolerant of repeated flexion, if the flexion occurs enough times at the same spot, even braided wire bus bars can fracture and fail. Coating the bus bars with silicone rubber can significantly increase the durability of the bus bars to survive repeated flexion.

In some embodiments, the conductive or semi-conductive material is polypyrrole. In some embodiments, the compressible material includes a foam material, and in some embodiments it includes one or more air filled chambers. In some embodiments, the heated underbody support also includes a water resistant shell encasing the heater assembly, including an upper shell and a lower shell that can be sealed together along their edges to form a bonded edge, with the heater assembly attached to the shell only along one or more edges of the heater assembly. In some embodiments, the heating element has a generally planar shape when not under pressure. The heating element is adapted to stretch into a three-dimensional compound curve without wrinkling or folding while maintaining electrical conductivity in response to pressure, and may return to the same generally planar shape when pressure is removed.

In some embodiments, the heated underbody support includes a heater assembly including a flexible heating element comprising a sheet of conductive fabric having a top surface, a bottom surface, a first edge and an opposing second edge, a length, and a width, a first bus bar extending along the first edge of the heating element and adapted to receive a supply of electrical power, a second bus bar extending along the second edge of the heating element, and a temperature sensor. The underbody support may further include a layer of compressible support material located beneath the heater assembly, which conforms to a patient's body under pressure and returns to an original shape when pressure is removed.

In some such embodiments, the heating element includes a fabric coated with a conductive or semi-conductive material, which may be a carbon or metal containing polymer or ink, or may be a polymer such as polypyrrole. In some embodiments, the heated underbody support also includes a shell including two sheets of flexible shell material surrounding the heater assembly, the shell being a water resistant plastic film or fiber reinforced plastic film with the two sheets sealed together near the edges of the heater assembly. In some embodiments, the heated underbody support also includes a power supply and controller for regulating the supply of power to the first bus bar.

In some such embodiments, the compressible material is a foam material. The heater assembly may be attached to the top surface of the layer of compressible material. In some embodiments, the heated underbody support includes a water-resistant shell encasing the heater assembly and having an upper shell and a lower shell that are sealed together along their edges to form a bonded edge. In some such embodiments, one or more edges of the heater assembly may be sealed into the bonded edge. In some embodiments, the heater assembly is attached to the upper layer of water-resistant shell material. In some embodiments, the heater assembly is attached to the shell only along one or more edges of the heater assembly. In some embodiments, the heated underbody support also includes an electrical inlet, wherein the inlet is bonded to the upper shell and the lower shell and passes between them at the bonded edge.

In some embodiments, the temperature sensor is adapted to monitor a temperature of the heating element and is located in contact with the heating element in a substantially central location upon which a patient would be placed during normal use of the support. In some embodiments, the heated underbody support also includes a power supply and a controller for regulating a supply of power to the first bus bar. Some embodiments of heating pads and mattresses have been disclosed in U.S. Pat. Nos. 8,604,391; 9,962,122; 10,201,935; and 10,206,248, the entire disclosures of which are incorporated by reference into the present disclosure.

Certain embodiments of the invention include an electric heating blanket including a flexible sheet-like heating element and a shell. In some embodiments, the heating element is similar to those previously described and disclosed for surfaces of heated underbody supports. The shell covers the heating blanket and includes two sheets of flexible material welded together. In some embodiments, the weld couples the sheets together about the edges of the heating element. In some embodiments, the weld couples the sheets about the edges of the sheets. Some embodiments of heating blankets have been disclosed in U.S. Pat. Nos. 8,283,602 and 8,772,676, the entire disclosures of which are incorporated by reference into the present disclosure.

Figure 2:
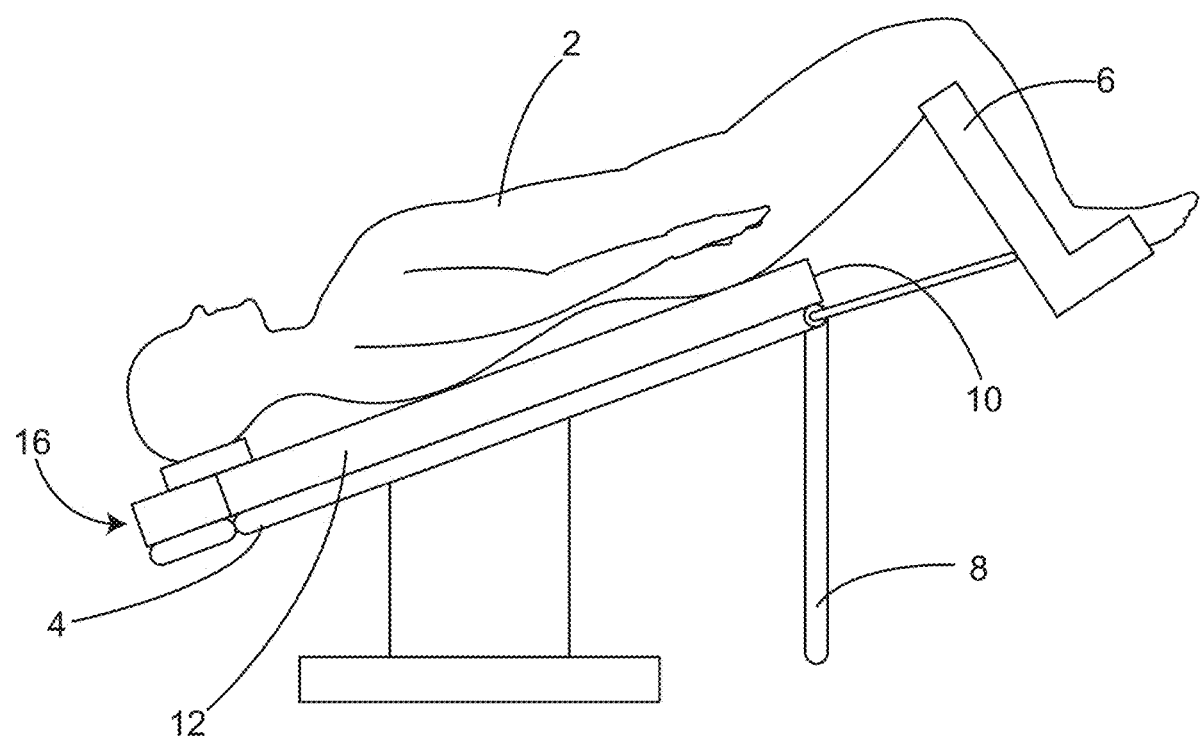
FIG. 2 is a side view of a patient lying on a surgical table in the Trendelenburg position in accordance with illustrative embodiments.
Figure 3:
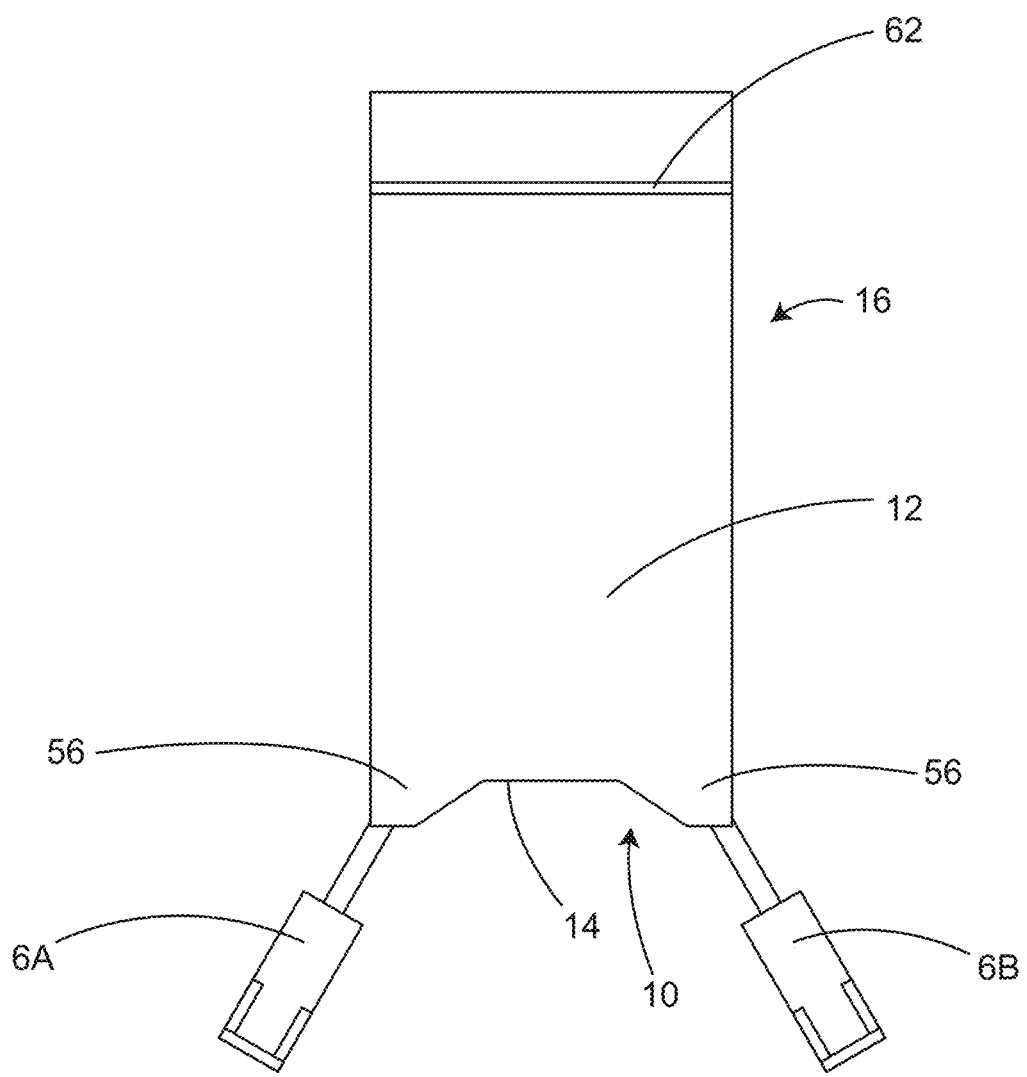
FIG. 3 is a top view of a surgical table with the foot section lowered and stirrups attached for the lithotomy position in accordance with illustrative embodiments.

The steep Trendelenburg position is often used during urological, gynecological and colorectal surgery, especially if the surgery is done with robotic or laparoscopic techniques. As shown in FIG. 2, the patient 2 is typically positioned supine on the surgical table 4 with their legs elevated in stirrups 6. In some cases, each stirrup 6 is shown individually in the drawings as reference numerals 6A and 6B. The surgical table 4 can optionally comprise metal. The foot end 8 of the surgical table 4 is lowered to allow the surgeon or robot access to the perineum of the patient. The steep Trendelenburg position allows gravity to pull the abdominal contents out of the pelvis for unobstructed access and visualization with the laparoscope. The patient's buttock is typically positioned at the foot end 10 of the underbody support or at the foot end 10 of the section 12 of the surgical table mattress 30 that supports the torso of the patient 2. The foot end 10 of the underbody support 16 or section 12 of the surgical table mattress 30 that is supporting the patient's torso typically has a notch cut out of the middle of the foot end, known as the perineal cutout 14, as shown in FIG. 3. The perineal cutout 14 allows the patient's perineum to hang slightly over the end of the center of the surgical table mattress 30 while still providing support on the lateral aspects of the buttock when the legs are elevated. The perineal cutout aids in unobstructed access to the patient's perineum by the surgeon or robot.

The underbody support 16 may include elements for anchoring the underbody support 16 to the surgical table 4. In some embodiments, the elements for anchoring may be a Velcro attachment between the upper surface of the surgical table 4 and the lower surface of the underbody support 16. The lower surface may also be called the table interface surface.

Figure 4:
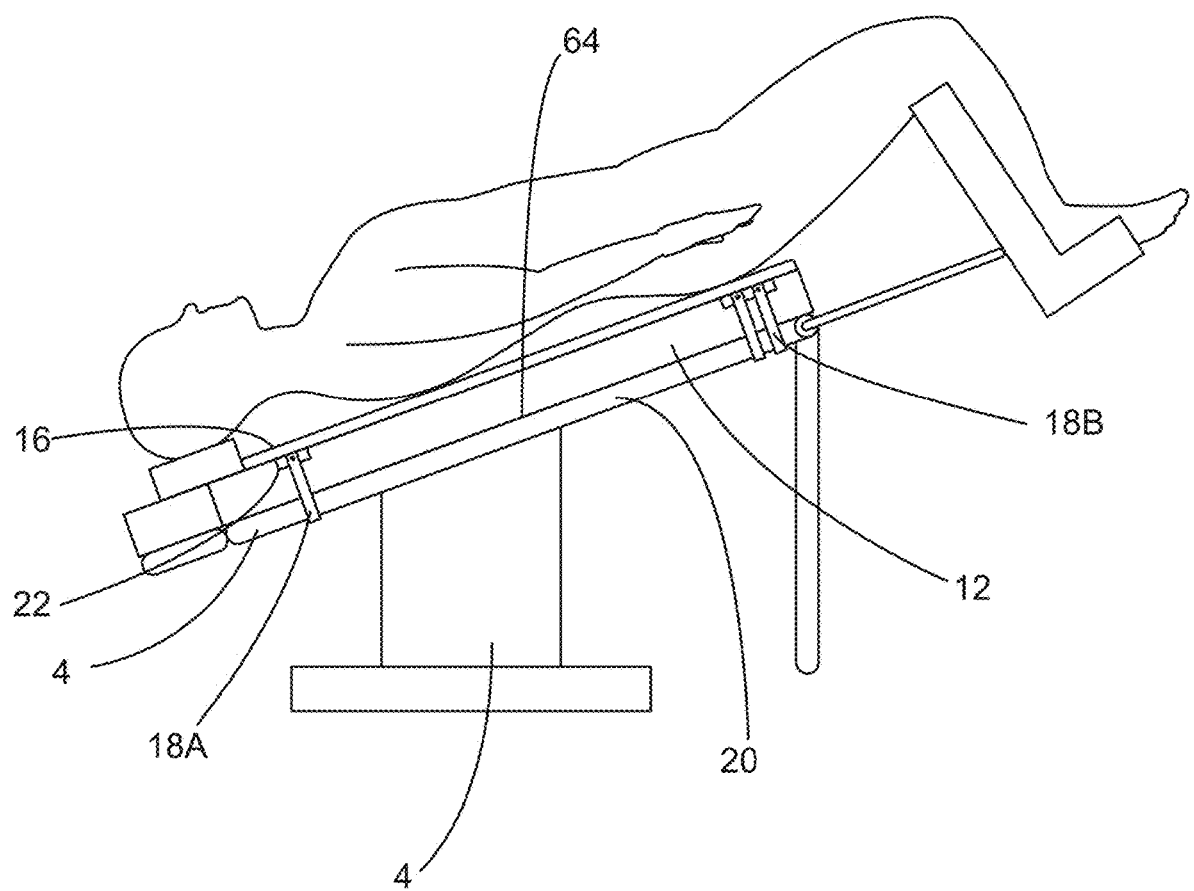
FIG. 4 is a side view of a patient laying on a surgical table and underbody support, in the lithotomy and Trendelenburg positions in accordance with illustrative embodiments.

In some embodiments, the elements for anchoring the underbody support 16 may be a strap attachment between the side of the surgical table 4 and the durable shell of the underbody support 16. As shown in FIG. 4, the straps 18 of the strap attachment may be made of non-stretching, reinforced strap material that can be looped around the side rails 20 of the surgical table 4 and then secured back onto itself. In some cases, the straps 18 are shown individually in the drawings as reference numerals 18A and 18B. The straps 18A, 18B may be secured with buttons, snaps, hooks, barbs, Velcro, or any other suitable secure attachment. In some embodiments, the straps 18A and 18B may be attached to the underbody support 16 at one or more strap attachment protrusions 22 of the upper and lower shell material layers, from the side of the underbody support 16. The one or more strap attachment protrusions 22 may be part of the perimeter weld between the upper and lower shell material layers of the underbody support 16, previously discussed. The one or more strap attachment protrusions 22 may be reinforced with a mesh of fibers such as nylon for added strength.

Figure 5:
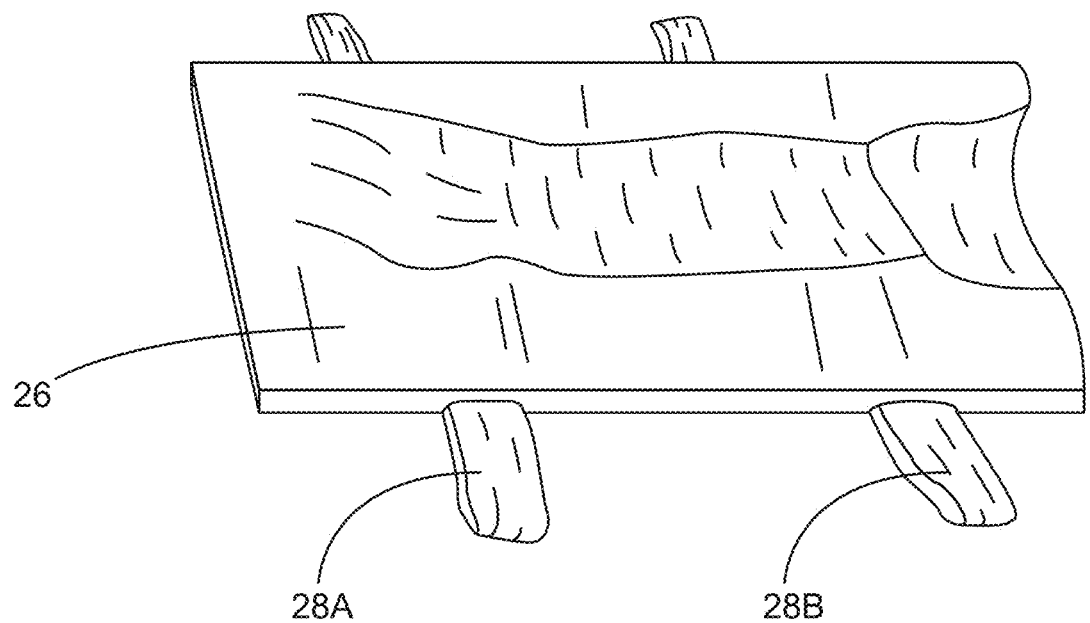
FIG. 5 is a perspective view of a securement pad in accordance with illustrative embodiments.
Figure 6:
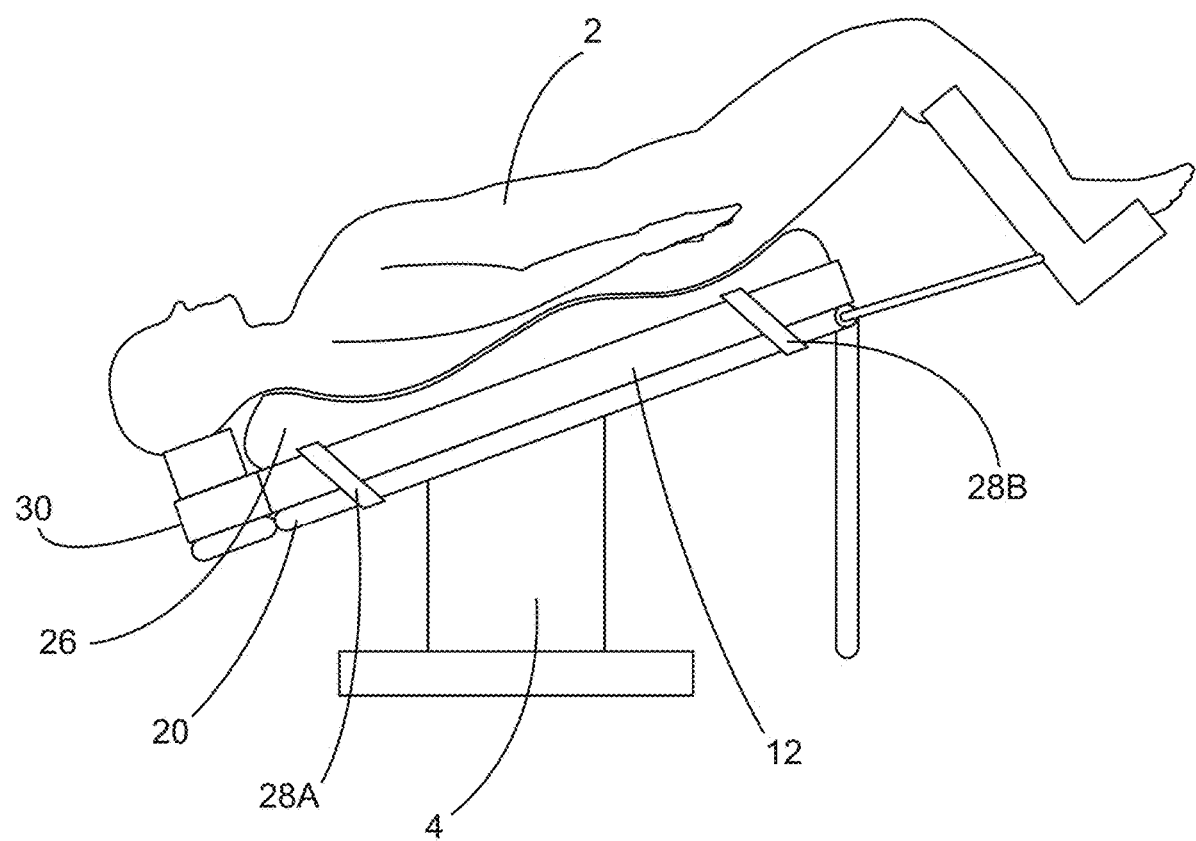
FIG. 6 is a side view of a patient laying on a surgical table and securement pad, in the lithotomy and Trendelenburg positions in accordance with illustrative embodiments.

In some embodiments, the shell material of the underbody support 16 may be reinforced with a mesh of fibers such as nylon embedded in the shell material during the shell material extrusion process. The fiber reinforcement may be included in the lower shell layer, the upper shell layer, or in both shell layers. The reinforcing fibers prevent the shell material from stretching and deforming when a heavy patient is placed in the steep Trendelenburg position, creating a sliding force between the layers of the underbody support or between the underbody support 16 and the surgical table mattress 30 or the surgical table top 64. This reinforced construction of the underbody support 16 in conjunction with the reinforced construction of the strap attachment protrusions 22 of the underbody support 16 together with the reinforced construction of the straps 18A, 18B connected to the side rails 20 of the surgical table 4, or Velcro attachment to the surgical table top 64, assures that the underbody support 16 will remain stable and not shift or slide when the patient is placed in the steep Trendelenburg position. In some embodiments, the durable construction of this underbody support 16 prevents deformation and stretching in any direction parallel to the plane of the support, thus preventing slippage between the underbody support 16 and the surgical table 4. The stability and inability to deform in response to the weight of the patient pulling the patient down the slope of the surgical table 4 provided by this construction, is in contrast to the relatively fragile and flexible construction of conventional disposable securement pads. As shown in FIGS. 5 and 6, conventional (e.g., flexible) securement pads 26 will easily deform in response to forces applied parallel to the plane of the securement pad 26, and this deformation results in slippage between the securement pad 26 and a section 12 of the surgical table mattress 30.

Additionally, as shown in FIG. 5, such type of securement pad 26 includes pad straps 28A, 28B that anchor the securement pad 26 to the side rails 20 of the surgical table 4. However, as shown in FIG. 6, anchoring these types of securement pads 26 to the side rails 20 allows a natural 1-3 inches of slippage between the securement pad 26 and the surgical table 4. This slippage in this type of securement pad 26 is due to the force of the patient's weight being applied perpendicularly to the direction of the pad straps 28A, 28B that are nondurable and stretchable and glued to the securement pad 26 that is typically made of a stretchable sheet of flexible viscoelastic foam. These pad straps 28A, 28B, which are perpendicularly oriented, nondurable, flexible, and stretchable, in conjunction with the conventional securement pad 26 (which is often a flexible and deformable foam) stretch and flex in combination, allowing the securement pad 26 to slide down the surgical table mattress 30 up to three inches in the steep Trendelenburg position, before arresting the slide. A sliding motion down the steep incline of the table cannot be prevented when perpendicular forces to the side rails 20 are applied to pad straps 28A, 28B that are glued to the securement pad 26 (when such pad is a flexible foam pad). The side rails 20 of the surgical table 4 are a convenient attachment point for known devices but cannot prevent 1-3 inches of sliding down the incline of a surgical table 4 in the Trendelenburg position using the pad straps 28A, 28B and securement pad 26 described above.

Figure 7A:
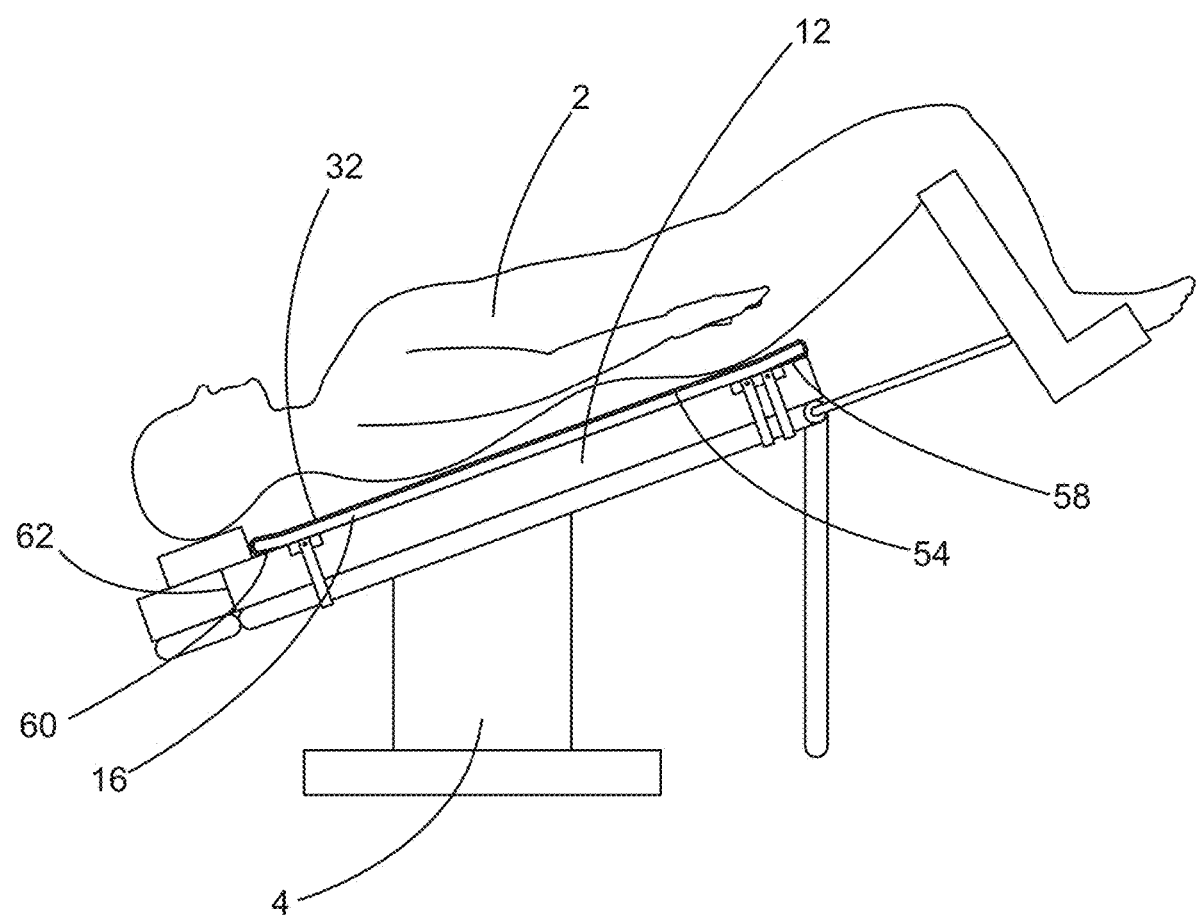
FIG. 7A is a side view of a patient laying on a surgical table, underbody support and sheet of fabric, in the lithotomy and Trendelenburg positions in accordance with illustrative embodiments.
Figure 7B:
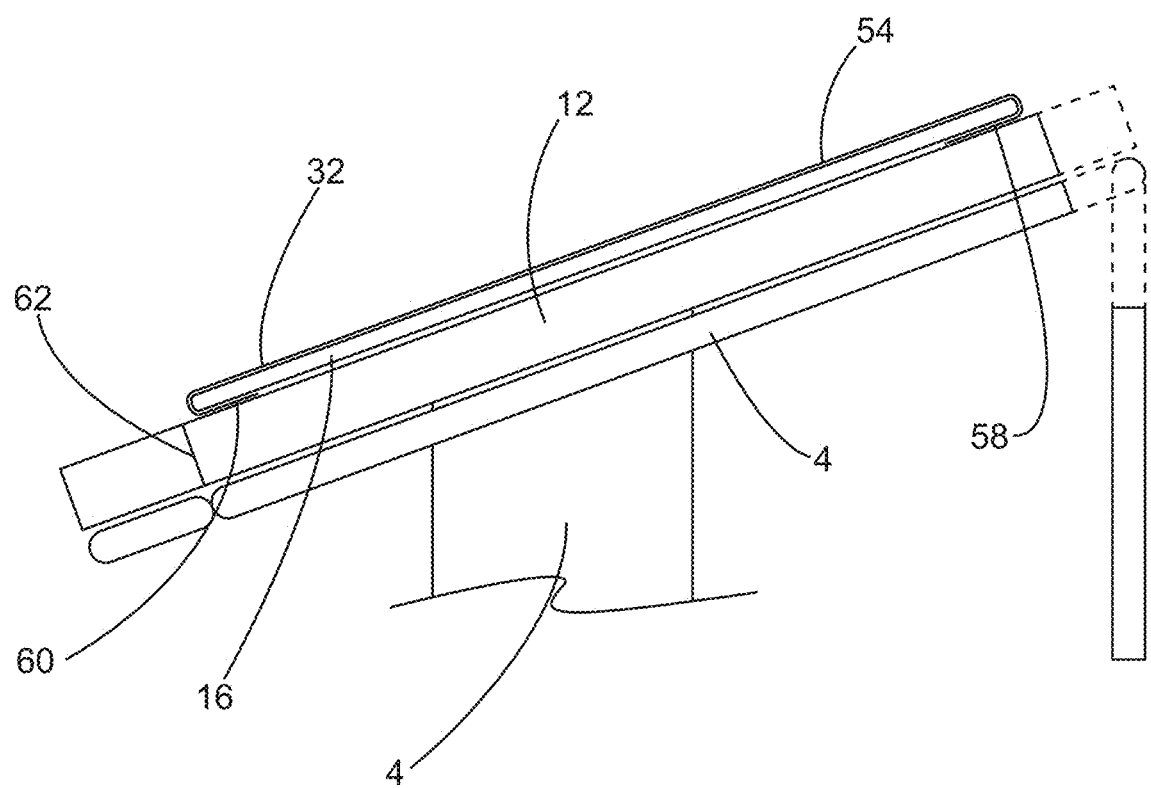
FIG. 7B is a side view of a surgical table with an underbody support and sheet of fabric in the Trendelenburg position, in accordance with illustrative embodiments.
Figure 8:
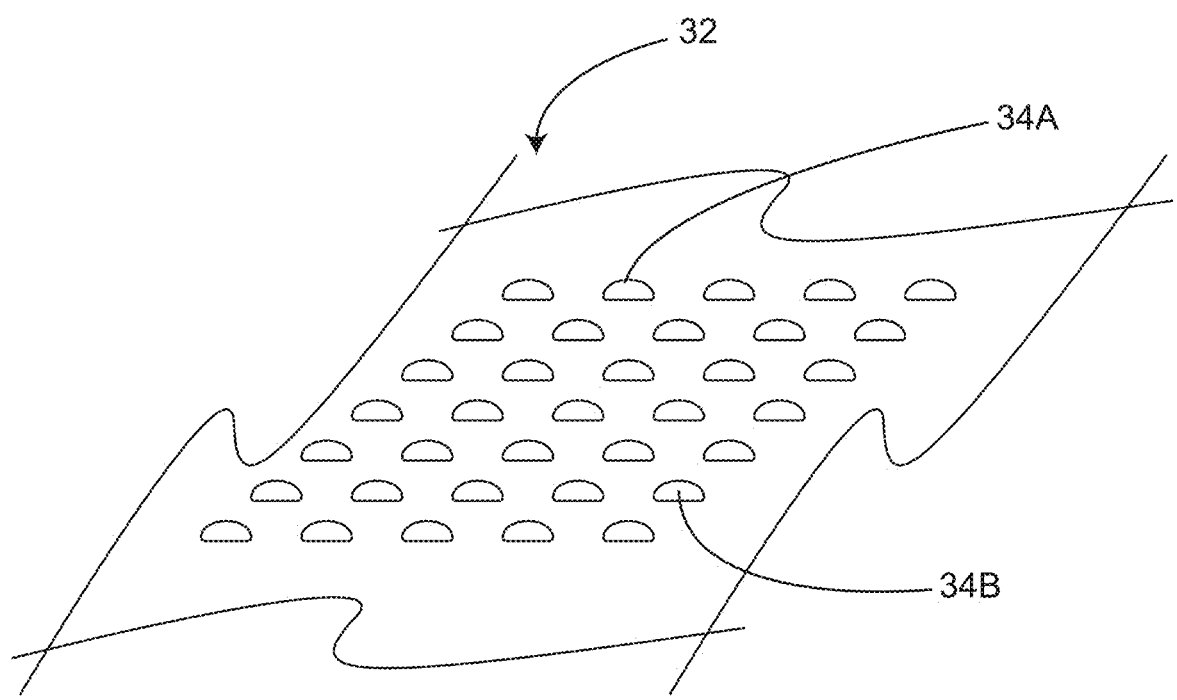
FIG. 8 is a detailed perspective view of a sheet of fabric, in accordance with illustrative embodiments.
Figure 9:
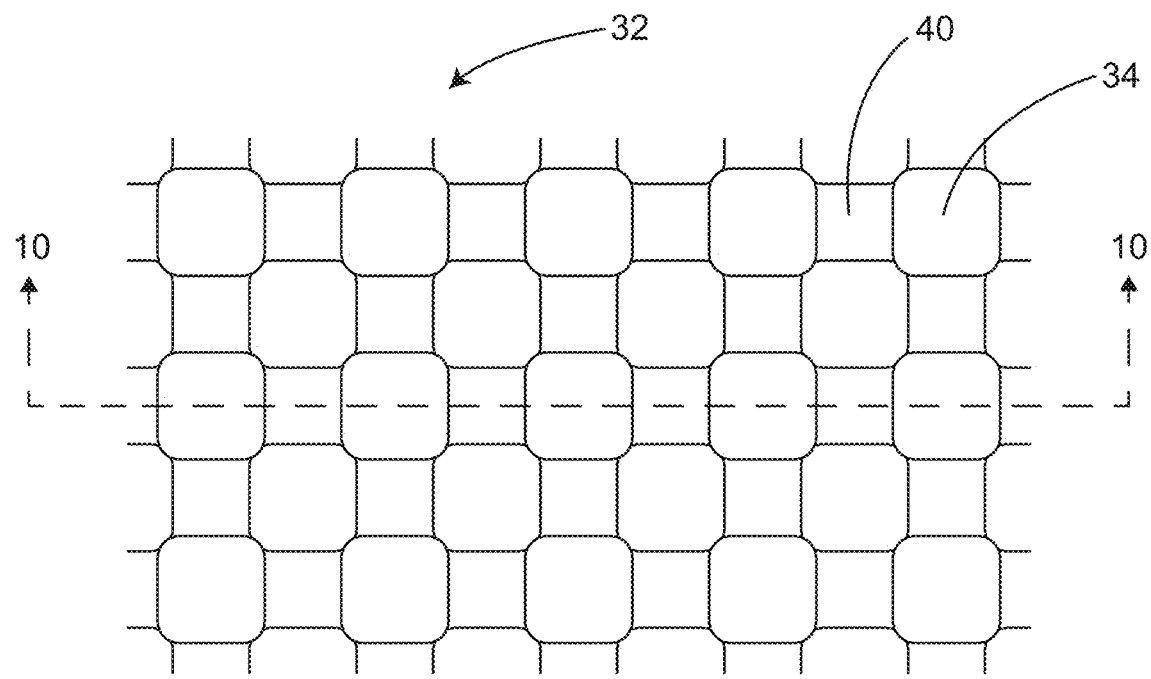
FIG. 9 is a detailed top view of a sheet of fabric, in accordance with illustrative embodiments.

In some embodiments, as shown in FIGS. 7A and 7B, a sheet of fabric 32 that has been at least partially coated on both sides with friction-enhancing elements 34 may be interposed between the patient 2 and the underbody support 16 in order to increase the coefficient of friction therebetween. In any embodiment described herein, the sheet of fabric 32 can be separate from the underbody support 16 and removably positionable onto the underbody support 16. The friction-enhancing elements 34 may be high-friction plastic or rubber, or a material having similar characteristics. An example of material for the friction-enhancing elements 34 may be PVC, silicone, polyethylene or other plastic or rubber materials that may be applied as a three-dimensional pattern or three-dimensional raised dots onto a fabric. As shown in FIGS. 8 and 9, the friction-enhancing elements 34 may be in the form of a pattern or dots, and grip the upper surface of the underbody support 16 on one side and the back of the patient 2 on their other side, dramatically increasing the coefficient of friction between the patient 2 and a surface of the underbody support 16, preventing the two from slipping against each other. Alternately, the friction-enhancing elements 34 may be applied directly to the upper surface of the underbody support 16. The upper surface may also be called a patient interface surface.

In some embodiments, a sheet of fabric 32 is interposed between the upper surface of the underbody support 16 and the back of the patient 2 in order to increase the coefficient of friction between these two surfaces. The sheet of fabric 32 may be either woven or non-woven and may be made of any durable fiber such as polyester, rayon, nylon or cotton. Other fibers for the sheet of fabric 32 are also anticipated. In some embodiments, if a fluid impervious layer is desirable, the sheet of fabric 32 in this disclosure may be made of plastic film or plastic film coated or laminated onto one or both sides of a sheet of fibrous fabric. The plastic film layer may be made of polyethylene, polypropylene, PVC, urethane or other suitable films.

In some embodiments, the sheet of fabric 32 is partially coated on at least its upper surface 36 with friction-enhancing elements 34. The friction-enhancing elements 34 can be a plastic or rubber three-dimensional friction-enhancing elements, such as a three-dimensional raised pattern of circular, square, rectangular or oblong elements. In some embodiments, the friction-enhancing elements 34 are between 0.1 inches and 0.5 inches in diameter or cross section. The friction-enhancing elements 34 include but are not limited to: PVC foams, viscoelastic PVC foams, silicone, viscoelastic polyurethane foams, other viscoelastic polymeric foams, urethane, PVC, as well as other polymers and rubbers.

Figure 10:
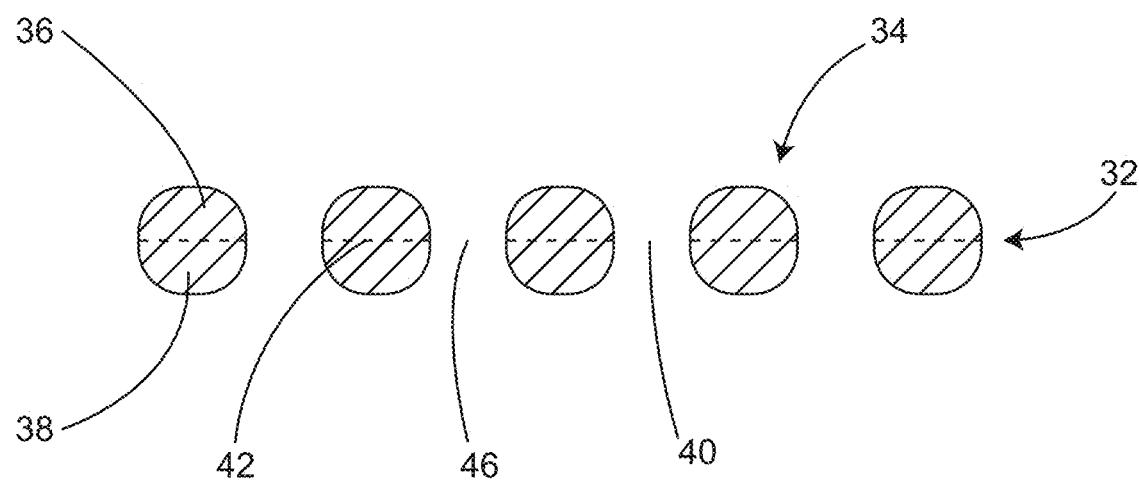
FIG. 10 is a detailed cross-sectional view of a sheet of fabric taken along line 10-10 of FIG. 9, in accordance with illustrative embodiments.
Figure 11:
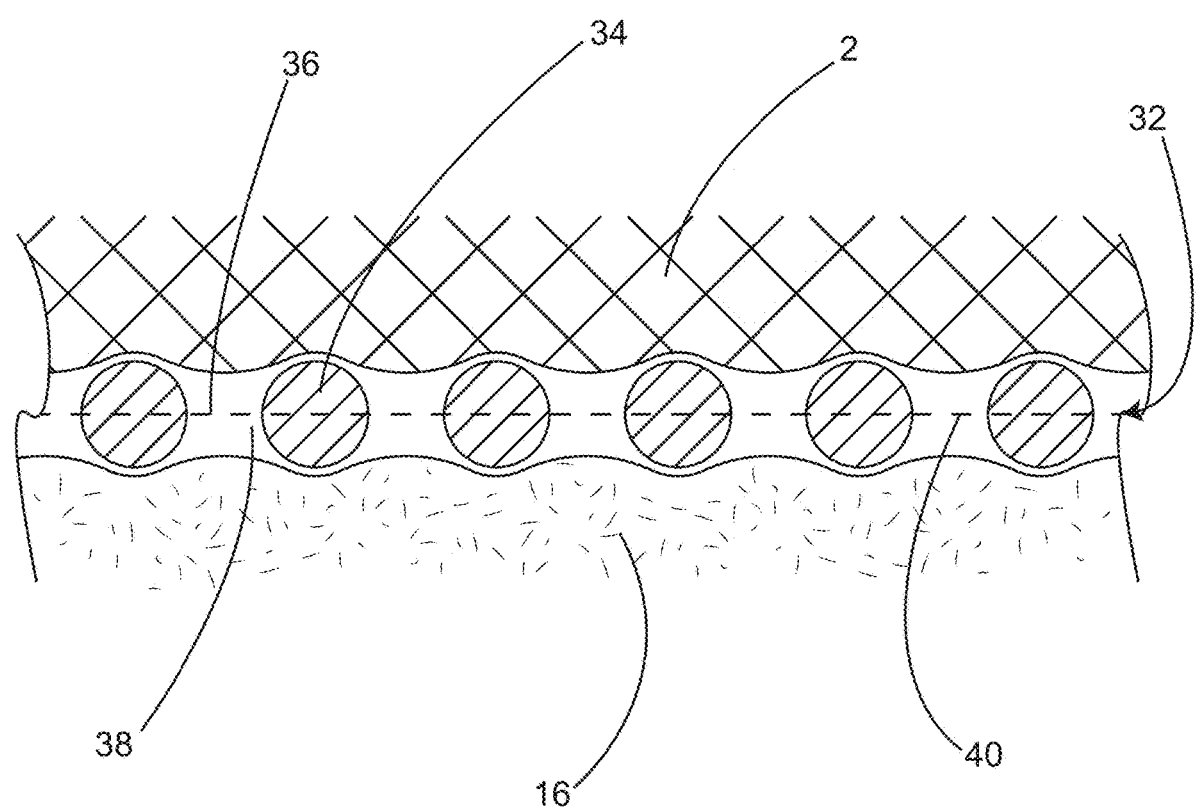
FIG. 11 is a detailed cross-sectional view of a sheet of fabric taken along line 10-10 of FIG. 9, positioned between the patient and the underbody support in accordance with illustrative embodiments.

In some embodiments, as shown in FIGS. 10 and 11, the sheet of fabric 32 is partially coated on both the upper surface 36 and the lower surface 38 with friction-enhancing elements 34. The friction-enhancing elements 34 can be plastic or rubber three-dimensional friction-enhancing elements, such as a three-dimensional raised pattern of circular, square, rectangular or oblong elements. In some embodiments, the friction-enhancing elements 34 on the upper surface 36 and lower surface 38 are three-dimensional friction-enhancing elements that directly oppose each other in size and location on each side of the sheet of fabric 32. As used herein, friction-enhancing elements 34 that directly oppose each other in both size and location refers to friction-enhancing elements 34 that are positioned directly opposite one another on opposite sides of the sheet of fabric 32 and that have the exact same dimensions (or substantially the same dimensions) as each other. Direct opposition of the friction-enhancing elements 34 on both sides of the sheet of fabric 32 improves the transmission of force between the upper surface of the underbody support 16 and the patient's back, at that point. The ability of the friction-enhancing elements 34 on each side of the sheet of fabric 32 to increase the coefficient of friction by indenting the patient's back 2 on one side and the underbody support 16 on the other side is reduced if the friction-enhancing elements 34 on each side of the sheet of fabric 32 are not directly opposing each other. In some embodiments, the friction-enhancing elements 34 are three-dimensional friction-enhancing elements intended to press into the patient's skin creating a small indentation that adds to the mechanical interaction between the sheet of fabric 32 and the patient's skin. This mechanical interaction between the sheet of fabric 32 and the patient's skin, indenting the skin, augments the normal coefficient of friction between the two surfaces. Locating the friction-enhancing elements 34 directly opposing each other on each side of the sheet of fabric 32, maximizes the ability of each friction-enhancing element 34 to transmit force from the underbody support 16 to the patient's back.

In some embodiments, as shown in FIGS. 9, 10 and 11, the friction-enhancing elements 34 on the upper surface 36 of the sheet of fabric 32, which can be a three-dimensional raised pattern of friction-enhancing elements, may form a matrix leaving the sheet of fabric 32 with holes 40 in the areas between the raised pattern of friction-enhancing elements. The holes 40 in the sheet of fabric 32 may advantageously allow the free passage of heat, air and moisture through the sheet of fabric 32. When the underbody support 16 is a heated underbody support, the holes 40 allow heat from the underbody support 16 to freely pass through the sheet of fabric 32 to the patient to provide effective warming. This is in contrast to the thermally insulating quality of conventional securement pads 26 (e.g., comprising foam) that prevent effective underbody patient warming. The holes 40 in the sheet of fabric 32 of the present disclosure may also advantageously allow the free passage of moisture through the sheet of fabric 32, removing the perspiration or skin prep antiseptic solutions that could be contacting the patient's skin and making the skin more susceptible to pressure injury.

Figure 12:
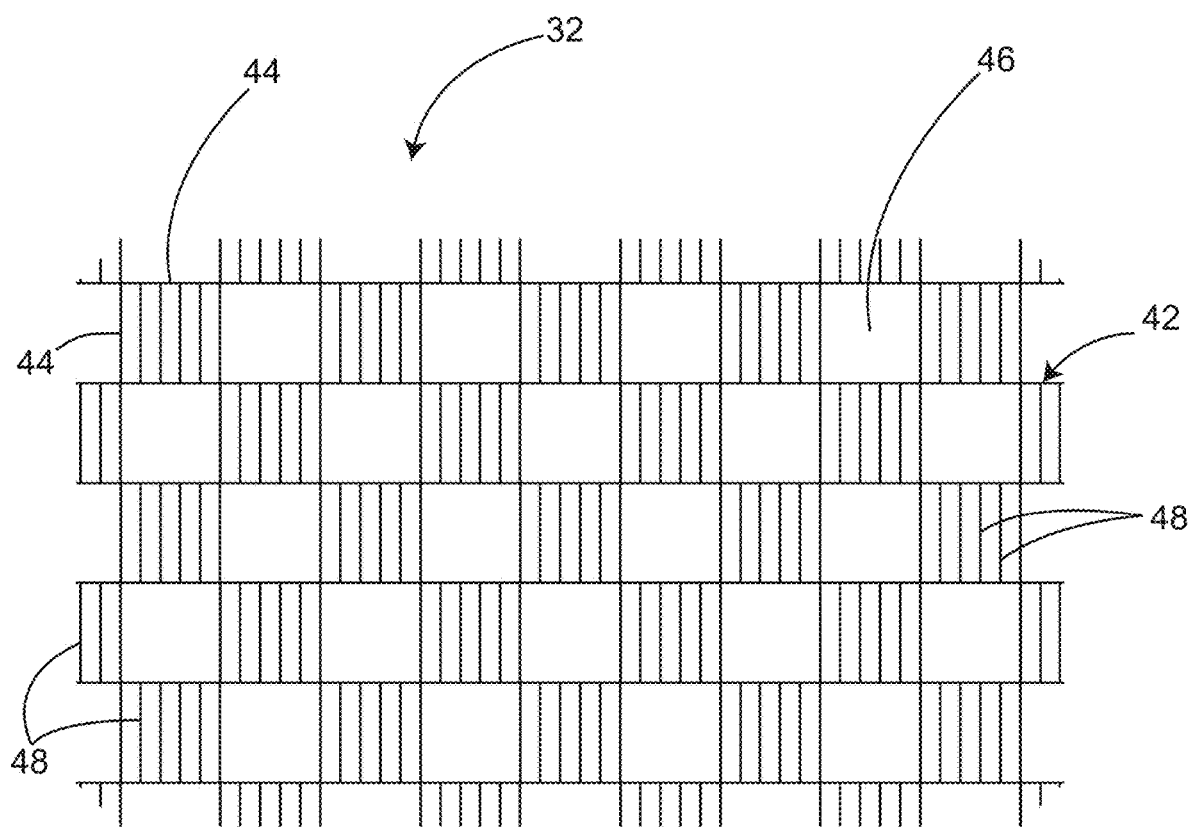
FIG. 12 is a detailed top view of the scrim, in accordance with illustrative embodiments.

In some embodiments, as shown in FIG. 12, the construction of a sheet of fabric 32 with friction-enhancing elements 34 that are three-dimensional and that directly oppose each other on both sides of the fabric and with holes or uncoated spaces 40 in between the friction-enhancing elements 34, may be made by starting with a scrim 42, which can be a fabric scrim made of polyester or other suitable fibers. The threads 44 of the scrim 42 may be woven or knitted into a pattern such as a checkerboard pattern for example, with open spaces 46 between the matrix of threads 44. The open spaces 46 between the threads may be between about 0.05 inches and about 0.25 inches in diameter. In open spaces 46, similar to the black spaces on a checkerboard, additional threads 48 may be added during the weaving or knitting process. As shown in FIG. 9, when a foamed PVC compound is coated onto this scrim 42 sheet of fabric 32, the liquid PVC sticks to the spaces where additional threads 48 were added and open holes or uncoated spaces 40 are formed in the open spaces 46 where additional threads were not added. The foamed PVC naturally and advantageously forms friction-enhancing elements 34 that can be three-dimensional friction-enhancing elements directly opposing each other on each side of the sheet of fabric 32 where the additional threads 48 were added and leaves holes or uncoated spaces 40 in between the friction-enhancing elements 34 (Kittrich Corp.).

In some embodiments, the area of one hole 40 may advantageously be less than the area of one of the friction-enhancing elements 34. In some embodiments, the area of one of the holes 40 may advantageously be less than 0.1875 square inches. Holes 40 that are larger than 0.1875 square inches disadvantage both the area of skin supporting the weight of the patient's body and the natural tackiness between the friction-enhancing elements 34 and the skin. Further, holes 40 that are larger than 0.1875 inches square may create a hydrostatic pressure gradient within the patient's skin protruding into the hole 40 resulting in a pattern of petechiae or bruising.

Figure 13:
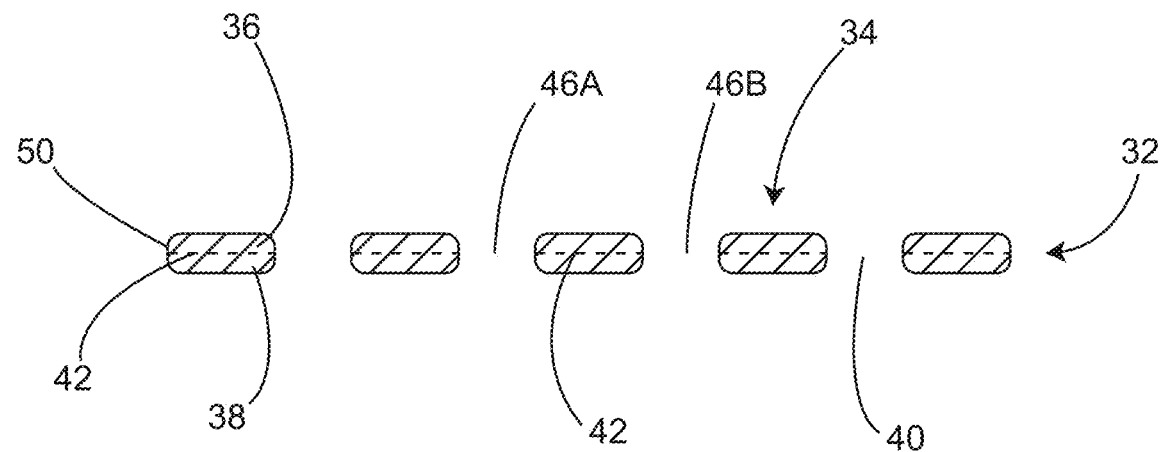
FIG. 13 is a detailed cross-sectional view of a sheet of fabric taken along line 10-10 of FIG. 9, in accordance with illustrative embodiments.

In some embodiments, as shown in FIG. 10, the friction-enhancing elements 34 formed on the (e.g., open weave) scrim 42 sheet of fabric 32 are approximately 0.125 inches in total thickness. Such friction-enhancing elements 34 can be foamed PVC three-dimensional friction-enhancing elements. Applicant has found that these 0.125 inch thick dots or beads in a matrix formation with spaces in between the dots may cause mild petechiae (bruising or extravasation, blood leaking into the unsupported skin tissue that is pressed into the open spaces of the checkerboard pattern). This problem with petechiae may be mitigated by flattening at least the friction-enhancing elements 34 on the upper surface 36 of the sheet of fabric 32 when those friction-enhancing elements 34 are rounded three-dimensional friction-enhancing elements. In some embodiments, as shown in FIG. 13, the sheet of fabric 32 with friction-enhancing elements 34 that are foamed PVC three-dimensional friction-enhancing elements and that have open spaces 46 therebetween can be flattened by running it through a heat laminating process that may flatten the three-dimensional dots from approximately 0.125 inches in thickness to approximately 0.05-0.10 inches in thickness. In some cases, each open space 46 is shown individually in the drawings as reference numerals 46A and 46B. Flattening the foamed PVC three-dimensional friction-enhancing elements does not close the checkerboard of holes 40 between the friction-enhancing elements 34 but it does make the holes 40 slightly smaller in surface area compared to the surface area of the adjacent friction-enhancing elements 34. In some embodiments, a heat laminator may heat the sheet of fabric 32 before running it through two compression rollers. Alternately, the sheet of fabric 32 may be run through two compression rollers of which one or both are heated. The flattened friction-enhancing elements 50 (which can be foamed PVC three-dimensional friction-enhancing elements) having holes 40 of smaller diameter therebetween, may not cause petechiae but also do not grip the patient as effectively.

Where the friction-enhancing elements 34 are foamed PVC three-dimensional friction-enhancing elements, flattening these friction-enhancing elements 34 in a heat laminator process also alters the surface characteristic of the foamed PVC material, making it substantially stickier. The heating and compression process disrupts the normal "skin" that forms on the surface of foam as it cures. Disrupting the surface "skin" exposes the "stickier" inner foam. The stickier PVC foam further increases the coefficient of friction between the underbody support 16 and the patient 2. The "stickier" PVC foam may stick to the patient better than the skinned foam but it does not stick as well to adhesives. The exposed plasticizer in the foam interferes with the adhesion of adhesives. Therefore, if pieces of the sheet of fabric 32 are intended to be adhesively bonded to the draw sheet 76 or other materials, it may be advantageous to adhesively bond to the non-compressed side of the sheet of fabric 32. The original "skin" characteristic of the foamed PVC material on the lower surface 38 helps with adhesive bonding. The stickier foam PVC in the presence of heat from the underbody support 16 and pressure from the weight of the patient 2, may leave an unsightly residue of foam adhered to the underbody support 16. In some embodiments, this adhesion residue may be prevented by heating and flattening the friction-enhancing elements 34 on the upper surface 36 of the sheet of fabric 32, while leaving the original "skin" characteristic of the foamed PVC material on the lower surface 38 substantially unchanged and less sticky. The original "skin" characteristic of the foamed PVC material on the lower surface 38 helps to prevent the residue of foam from adhering to the underbody support 16.

Figure 14:
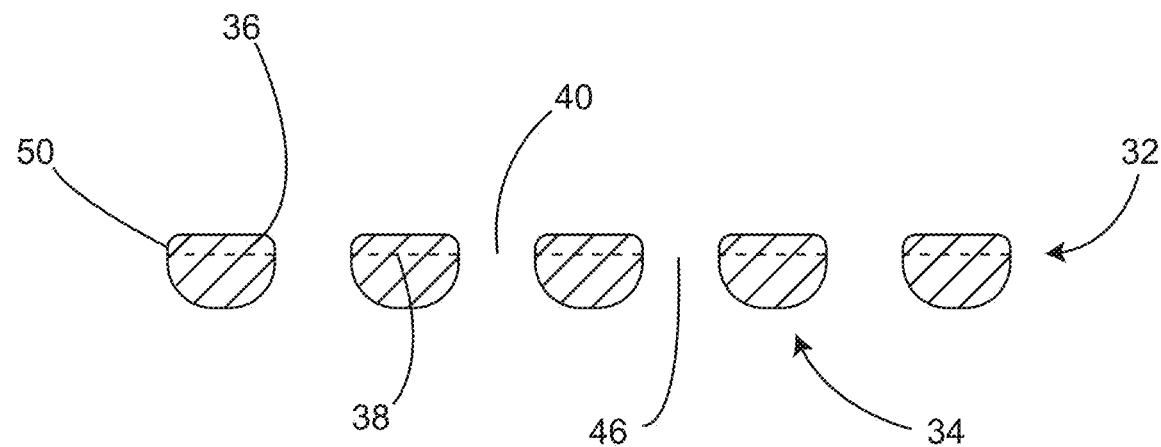
FIG. 14 is a detailed cross-sectional view of a sheet of fabric taken along line 10-10 of FIG. 9, in accordance with illustrative embodiments.

In some embodiments, as shown in FIG. 14, the flattening of the friction-enhancing elements 34 to form friction-enhancing elements 50 on the upper surface 36 of the sheet of fabric 32 can be accomplished by heating the upper surface and/or heating the upper compression roller or both. In some embodiments, the original structure, shape and surface integrity of the friction-enhancing elements 34 on the lower surface 38 of the sheet of fabric 32 may be preserved by heating the upper surface and minimally heating the lower surface and/or cooling the lower compression roller during the compression process.

In some embodiments, the sheet of fabric 32 with friction-enhancing elements 34 (which can be foamed PVC three-dimensional friction-enhancing elements) and having uncoated spaces or holes 40 therebetween, can be flattened and thinned by running it through a heated compression process. The heated compression process may advantageously produce a patient securement device with very little thickness (compared to conventional thick foam pad securement devices) yet retain most of the gripping characteristics.

In some embodiments, the underbody support 16 may also serve as a capacitive coupling electrosurgical grounding electrode. Effective capacitive coupling requires that the two electrical conductors be separated by only a thin dielectric (electrical insulator). Capacitive coupling of RF electrical energy is most efficient and effective when the patient's skin is separated from the grounding antenna by a thin dielectric or electrical insulating material. A thick dielectric, for example greater than 0.5 inches, will prevent effective capacitive coupling electrosurgical grounding. The friction-enhancing elements 34 (which can be three-dimensional friction-enhancing elements) on the sheet of fabric 32 of the present disclosure create a thin dielectric. The thickness of this dielectric may be further decreased by heating and compressing the friction-enhancing elements 34 between two rollers as described above in order to form flattened friction-enhancing elements 50, which further enhances the effectiveness of the capacitive coupling. In some embodiments, the thin nature of the sheet of fabric 32 of the instant invention (such as less than 0.125 inches thick), allows effective capacitive coupling electrosurgical grounding. The capacitive coupling may be even further enhanced by the holes or uncoated spaces 40 that are formed between the friction-enhancing elements 34, 50, where there is no added electrical insulating (dielectric) properties caused by the sheet of fabric 32. The invention of this disclosure is uniquely suited for use with capacitive coupling electrosurgical grounding. In contrast, the conventional (e.g., thick foam) securement pads 26 prevent effective capacitive coupling from occurring.

Figure 15:
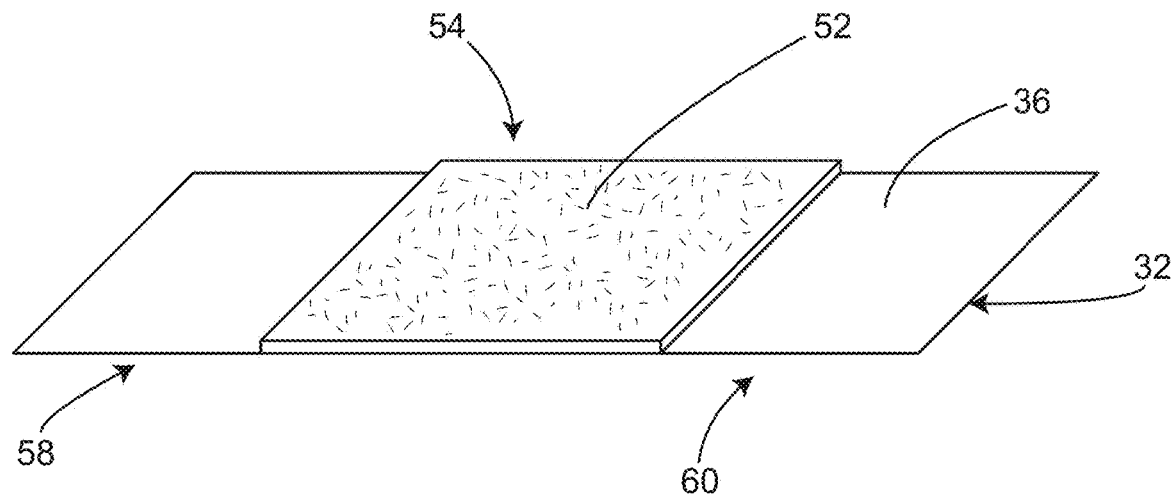
FIG. 15 is a perspective view of a sheet of fabric with a layer of foam material in accordance with illustrative embodiments.

In some embodiments, the total thickness of each of the (e.g., three-dimensional) friction-enhancing elements 34 on both the upper 36 and lower 38 surfaces of the sheet of fabric 32 is less than 0.25 inches. In some embodiments, as shown in FIG. 15, a layer of flexible foam material 52 is adhesively laminated to the upper surface 36 of the sheet of fabric 32. In some cases, the layer of flexible foam material 52 is less than 0.75 inches thick. Laminating a layer of flexible foam material 52 to the sheet of fabric 32, substantially increases the strength, stability and tear resistance of the layer of flexible foam material 52. The minimal thickness of the resulting patient securement overlay 54 compared to known securement pads, eliminates the bolster effect that would occur with a thicker non-weight bearing foam surrounding the patient especially at the shoulders. When the layer of flexible foam material 52 is relatively thin, the patient cannot appreciably sink into the foam so as to create a bolster effect. This is advantageous because effectiveness of patient securement by a bolster effect is limited by the patient's weight and the shape of their shoulders. For example, heavy patients and rounded shoulders can overcome the ability of a bolster to prevent sliding.

In some embodiments, minimizing or even eliminating any weight-limited patient securing bolster effect in the patient securement overlay 54 by limiting the thickness to less than 0.75 inches, results in a patient securing effectiveness that is determined nearly exclusively by the coefficient of friction between the patient and the patient securement overlay 54. Coefficient of friction is by definition, independent of the patient's weight. In some embodiments, due to the physical properties of the coefficient of friction, the effectiveness of this patient securement device is independent of the patient's weight and is only limited by the angle of the decline. Therefore, due to the physical properties of the coefficient of friction, the patient securement device of the instant disclosure can accommodate patients of any size or weight, without limitation. The instructions for use of this device may only limit the angle of decline. Most known bolster-type patient securement devices are limited to certain weights, usually 300-400 pounds. The instructions for use of bolster-type devices limit both the angle of decline and weight of the patient.

In some embodiments, as shown in FIGS. 7A and 7B, the patient securement overlay 54 is advantageously anchored to at least a portion of the foot end of the section 12 of the surgical table mattress 30 that supports a torso of a patient 2 on a surgical table 4. In some embodiments, the patient securement overlay 54 is advantageously anchored to at least a portion of the foot end 10 of the underbody support 16. Anchoring the patient securement overlay 54 to at least a portion of the foot end 10 of the section 12 of the surgical table mattress 30 or underbody support 16 that supports the patient's torso creates a positive coupling between the two layers, when the patient is in the Trendelenburg position. Since a section 12 of the surgical table mattress 30 or underbody support 16 can be positively anchored to the surgical table 4 and the patient securement overlay 54 can be positively anchored to at least a portion of the foot end 10 of the underbody support 16 or to the surgical table mattress 30, the patient securement overlay 54 is thus positively and uniquely, indirectly anchored to the surgical table 4.

As shown in FIG. 3, the foot end 10 of the section 12 of the surgical table mattress 30 that supports the patient's torso on a surgical table 4 typically includes a perineal cutout 14 in the center of the foot end of section 12 of the surgical table mattress 30. The perineal cutout 14 of the section 12 of the surgical table mattress 30 is typically a tapering 3-6 inch recess in the foot end of the surgical table mattress 30 that is typically 10-14 inches wide at the open side of the recess and 4-8 inches wide at the closed side of the recess. Lateral to each side of the perineal cutout 14 are side extensions 56 of the surgical table mattress 30. The side extensions may extend approximately 4-6 inches out from each side of the perineal cutout 14. The perineal cutout 14 allows the patient's perineum to hang slightly over the end of the center of the surgical table mattress 30 while allowing side extensions 56 to provide support on the lateral aspects of the buttock when the patient's legs are up in stirrups. The perineal cutout 14 aids in unobstructed access to the perineum by the surgeon or robot.

In some embodiments, the perineal cutout 14 of the underbody support 16 may be a tapering 3-6 inch recess in the foot end of the underbody support 16 that may be 10-20 inches wide at the open side of the recess and 4-12 inches wide at the closed side of the recess.

In some embodiments, as shown in FIGS. 7A and 7B, the patient securement overlay 54 is advantageously anchored to at least a portion of the foot end 10 of the section 12 of the surgical table mattress 30 or underbody support 16 that supports the patient's torso on a surgical table 4, by a foot end extension 58 of the sheet of fabric 32 that wraps around at least a portion of the foot end 10 of the surgical table mattress 30 or underbody support 16 and is secured under the surgical table mattress 30 or underbody support 16. In some embodiments, the foot end extension 58 is a separate piece of material that is added to the patient securement overlay 54 as the anchor section.

In some embodiments, the width of the foot end extension 58 is less than the width of the patient securement overlay 54. In some embodiments, the width of the foot end extension 58 is advantageously approximately equal to the width of the closed side of the recess of the perineal cutout 14 of the surgical table mattress 30 or the underbody support 16. In some embodiments, the width of the foot end extension 58 may be between 4 and 20 inches. In some embodiments, the width of the perineal cutout 14 of the underbody support 16 may be greater than a width of the perineal cutout 14 of the surgical table mattress 30. When the perineal cutout 14 of the underbody support 16 is wider than the width of the perineal cutout 14 of the surgical table mattress 30, this may advantageously allow a wider and thus stronger foot end extension 58 of the sheet of fabric 32 to wrap around the perineal cutout 14 of the underbody support 16 and still fit within the perineal cutout 14.

In some embodiments, wrapping the foot end extension 58 of the sheet of fabric 32 around the closed side of the perineal cutout 14 provides significantly greater security than wrapping the foot end extension 58 around the foot end 10 of the section 12 of the surgical table mattress 30 that supports the patient's torso. First, the side extensions 56 of the section 12 of the surgical table mattress 30 on each side of the perineal cutout 14 create a buttress effect, preventing the upper edge of the closed side of the perineal cutout 14 from collapsing toward the head end when the patient is in the steep Trendelenburg position. Second, the weight of the patient's buttock centered directly over the area adjacent the closed side of the perineal cutout 14, focuses this weight on the exact area under the underbody support 16 that is anchoring the foot end extension 58. All other known surgical mattress covers and sheets are designed to cover the entire mattress which includes the side extensions 56 of the surgical table mattress on each side of the perineal cutout 14 as well as additional mattress sections at the head and foot end of the surgical table 4. In some embodiments, foot end extension 58 of the sheet of fabric 32 for anchoring the sheet of fabric 32, is wrapped around the closed side of the perineal cutout 14 for maximum security and strength.

In some embodiments, the patient securement overlay 54 is advantageously anchored to at least a portion of the head end 62 of the section 12 of the surgical table mattress 30 or underbody support 16 that supports the patient's torso, by a head end extension 60 of the sheet of fabric 32 that wraps around at least a portion of the head end 62 of the section 12 of the surgical table mattress 30 or underbody support 16 that supports the patient's torso and is secured under the surgical table mattress 30 or underbody support 16. In some embodiments, the head end extension 60 for anchoring the head end of the patient securement overlay 54 is a separate sheet of fabric that is added as an extension to the sheet of fabric 32.

In the Trendelenburg position, the force vector of the patient's weight is applied parallel to the direction of the sheet of fabric 32 that wraps around at least a portion of the foot end 10 of the section 12 of the surgical table mattress 30 or underbody support 16 that supports the patient's torso. In some embodiments, the anchoring mechanism of this invention, the foot end extension 58 of the sheet of fabric 32 that wraps around at least a portion of the foot end 10 of the section 12 of the surgical table mattress 30 or underbody support 16 that supports the patient's torso and is secured under the surgical table mattress 30 or underbody support 16, is applying a force vector that is directly opposite the direction of the force applied by the patient's weight when the patient is in the Trendelenburg position. The positive coupling provided by the foot end extension 58 of the sheet of fabric 32 that wraps around at least a portion of the foot end 10 of the section 12 of the surgical table mattress 30 or underbody support 16 that supports the patient's torso and is secured under the surgical table mattress 30 or underbody support 16 does not stretch or flex and therefore substantially limits (e.g., does not allow) slippage or deformation between the patient securement overlay 54 and the surgical table mattress 30 or underbody support 16. In some embodiments, the anchoring mechanism of this disclosure at the foot end 10 of the section 12 of the surgical table mattress 30 or underbody support 16 that supports the patient's torso, creates an anchoring force vector that is advantageously directly opposite the force vector of the patient sliding down the incline of the surgical table 4 in the Trendelenburg position. This is in contrast to known securement pads 26 where the anchoring force vector is sideways or perpendicular to the force vector of the patient sliding down the incline of the surgical table 4 in the Trendelenburg position. A perpendicular force vector to prevent sliding is not nearly as secure as a parallel force vector.

In some embodiments, the portion of the sheet of fabric 32 that wraps around at least a portion of the foot end 10 of the section 12 of the surgical table mattress 30 or underbody support 16 that supports the patient's torso is narrower than a width of the sheet of fabric 32. Advantageously, in some embodiments, the portion of the sheet of fabric 32 that wraps around at least a portion of the foot end 10 of the section 12 of the surgical table mattress 30 or underbody support 16 that supports the patient's torso is approximately as wide as the width of the base or closed side of the perineal cutout 14 at the foot end 10 of the section 12 of the surgical table mattress 30 or underbody support 16 that supports the patient's torso. The reinforced nature of the perineal cutout 14 provides a more secure anchoring location than the flat end of a surgical table mattress 30 or underbody support 16 without a perineal cutout 14 could provide. The side extensions 56 of a surgical table mattress 30 or underbody support 16 adjacent the sides of the perineal cutout 14 provide reinforcement to the perineal cutout 14 opposing the force vector of the patient sliding down the incline of the surgical table 4 in the Trendelenburg position.

In some embodiments, the foot end extension 58 and head end extension 60 of the sheet of fabric 32 for respectively wrapping around at least a portion of the foot end 10 and head end 62 of the surgical table mattress 30 or underbody support 16, includes one or more elements that improve the friction bond between the foot end extension 58 and head end extension 60 and either or both of the underside of the underbody support 16, the section 12 of the surgical table mattress 30 that supports the patient's torso and/or the surgical table top 64. In some embodiments, the one or more elements that improve this friction bond include a low tack adhesive or three-dimensional friction-enhancing elements, that can be plastic or rubber, applied to the foot end extension 58 and head end extension 60 of the sheet of fabric 32.

Any low tack adhesives known in the art can be used to improve this friction bond, including but not limited to those adhesives used on Post-it Notes® (3M Corporation), for example. Plastic or rubber three-dimensional friction-enhancing elements that can be used include but are not limited to: silicone, viscoelastic polyurethane foams, viscoelastic PVC foams, other viscoelastic polymeric foams, urethane, PVC, as well as other polymers and rubbers. The friction-enhancing elements 34, which can be three-dimensional friction-enhancing elements, may be applied to foot end extension 58 and head end extension 60 of the sheet of fabric 32, or may be a separate piece of fabric that is adhesively bonded, heat bonded, or sewn to the sheet of fabric 32 forming foot end extension 58 and head end extension 60.

Figure 16:
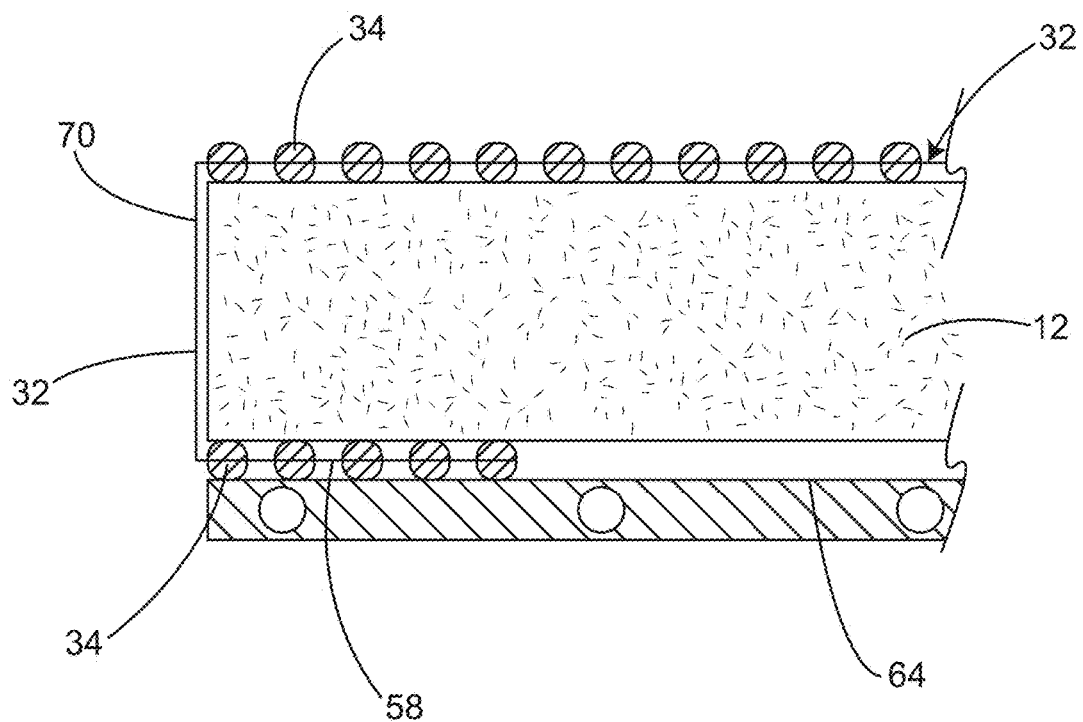
FIG. 16 is a longitudinal section view of a surgical table mattress with a sheet of fabric in accordance with illustrative embodiments.
Figure 17:
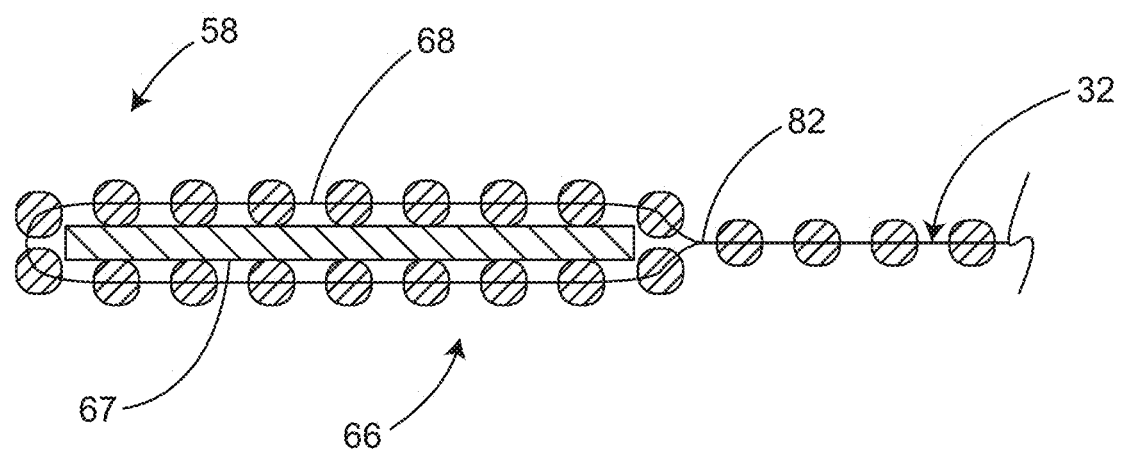
FIG. 17 is a longitudinal section view of an anchor in accordance with illustrative embodiments.

As shown in FIG. 16, in some embodiments the one or more elements that improve the friction bond between the sheet of fabric 32 or the foot end extension 58 and head end extension 60 and any or all of the underside of the underbody support 16, the surgical table mattress 30, and the surgical table top 64 include Velcro, snaps, or hooks. In some embodiments, as shown in FIG. 17, the foot end extension 58 at the foot end of the sheet of fabric 32 includes an anchor 66. In some cases, the anchor 66 is made of a flat and stiff material, such as a piece of plastic, metal, fiberboard or other suitable flat and stiff material. As defined herein, "stiff" refers to the ability of the anchor 66 to prevent deformation by a given force at room temperature, that is equal to or greater than the force necessary to deform a similar sized piece of low-density polyethylene (LDPE) that is 0.03125 inches thick (1/32 inches). The anchor 66 may be any size or shape. In some embodiments, the anchor 66 is a rectangular (or substantially rectangular) shape, between 2 and 8 inches long and between 4 and 20 inches wide. In some embodiments, the width of the anchor 66 corresponds to the width of the base or closed side of the perineal cutout 14 at the foot end 10 of the section 12 of the surgical table mattress 30 or underbody support 16 that supports the patient's torso.

Figure 18:
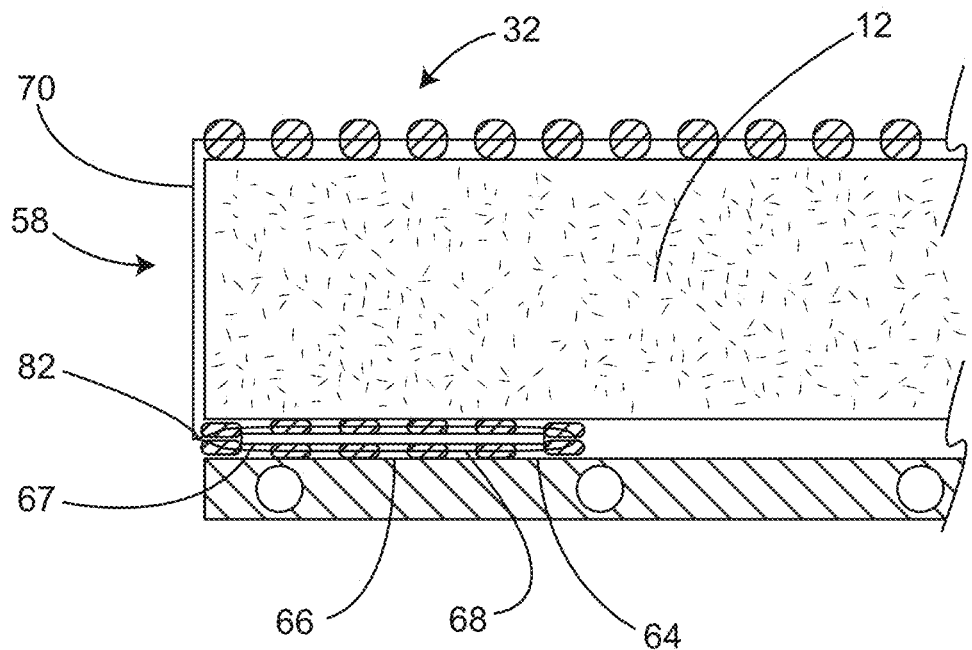
FIG. 18 is a longitudinal section view of a surgical table mattress with a sheet of fabric and an anchor in accordance with illustrative embodiments.

As shown in FIGS. 17 and 18, in some embodiments, the foot end extension 58 at the foot end of the sheet of fabric 32 includes the anchor 66. In some cases, the anchor 66 comprises one or more anchor plates 67 made of a flat and stiff material (e.g., plastic, metal, fiberboard, or other suitable materials). As defined herein, "stiff" refers to the ability of the anchor 66 to prevent deformation by a given force at room temperature, that is equal to or greater than the force necessary to deform a similar sized piece of low-density polyethylene (LDPE) that is 0.03125 inches thick (1/32 inches). The anchor plate 67 can be substantially rectangular or can have any other suitable shape. In some embodiments, the anchor plate 67 may be made of low-density polyethylene (LDPE) approximately 0.0625 inches thick (1/16 inches). In some embodiments, the anchor plate 67 may be attached to the foot end of the sheet of fabric 32 or foot end extension 58 by inserting it into a pouch 68 formed near the foot end to create anchor 66. The pouch 68 may be formed by folding the distal end of the sheet of fabric 32 or foot end extension 58 back on itself. Alternately, the pouch 68 may be formed by adding an additional piece of fabric to the distal end of the sheet of fabric 32 or foot end extension 58. In some embodiments, the pouch 68 may be formed by surrounding some or all of the perimeter of the anchor plate 67 with an RF seal, an ultrasound seal, a heat seal, an adhesive bond, or sewing to create a seal 82 between the two layers of the sheet of fabric 32 or foot end extension 58 covering the anchor plate 67 so as to thereby form pouch 68.

Figure 19:
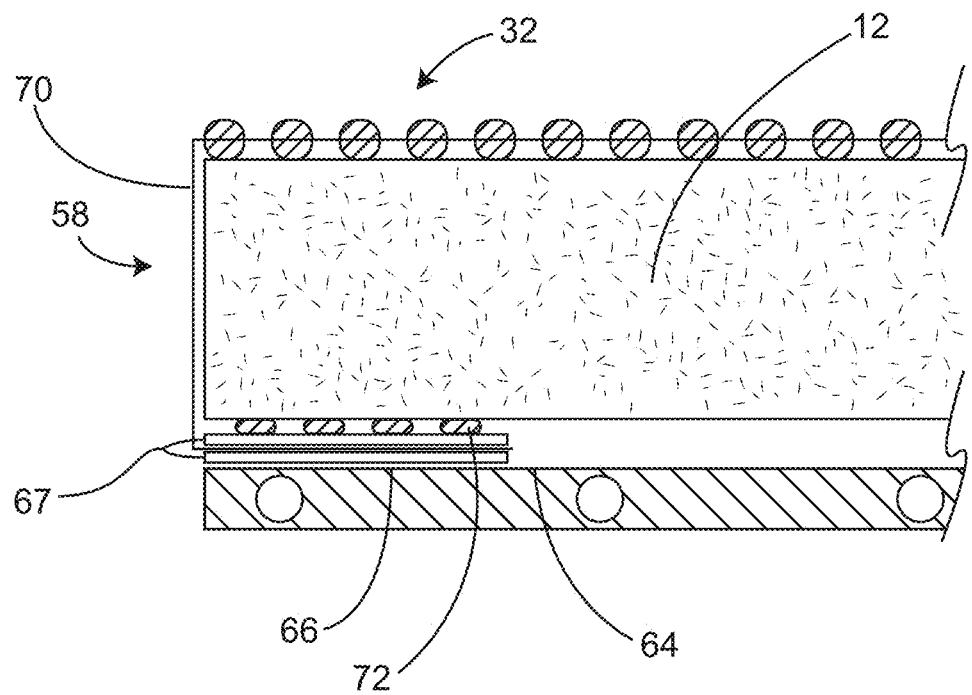
FIG. 19 is a longitudinal section view of a surgical table mattress with a sheet of fabric and an anchor in accordance with illustrative embodiments.

In some embodiments, as shown in FIG. 19, the anchor 66 may be created by attaching one or two anchor plates 67 to one or both sides of the distal end of the sheet of fabric 32 or foot end extension 58. The anchor plate 67 may be substantially rectangular or can have any other suitable shape. The anchor plate 67 can be made of plastic, metal, fiberboard, or other suitable material. The anchor plate 67 may further include friction-enhancing elements 72. The friction-enhancing elements 72 can comprise plastic or rubber, for example. The friction-enhancing elements 72 include but are not limited to: PVC foams, viscoelastic PVC foams, silicone, viscoelastic polyurethane foams, other viscoelastic polymeric foams, urethane, PVC, as well as other polymers and rubbers. The one or two anchor plates 67 (that can, for example, comprise plastic, metal or fiberboard) may be attached to one or both sides of the distal end of the sheet of fabric 32 or foot end extension 58 by sewing, adhesive bonds, thermal and RF welds, rivets, staples, Velcro, or other suitable attachments.

In some embodiments, as shown in FIG. 18, the anchor 66 (which may be flat and stiff) can be inserted between the bottom of the surgical table mattress 30 and the surgical table top 64 or between the underbody support 16 and the surgical table mattress 30. The weight of the patient's buttocks resting on the foot end 10 of the underbody support 16 or section 12 of the surgical table mattress 30 that supports the patient's torso, positively captures the anchor 66 between the surgical table mattress 30 and the underbody support 16 or the surgical table mattress 30 and the surgical table top 64. The stiffness of the anchor 66 prevents the upward force of the sheet of fabric 32 or foot end extension 58 at the foot end of the surgical table mattress 30 or underbody support 16 from elevating the end of the surgical table mattress 30 or underbody support 16, or dislodging the anchor 66 from under the surgical table mattress 30 or underbody support 16. The anchor 66 of the present disclosure is very easy to use and yet very secure.

In some embodiments, the sheet of fabric 32 or the foot end extension 58 at the foot end of the sheet of fabric 32 that joins the foot end of the sheet of fabric 32 to the anchor 66 (which can be plastic or metal), is adjustable in length to accommodate surgical table mattresses 30 of different thicknesses. Surgical table mattresses 30 are typically 2-4 inches thick. As shown in FIG. 18, the neck 70 of the sheet of fabric 32 or the foot end extension 58 at the foot end of the sheet of fabric 32 that joins the foot end of the sheet of fabric 32 to the pouch 68 containing the anchor plate 67 (which can be or comprise plastic or metal) may be advantageously manufactured in different lengths to accommodate surgical table mattresses 30 of different thicknesses. For example, a neck 70 that is two inches may be supplied to customers with surgical table mattresses 30 that are 2 inches thick, while a neck 70 that is four inches may be supplied to customers with surgical table mattresses 30 that are 4 inches thick.

Figure 20A:
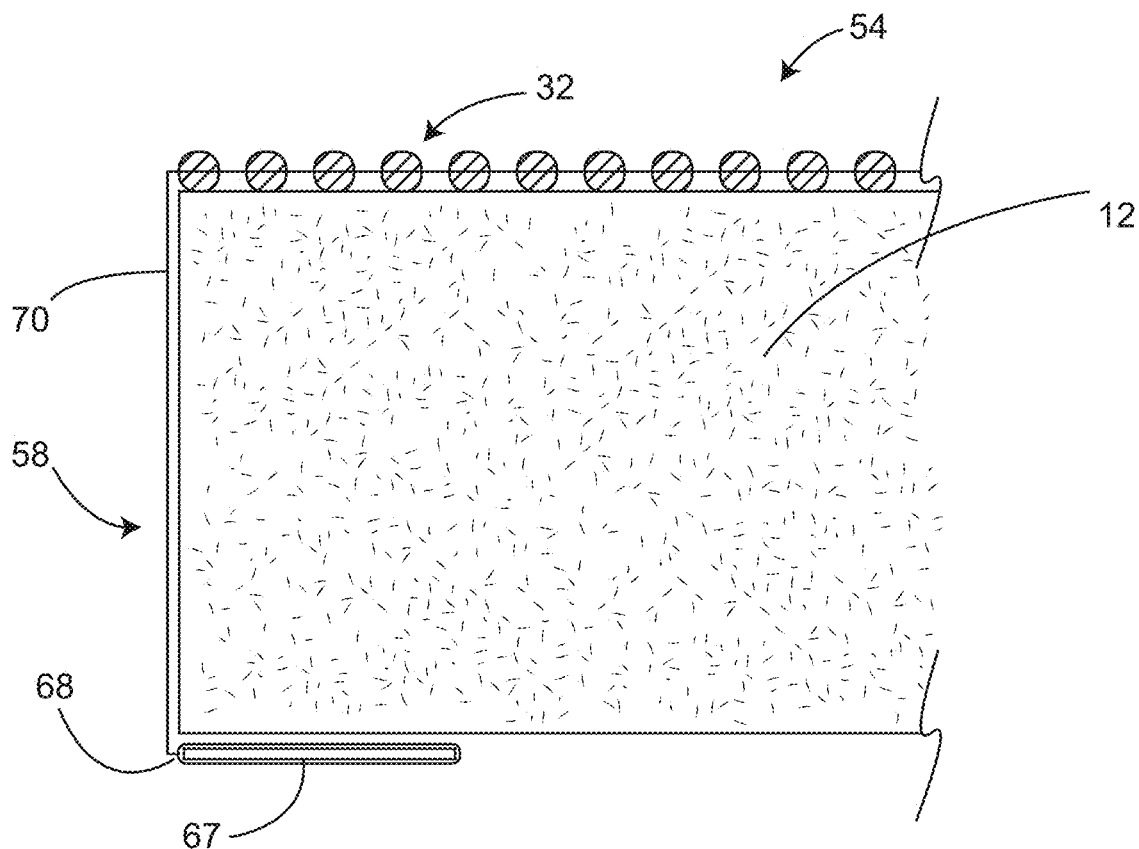
FIG. 20A is a longitudinal section view of a surgical table mattress with a sheet of fabric and an anchor in accordance with illustrative embodiments.
Figure 20B:
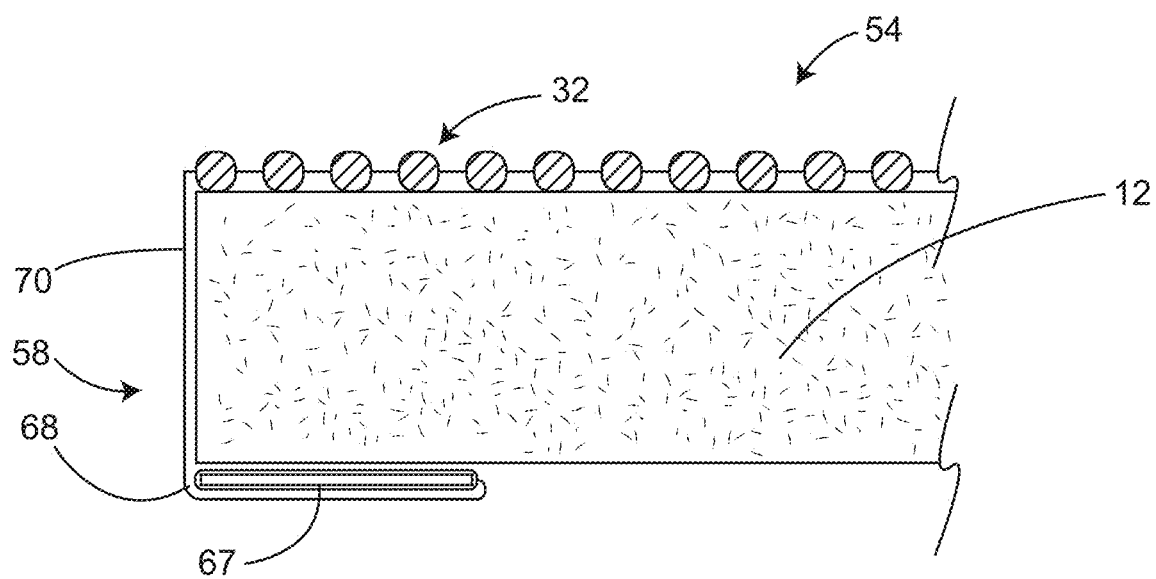
FIG. 20B is a longitudinal section view of a surgical table mattress with a sheet of fabric and an anchor in accordance with illustrative embodiments.
Figure 20C:
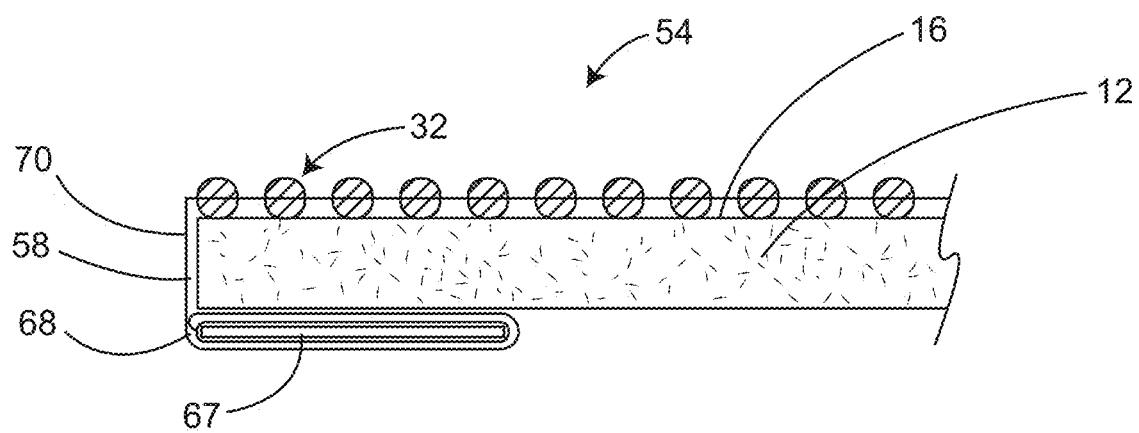
FIG. 20C is a longitudinal section view of a surgical table mattress with a sheet of fabric and an anchor in accordance with illustrative embodiments.

In some embodiments, as shown in FIG. 20A, the neck 70 of the sheet of fabric 32 or the foot end extension 58 at the foot end of the sheet of fabric 32 that joins the foot end of the sheet of fabric 32 to the pouch 68 containing the anchor plate 67 (which can comprise plastic or metal), may be made 3-6 inches long to accommodate even the thickest of surgical table mattresses 30. In some embodiments, for example as shown in FIG. 20B, a neck 70 that is five inches long may be shortened two inches by the user to accommodate surgical table mattresses 30 that are in a range of between two and three inches thick, by conveniently wrapping a two inch long anchor 66 back on itself with a half-wrap before inserting the anchor 66 under the surgical table mattress 30. In this example, a half wrap shortens the neck 70 by approximately 2 inches. In this same example, as shown in FIG. 20C, if the 2 inch long anchor 66 is wrapped back on itself with a full wrap, the neck 70 that is five inches long may be shortened approximately four inches by the user to accommodate a surgical table mattress 30 or underbody support 16 that is about one inch thick. In some embodiments, a single size of the patient securement overlay 54 can accommodate surgical table mattresses 30 or underbody supports 16 of various thicknesses.

Figure 21:
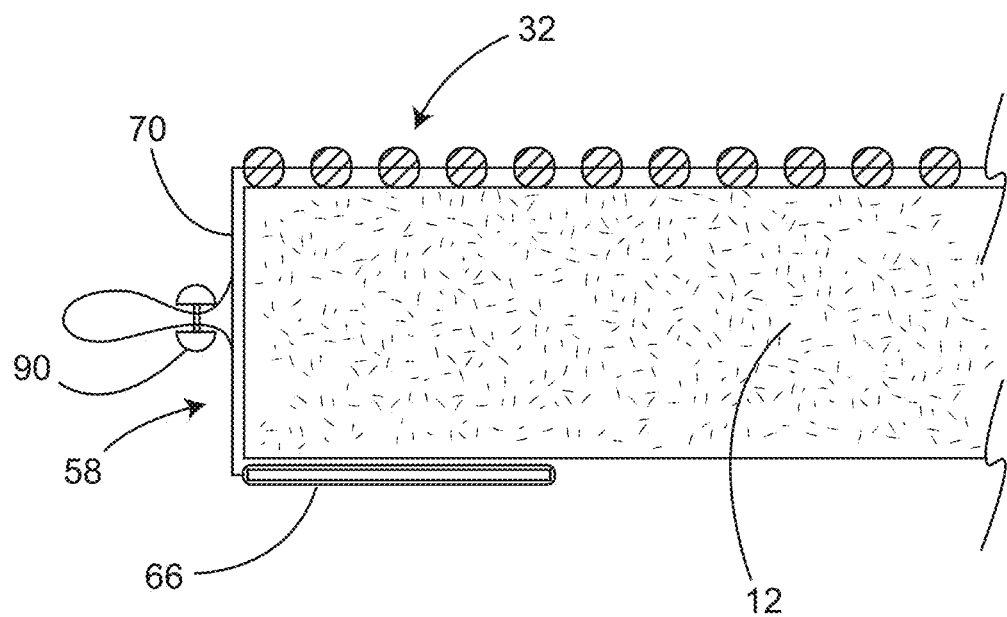
FIG. 21 is a longitudinal section view of a surgical table mattress with a sheet of fabric and an anchor in accordance with illustrative embodiments.

In some embodiments, as shown in FIG. 21, the neck 70 of the sheet of fabric 32 or the foot end extension 58 at the foot end of the sheet of fabric 32 that joins the foot end of the sheet of fabric 32 to the anchor 66, may be adjustably shortened using adjustable fasteners 90 such as snaps, buttons, Velcro, hooks, buckles and straps. Other adjustable fasteners 90 are anticipated. The adjustable fasteners 90 may be used to shorten, gather and retain excess material in the neck 70 of the foot end extension 58 in order to shorten the neck 70 to match the thickness of a given surgical table mattress 30 or underbody support 16, allowing a single design to work effectively on a surgical table mattress 30 or underbody support 16 having any thickness.

In some embodiments, the neck 70 of the sheet of fabric 32 or the foot end extension 58 at the foot end of the sheet of fabric 32 that joins the foot end of the sheet of fabric 32 to the anchor 66 (which can be plastic, metal, fiberboard, or other suitable materials) may be strengthened by melting and compressing the friction-enhancing elements, such as PVC foams, viscoelastic PVC foams, viscoelastic polyurethane foams, or polyurethane foams into the form of a film. Compressing these materials in a heated press or RF press will collapse the foam structure and convert the material to resemble a film. The film-like structure is stronger than the foam structure and may, in some applications, be a superior configuration for wrapping around the end of the surgical table mattress 30 or underbody support 16.

In some embodiments, as shown in FIG. 15, the layer of flexible foam material 52 may be adhesively laminated to the upper surface 36 of the sheet of fabric 32. Laminating the layer of flexible foam material 52 to the sheet of fabric 32 advantageously utilizes the positive, non-slip anchoring of the sheet of fabric 32 or foot end extension 58 wrapping around the foot end 10 of the section 12 of the surgical table mattress 30 or underbody support 16 that supports the patient's torso, positively capturing the sheet of fabric 32 or foot end extension 58 between the underbody support 16 and the surgical table mattress 30 or the surgical table mattress 30 and the surgical table top 64. When the sheet of fabric 32 is positively anchored, the layer of flexible foam material 52 is also positively anchored (e.g., laminated to the upper surface of the sheet of fabric 32). This is in contrast to known pad straps 28A, 28B that anchor a layer of flexible foam material to the side rails 20 of the surgical table 4, as shown in FIG. 6. The sheet of fabric 32 also strengthens the layer of flexible foam material 52, allowing the layer of flexible foam material 52 to be relatively thin, for example from 0.25-0.75 inches thick. The sheet of fabric 32 prevents the layer of flexible foam material 52 from tearing, stretching or deforming under the weight of a patient that is in the Trendelenburg position.

In some embodiments, the layer of flexible foam material 52 may be any type of suitable foam material. In some embodiments, the layer of flexible foam material 52 may be a viscoelastic urethane foam or a urethane upholstery foam. Other foam materials including other viscoelastic foam materials are anticipated and can be used as the layer of flexible foam material 52. The layer of flexible foam material 52 may have any thickness between about 0.25 inches and about 3 inches. In some embodiments, the layer of flexible foam material 52 can be less than 0.5 inches thick.

Figure 22:
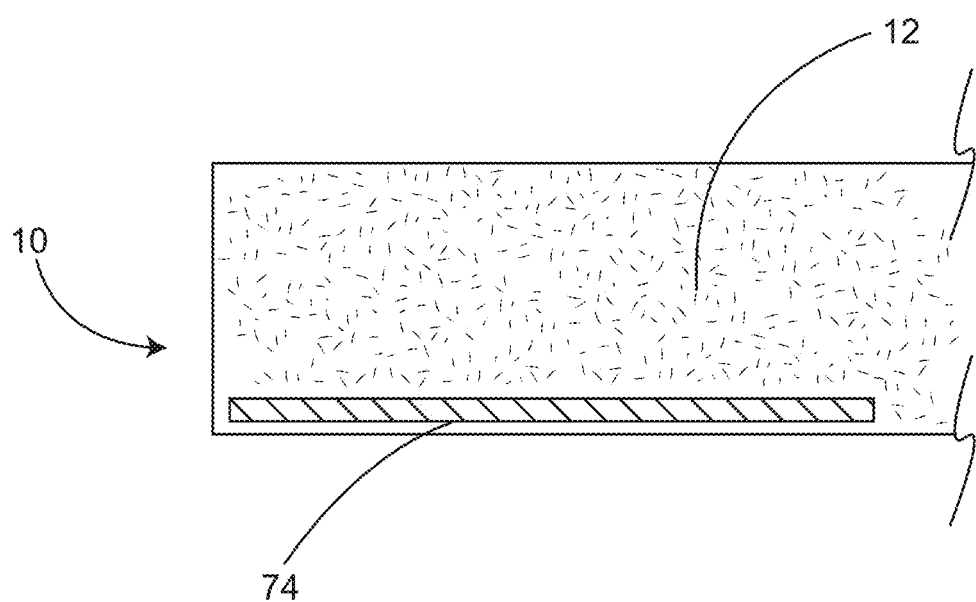
FIG. 22 is a longitudinal section view of a surgical table mattress in accordance with illustrative embodiments.

In some embodiments, as shown in FIG. 22, at least a portion of the bottom of the surgical table mattress 30 or underbody support 16 may be reinforced with a plate 74. The plate 74 can be a stiff or relatively stiff plate, and can be made of plastic, metal, wood, fiberboard, or other suitable stiffener. With regards to plate 74, "stiff" is defined herein as the ability to resist deformation of more than one inch, when a plate the width of a surgical mattress extends outward twelve inches beyond the edge of a table surface and five pounds of weight are applied to the unsupported distal edge. The plate 74 may be located under the surgical table mattress's foam pad, inside the protective cover of surgical table mattress 30. The plate 74 stabilizes the lower corner of the surgical table mattress 30 at the foot end 10 and may be particularly advantageous when used in conjunction with the patient securement overlay 54 of the present disclosure. When the patient's weight is supported by the surgical table mattress 30, the plate 74 stabilizes the lower corner of the surgical table mattress 30 at the foot end 10 so that it cannot bend or compress either upward or toward the head end, in response to an upward pulling force applied from the foot end extension 58 at the foot end of the sheet of fabric 32 that may be tucked under the foot end of the surgical table mattress 30.

In some embodiments, the plate 74 improves the anchoring security of the foot end extension 58 at the foot end of the sheet of fabric 32 when it is tucked under the foot end of the surgical table mattress 30. In some embodiments, the plate 74 also prevents the surgical table mattress 30, when comprised of foam, from compressing at the foot end 10. Compressing the foot end 10 of the surgical table mattress 30 toward the head end, when the sheet of fabric 32 or foot end extension 58 is wrapped around the foot end 10, can allow about 1-3 inches of patient displacement down the decline toward the head end of the surgical table 4 in the steep Trendelenburg position.

In some embodiments, the plate 74 may approximate the size of the section 12 of the surgical table mattress 30 that supports the patient's torso. In some embodiments, the plate 74 may be limited to an area within about 10-24 inches of the foot end 10 and approximate the width of the foot end 10 of the section 12 of the surgical table mattress 30 that supports the patient's torso. Other sizes for the plate 74 are also anticipated and within the scope of the present disclosure.

In some embodiments, a method of supporting and restricting a sliding motion of a patient 2 on a surgical table 4 is provided. The method can include the steps of: (i) providing an underbody support 16 configured to support the patient 2 on the surgical table 4, the underbody support 16 including a compressible material layer having an upper surface configured to face the patient 2 opposite a base layer having a lower surface configured to face the surgical table 4; (ii) coupling the underbody support 16 to the surgical table 4; (iii) placing a sheet of fabric 32 between the upper surface of the underbody support 16 and the patient 2, the sheet of fabric 32 comprising friction-enhancing elements 34 on one or both sides of the sheet of fabric 32, wherein the sheet of fabric 32 is configured to grip both the underbody support 16 and the patient 2 to prevent the patient from inadvertently slipping off of the underbody support 16; and (iv) positioning the patient 2 on the underbody support 16.

Figure 23:
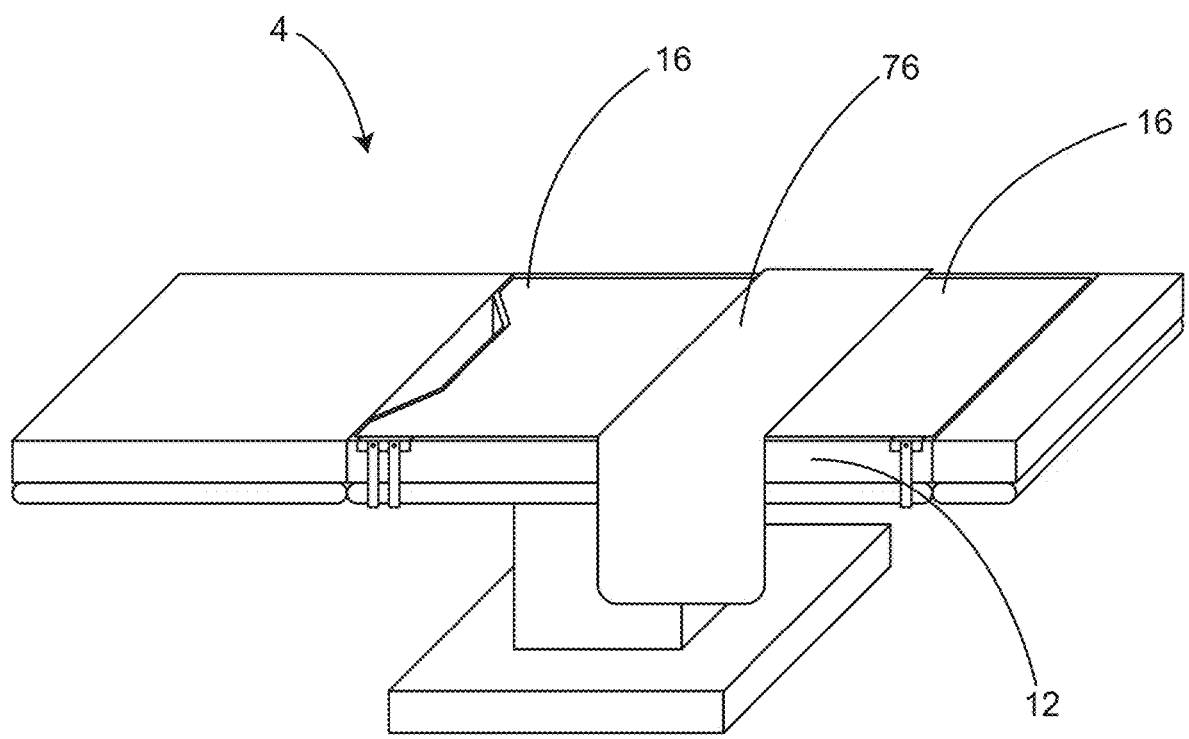
FIG. 23 is a perspective view of a draw sheet over an underbody support attached to a surgical table in accordance with illustrative embodiments.

In some embodiments, as shown in FIG. 23, a draw sheet 76 may be positioned over the underbody support 16 for lifting the patient 2 (not shown). A draw sheet 76 is an elongated sheet of fabric that is positioned across the surgical table 4 from side to side, located substantially underneath a torso of the patient 2. The ends of the draw sheet 76 extend out to each side of the patient 2 and allow surgical staff to lift the patient 2 from the surgical table 4 to the gurney while avoiding injuries to the patient or staff. Known draw sheets include a bed sheet that has been folded the long way into a long and narrow sheet that is between about 18 and 36 inches wide and between about 6-7 feet long. Draw sheets 76 can be disposable and can be made from either woven or nonwoven fabrics. In some embodiments, draw sheets 76 that are disposable can be used and may be between 60 and 84 inches long and between 12 and 36 inches wide.

It will be appreciated by skilled artisans that a sheet of fabric placed on top of any patient securement device, between the patient securement device and the patient, may reduce the effectiveness of the patient securement device. One reason for this is that tightly woven fabrics, such as woven cotton or polyester, may slip against the securement device. To address this limitation of known draw sheets, in some embodiments, the draw sheet 76 of the present disclosure may advantageously be made of nonwoven fabrics including but not limited to polyester fibers. Nonwoven fabrics with relatively loose fibers may interact with securement pads 26 (e.g., foam securement pads) or the friction-enhancing elements 34 of the present disclosure to produce a relatively nonslip interface as compared to woven fabrics.

In some embodiments, nonwoven fabrics may be selected to use for the draw sheet 76 because they are very strong if the fibers are oriented primarily in the long axis of the draw sheet 76, the axis lifting the weight of the patient, while also being disposable. Additionally, in some embodiments, the non-woven fibers of the draw sheet 76 are similar to the loop portion of Velcro hook and loop fasteners. The tucked ends of the draw sheet 76 made of non-woven fibers may be positively secured to Velcro hook material that is attached to the underside of the underbody support 16 or the underside of the surgical table mattress 30 or the underside of a base sheet 106 (e.g., sheet of fabric or film). When the ends of the draw sheet 76 are tucked under the underbody support 16 or the underside of the surgical table mattress 30 or the underside of the base sheet 106, the positive connection between the Velcro hooks and the draw sheet 76, which is a non-woven draw sheet in this example, prevents the draw sheet 76 from pulling out and becoming un-tucked. This arrangement creates a very secure and reliable support for the tucked arms of the patient.

Figure 24:
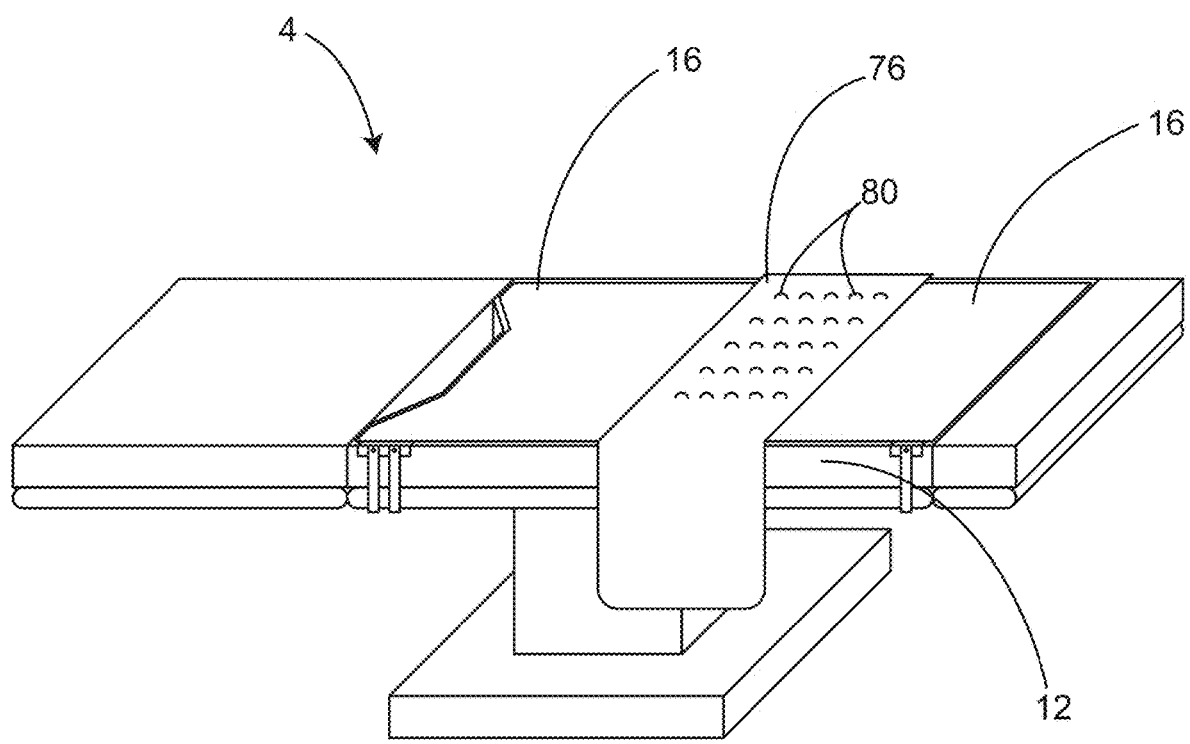
FIG. 24 is a perspective view of a draw sheet over an underbody support attached to a surgical table in accordance with illustrative embodiments.

In some embodiments, as shown in FIG. 24, the draw sheet 76 includes friction-enhancing elements 80. The friction-enhancing elements 80 can be three-dimensional friction-enhancing elements and can be (or comprise) plastic or rubber. The friction-enhancing elements 80 include but are not limited to: PVC foams, viscoelastic PVC foams, silicone, viscoelastic polyurethane foams, other viscoelastic polymeric foams, urethane, PVC, as well as other polymers and rubbers. The friction-enhancing elements 80 may be applied only to a top surface of the draw sheet 76 or may be applied only to a bottom surface of the draw sheet 76 or may be applied to both the top and bottom surfaces of the draw sheet 76. The friction-enhancing elements 80 on the upper surface of the draw sheet 76 may be located near the center of the draw sheet 76, in a location that will most likely contact a back of the patient 2. The friction-enhancing elements 80 applied in a central area of the top surface of the draw sheet 76 corresponding to a location of the patient's back, may provide a similar coefficient of friction between the draw sheet 76 and the patient's back as would have been provided by the sheet of fabric 32 and the patient's back, had the draw sheet 76 not been interposed.

The friction-enhancing elements 80 may be applied to the upper and/or lower surfaces of the draw sheet 76, between the ends 78 of the draw sheet 76 and the central region contacting the patient. The friction-enhancing elements 80 applied between the ends 78 of the draw sheet 76 and the central region contacting the patient, increase the coefficient of friction between the draw sheet 76 and the surgical table mattress 30, the underbody support 16, or the surgical table top 64. Adding the friction-enhancing elements 80 to the ends 78 of the draw sheet 76 substantially increases the force required to pull the ends 78 of the draw sheet 76, when tucked, out from between the surgical table mattress 30, the underbody support 16, or the surgical table top 64. The friction-enhancing elements 80 applied between the ends 78 of the draw sheet 76 and the central region contacting the patient, help to prevent the ends 78 of the draw sheet 76 from inadvertently pulling out from between the surgical table mattress 30, the underbody support 16, or the surgical table top 64, to help prevent the patient's arms from dropping and becoming injured.

Figure 25:
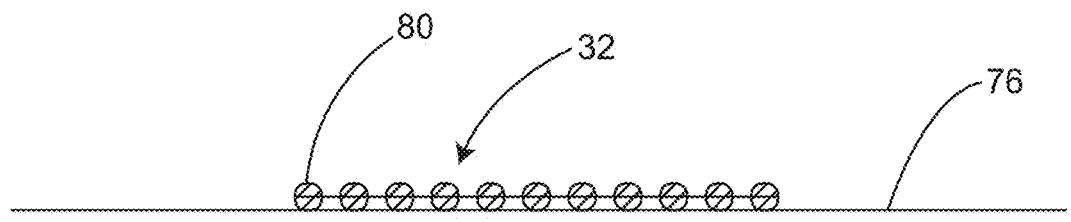
FIG. 25 is a longitudinal section view of a draw sheet in accordance with illustrative embodiments.

In some embodiments, as shown in FIG. 25, the draw sheet 76 includes a small piece of the sheet of fabric 32 material previously described, that includes the friction-enhancing elements 34 that can be three-dimensional friction-enhancing elements. The small piece of the sheet of fabric 32 material may be about 24 inches square, for example, and may be attached to the central area of the top surface of the draw sheet 76 by an RF seal, heat seal, sewing, or adhesive attachment. Other sizes and shapes of the small piece of the sheet of fabric 32 material attached to the draw sheet 76 are anticipated. The friction-enhancing elements 80 on the top of the draw sheet 76 engage the patient's back in the same manner as the friction-enhancing elements 34 on the sheet of fabric 32. Therefore, effectiveness of the securement by the sheet of fabric 32 is not adversely affected by interposing the draw sheet 76 of the instant disclosure between the sheet of fabric 32 or any other known securement pad 26, and the patient's back.

Attaching the small piece of the sheet of fabric 32 with friction-enhancing elements 34, which can be three-dimensional friction-enhancing elements, to the draw sheet 76, allows the draw sheet 76 to be a strong, non-stretching non-woven fabric material capable of lifting a patient weighing up to 300 pounds. At the same time, a small piece of the sheet of fabric 32 with friction-enhancing elements 34 that can be three-dimensional friction-enhancing elements may advantageously be made of a scrim material for optimal formation of the friction-enhancing elements 34 and yet the weaker scrim material is not required to lift the weight of the patient. This combination optimizes the strengths of each material and complements the weaknesses of each material.

The small piece of the sheet of fabric 32 material attached to the upper surface of the draw sheet 76 also helps to stabilize draw sheet 76 under the patient. This prevents the sides of the draw sheet 76, from bunching up and narrowing the draw sheet 76, in response to the patient lying on the draw sheet 76.

Figure 26:
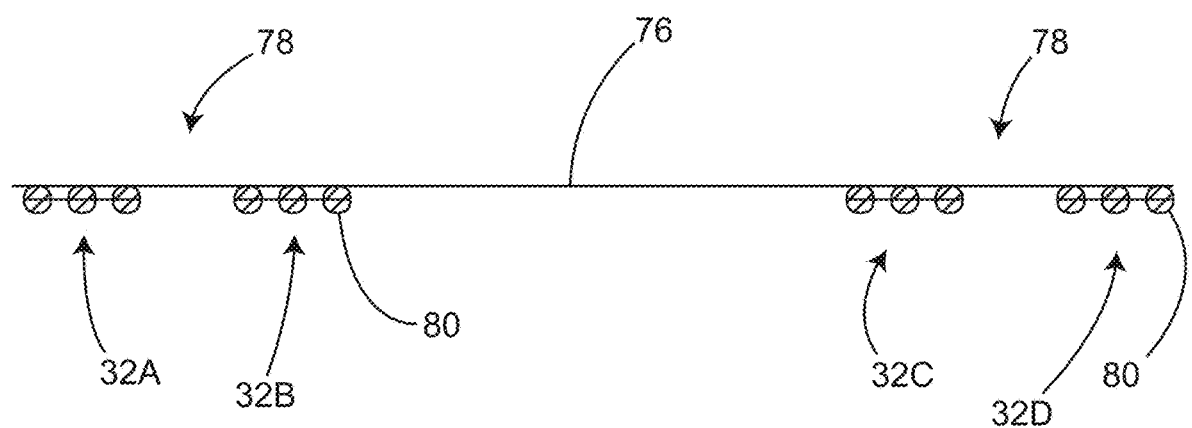
FIG. 26 is a longitudinal section view of a draw sheet in accordance with illustrative embodiments.

In some embodiments, as shown in FIG. 26, pieces of the sheet of fabric 32 material may be attached to the upper and/or lower surfaces of the draw sheet 76, between the ends 78 of the draw sheet 76 and the central region contacting the patient to provide friction-enhancing elements 80 that can be three-dimensional friction-enhancing elements. In some cases, each piece of sheet of fabric 32 is shown individually in the drawings as 32A, 32B, 32C, and 32D. The pieces of the sheet of fabric 32 material may be strips that are between about 0.5 and about 2 inches wide and reach substantially from one edge to another edge of draw sheet 76. The pieces of the sheet of fabric 32 material may be attached to the draw sheet 76 by RF sealing, heat sealing, sewing, or adhesive attachment. Other sizes and shapes of the pieces of the sheet of fabric 32 material are anticipated. Adding friction-enhancing elements 80, which can be three-dimensional friction-enhancing elements, to the ends 78 of the draw sheet 76 substantially increases the force required to pull the ends 78 of the draw sheet 76, when tucked, out from between surgical table mattress 30, the underbody support 16, or the surgical table top 64.

Figure 27:
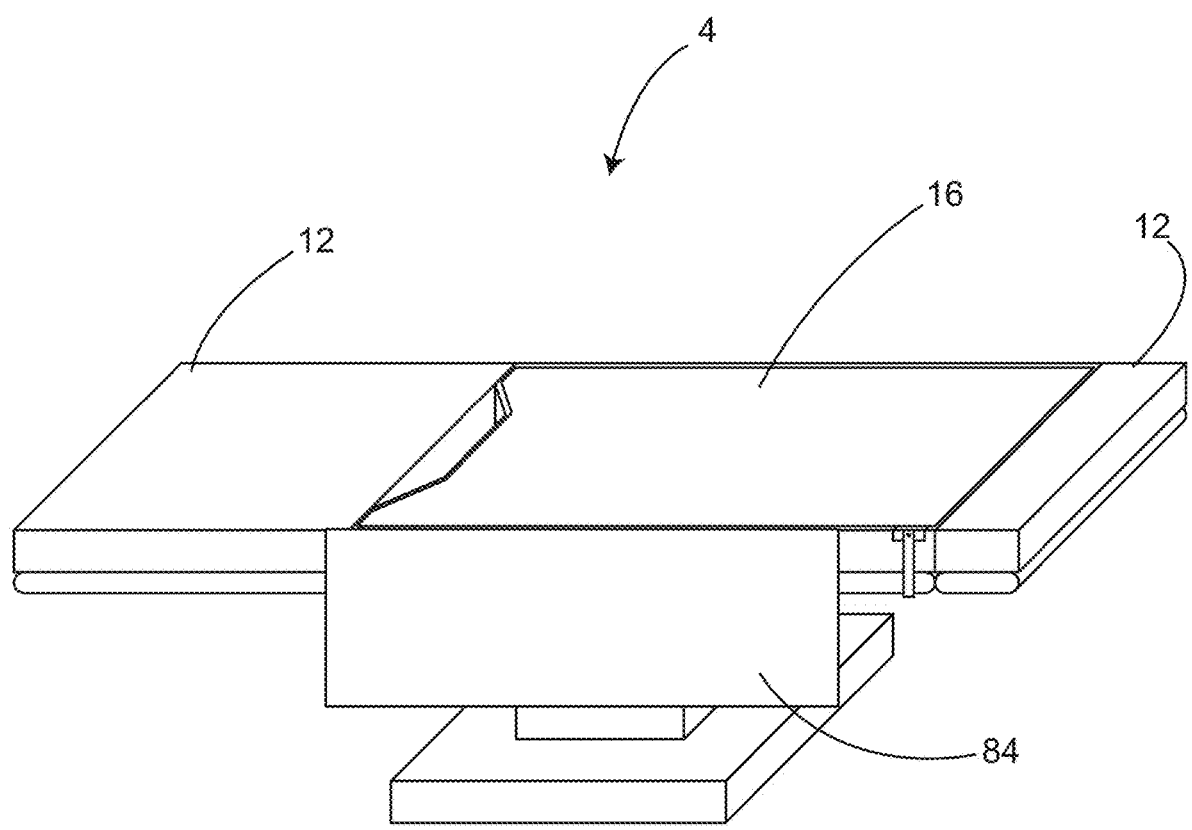
FIG. 27 is a perspective view of an underbody support with arm-securing flaps attached to a surgical table in accordance with illustrative embodiments.

In some embodiments, as shown in FIG. 27, lateral extensions in the form of arm-securing flaps 84 may be added to the underbody support 16 or section 12 of the surgical table mattress 30 that supports the patient's torso, to help support and retain the patient's arms when they are tucked by the sides of the patient. In some cases, the arm-securing flaps 84 are shown individually in the drawings as reference numerals 84A and 84B. The "arms tucked" position is very common during surgical procedures performed in the Trendelenburg position. The arm-securing flaps 84 may advantageously be removably attached to the side edges of the underbody support 16 or section 12 of the surgical table mattress 30 that supports the patient's torso. In some embodiments, the arm-securing flaps 84 may be permanently attached to the sides of the underbody support 16.

The "arms tucked" position is very common during surgical procedures that may not be performed in the Trendelenburg position such as cardiac surgery. In certain procedures, for example robotic cardiac surgery, the surgical table 4 may be tilted to one side or the other (as opposed to one end or the other as in the Trendelenburg or reverse Trendelenburg position). This may be called a lateral tilt position. In the lateral tilt position, the patient 2 may be at risk for sliding sideways off of the surgical table 4. In some embodiments, the sheet of fabric 32 may be used to prevent the patient 2 from sliding sideways off of the surgical table 4. The sheet of fabric 32 prevents sideways sliding identically to how it prevents longitudinal sliding previously described for the Trendelenburg position.

In the lateral tilt position, the patient 2 may be at risk for rolling sideways off of the surgical table 4. In some embodiments, the arm-securing flaps 84 may be used to prevent the patient from rolling sideways off of the surgical table 4. The arm-securing flaps 84 are secured either to or under the underbody support 16 and the underbody support 16 that is secured to the surgical table 4. Therefore, the arm-securing flaps 84 are indirectly but positively anchored to the surgical table. When the arm-securing flaps 84 are wrapped around the patient's arms 94, especially up into the armpit near the shoulder, and held in place by the draw sheet 76, the arm-securing flaps 84 positively prevent the patient 2 from rolling sideways off of the surgical table 4. Using the arm-securing flaps 84 to prevent rolling advantageously utilizes the fact that the arms are the most lateral or most outbound attachment point on the patient's body 2 and thus have the most advantageous mechanical leverage to prevent rolling. This design and method of preventing sideways rolling uniquely obviates the need for safety straps placed across the patient's chest. Obviously, safety straps across the patient's chest cannot be utilized during cardiac and thoracic surgery and thus securing the patient to the surgical table 4 with the arm-securing flaps 84 is particularly advantageous during these procedures. Preventing sideways rolling by the arm-securing flaps 84 for other surgical procedures is also anticipated.

In some embodiments, the arm-securing flaps 84 may be made of the same material and generally the same construction as the underbody support 16 previously discussed in this disclosure. In some embodiments, the arm-securing flaps 84 may be between about 18 and about 36 inches long and extend out from the sides of the underbody support 16 between about 10 and about 24 inches. The arm-securing flaps 84 may be generally rectangular in shape or may be stylized. For example, the arm-securing flaps 84 may taper from wide at the upper arm to narrow at the hand.

In some embodiments, the arm-securing flaps 84 may be heated. The arm-securing flaps 84 may be heated blankets as disclosed in U.S. Pat. No. 8,772,676, which is incorporated by reference into this disclosure in its entirety. When the arm-securing flaps 84 are heated, they may be made by enclosing a flexible sheet-like heating element in a waterproof shell made of plastic film. The shell covers the heating element and includes two sheets of flexible plastic film material that are welded together about the edges of the heating element. The shell may also cover one or more layers of thermal insulation and one or more layers of foam padding or other protective materials. When the arm-securing flaps 84 are heated, they take advantage of the available skin surface of the arms (each arm is ~9% of the body surface area) in order to allow more heat transfer to the patient preventing or treating hypothermia. In addition to delivering heat to the patient by heating their arms and hands, heat to the arms and hands causes vasodilatation, improving blood flow and thus IV flow. Increased blood flow also improves the accuracy of the pulse oxymeter and any intravascular monitoring devices such as arterial lines.

Figure 28:
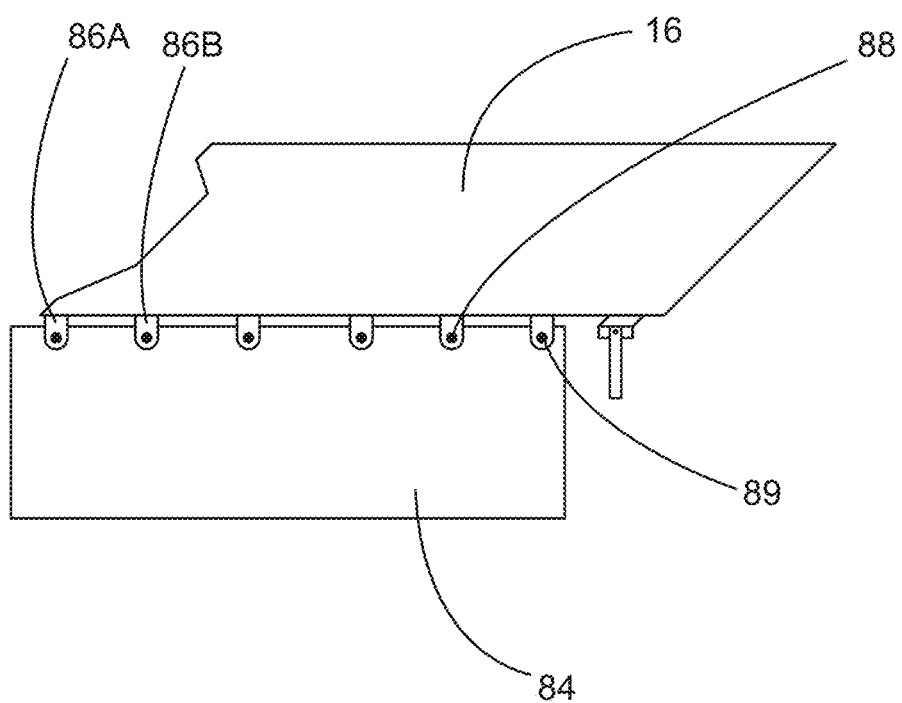
FIG. 28 is a perspective view of an underbody support with arm-securing flaps in accordance with illustrative embodiments.

In some embodiments, as shown in FIG. 28, the arm-securing flaps 84 may be removably attached to the side edges of the underbody support 16 or section 12 of the surgical table mattress 30 that supports the patient's torso. The arm-securing flaps 84 may have two or more attachment points, such as tabs 86, for securing the edge of each arm-securing flap 84 to the edge of the underbody support 16. In some cases, the tabs 86 are shown individually in the drawings as reference numerals 86A and 86B. In some embodiments, the arm-securing flaps 84 may have multiple attachment points such as tabs 86 for securing the edges of the arm-securing flaps 84 to the edges of the underbody support 16. Multiple attachment points allow adjustability of the relative positioning of the arm-securing flap 84 compared to the underbody support 16 depending on which attachment points are matched up with each other. For example, a short patient or a patient with very long arms may have the arm-securing flaps 84 attached to tabs 86 that are closer to the foot end or may even extend past the foot end of the underbody support 16 or section 12 of the surgical table mattress 30 that supports the patient's torso. Tall patients or patients with very long trunks, may have the arm-securing flaps 84 attached to tabs that are closer to the head end of the underbody support 16 or section 12 of the surgical table mattress 30 that supports the patient's torso. In some embodiments, the arm-securing flaps 84 may be permanently secured to the edge of the underbody support 16.

The attachment points may be tabs 86 or flaps made from shell material that extends outward from the peripheral bond of the shell. These attachment points or flaps may be fiber-reinforced, for example with a nylon mesh, for added strength. The tabs 86 or flaps may include button holes 88 on the arm-securing flaps 84 or the underbody support 16 and corresponding buttons 89 that are alignable with the button holes 88. The tabs 86 or flaps may include Velcro hooks on the arm-securing flaps 84 or the underbody support 16 and correlating Velcro loops that align with the hooks. Straps, snaps, barbs, ties or other fasteners are anticipated. Fasteners such as buttons and snaps that have an appreciable thickness, may advantageously be positioned with the button facing the surgical table mattress 30 rather than the patient.

In some embodiments, there are multiple attachment points, which can be tabs 86, for securing the edges of the arm-securing flaps 84 to the edges of the underbody support 16. In this case, the position of the arm-securing flaps 84 relative to the edges of the underbody support 16 is adjustable to accommodate different heights and arm lengths of patients and their relative position on the surgical table 4. The arm-securing flaps 84 may be secured to any part of the edge of the underbody support 16 and may be moved as needed to accommodate the next patient. In some embodiments, the arm-securing flaps 84 are attached to and not removable from the underbody support 16.

Figure 29:
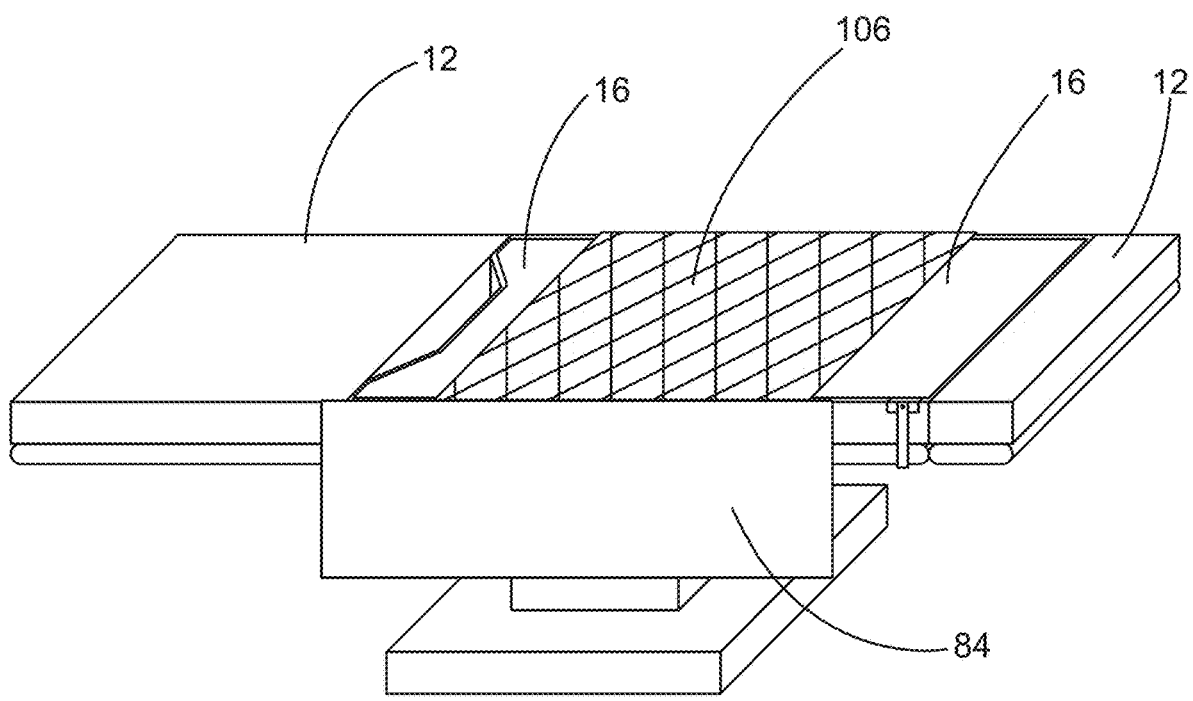
FIG. 29 is a perspective view of an underbody support with arm-securing flaps attached to a surgical table in accordance with illustrative embodiments.

In some embodiments, as shown in FIG. 29, the arm-securing flaps 84 may be secured to the side edges of a base sheet 106 (e.g., sheet of fabric or film) that approximates the width of the surgical tabletop 4. The base sheet 106 may be positioned under or over the surgical table mattress 30 or underbody support 16 and extend substantially from one side to the other side of the surgical table 4. The arm-securing flaps 84 may be secured to the edges of the base sheet 106 with the same fasteners as disclosed above for removably attaching the arm-securing flaps 84 to the surgical table mattress 30 or underbody support 16, including but not limited to buttons, Velcro, straps, snaps, barbs, or ties.

In some embodiments, the arm-securing flaps 84 may be permanently attached to the sides of the base sheet 106 much like saddlebags on a horse. The permanent attachment may be accomplished by RF sealing, heat or ultrasound sealing, sewing, or adhesive bonding of the arm-securing flaps 84 to the side edges of the base sheet 106. In some embodiments, the base sheet 106 may include a fiber reinforcement in the plastic film, with fibers such as nylon for added strength.

Figure 30:
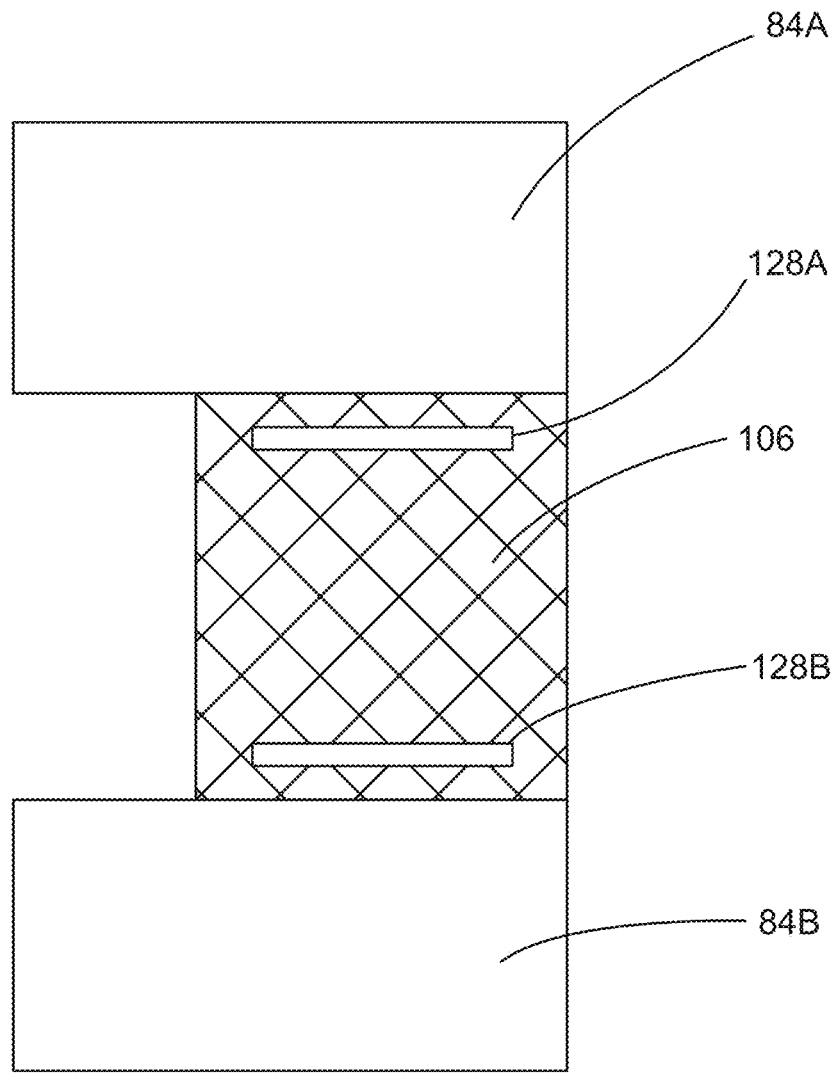
FIG. 30 is a top view of arm-securing flaps with a base sheet of fabric or film in accordance with illustrative embodiments.

In some embodiments, as shown in FIG. 30, the base sheet 106 is made of one or more layers of urethane or PVC film. In some embodiments, the arm-securing flaps 84 may be attached to each side of the base sheet 106 such that their proximal sides are proximate the side edges of the surgical table mattress 30 or underbody support 16. A second layer of film may be attached to some or all of the base sheet 106, creating an enclosed space or bridge traversing from one arm-securing flap 84 across the surgical table to the other arm-securing flap 84. In some embodiments, wires may traverse through this space to connect the heater of one arm-securing flap 84 to the heater of the other arm-securing flap 84. This connection allows a single plugin to conveniently activate both heaters. This connection also allows a single controller to control and power both heaters.

In some embodiments, the shell material of the arm-securing flaps 84 and the base sheet 106 may be made of continuous layers of plastic film extending from the distal edge of one arm-securing flap 84 to the distal edge of the other arm-securing flap 84. This construction that uses continuous layers of shell material to create the outside shell of both arm-securing flaps 84 and the base sheet 106, may advantageously create a hermetically sealed space between the layers of shell material forming the base sheet 106, that can house and protect wires traversing from one arm-securing flap heater to the other arm-securing flap heater. This construction that uses extensions of the shell material covering the two arm-securing flaps 84 may allow for the manufacture of the shells of the two arm-securing flaps 84 and the base sheet 106 (e.g., sheet of film), with a single seal in an RF press. The continuous pieces of shell material reduce the chances for errors, failures, and leaks at the attachments between the two arm-securing flaps 84 and the base sheet 106.

In some embodiments, the base sheet 106 is movable along the length of the surgical table mattress 30 or underbody support 16, in order to optimally position the arm-securing flaps 84 for covering the arms of the patient in various patient positions. For example, in the lithotomy position with the legs up in stirrups 6, the patient is moved toward the foot end of the surgical table 4 and the arm-securing flaps 84 may be located substantially in the midsection of the surgical table 4. In the supine position, the patient is in the normal position on the surgical table 4 and the arm-securing flaps 84 may be located toward the head end of the surgical table 4. Depending on the position of the patient on the surgical table 4, the arm-securing flaps 84 can be easily adjusted along the length of the surgical table 4 to match up with the location of the patient's arms.

Figure 31:
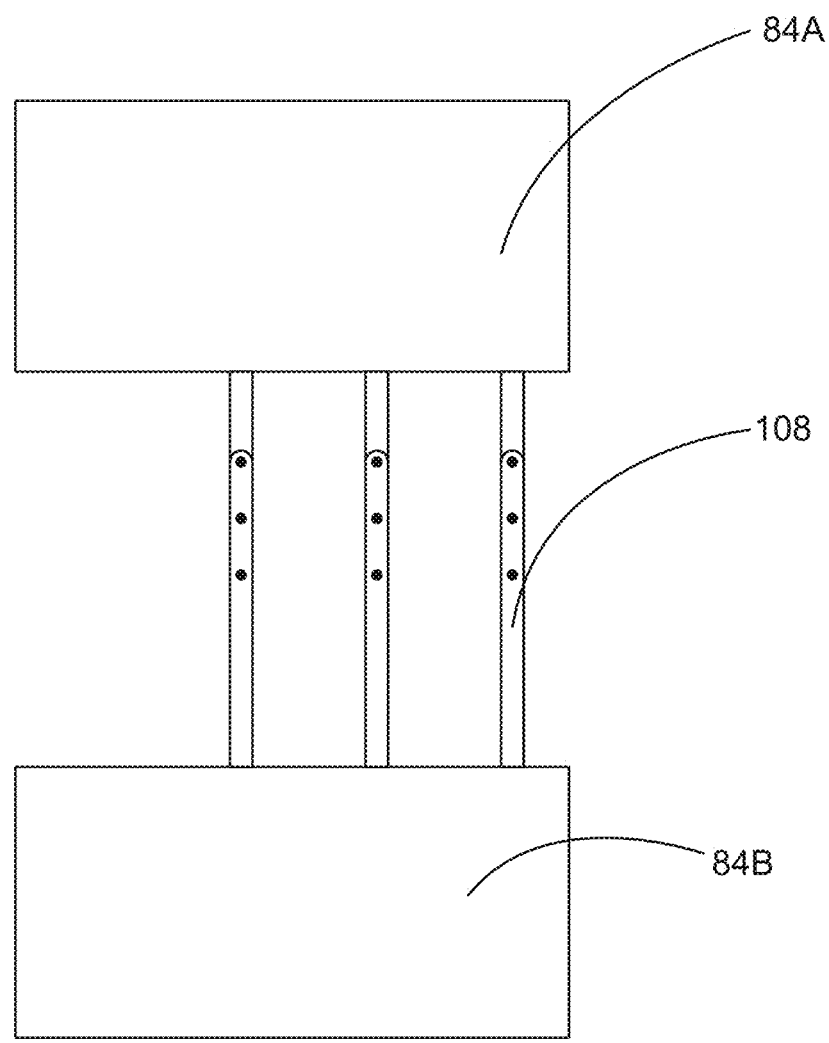
FIG. 31 is a top view of arm-securing flaps with base straps in accordance with illustrative embodiments.

In some embodiments, as shown in FIG. 31, the arm-securing flaps 84 may be secured to two or more base straps 108 that approximate the width of the surgical tabletop. The base straps 108 may be positioned under or over the surgical table mattress 30 or underbody support 16 and extend from one side to the other side of the surgical table. The length of the base straps 108 may be adjustable to accommodate patients of different widths. The arm-securing flaps 84 may be secured to each end of the base straps 108. In some embodiments, the base straps 108 may be incorporated into the base sheet 106 to allow for improved adjustability in width.

The purpose of the arm-securing flaps 84 is to provide security and safety to the tucked arms of the patient so as to prevent the arms from accidentally falling backward or downward and causing brachial plexus nerve injuries; protect the arms and fingers from pressure injuries due to pressure that may be accidentally applied by surgical equipment; protect exposed nerves such as the ulnar nerve at the elbow from applied pressure; and securely position and retain the arms at the sides of the patient. The arm-securing flaps 84 of the present disclosure are uniquely qualified to provide these protections.

Whether heated or not, the arm-securing flaps 84 of this disclosure may contain layers of padded material 96, such as fibrous thermal insulation or foam materials. In conjunction with the shell materials and the heater material, the layers of internal materials provide flexible padding that protects the arms and fingers of the patient from outside pressure points and accidental injury.

Figure 32:
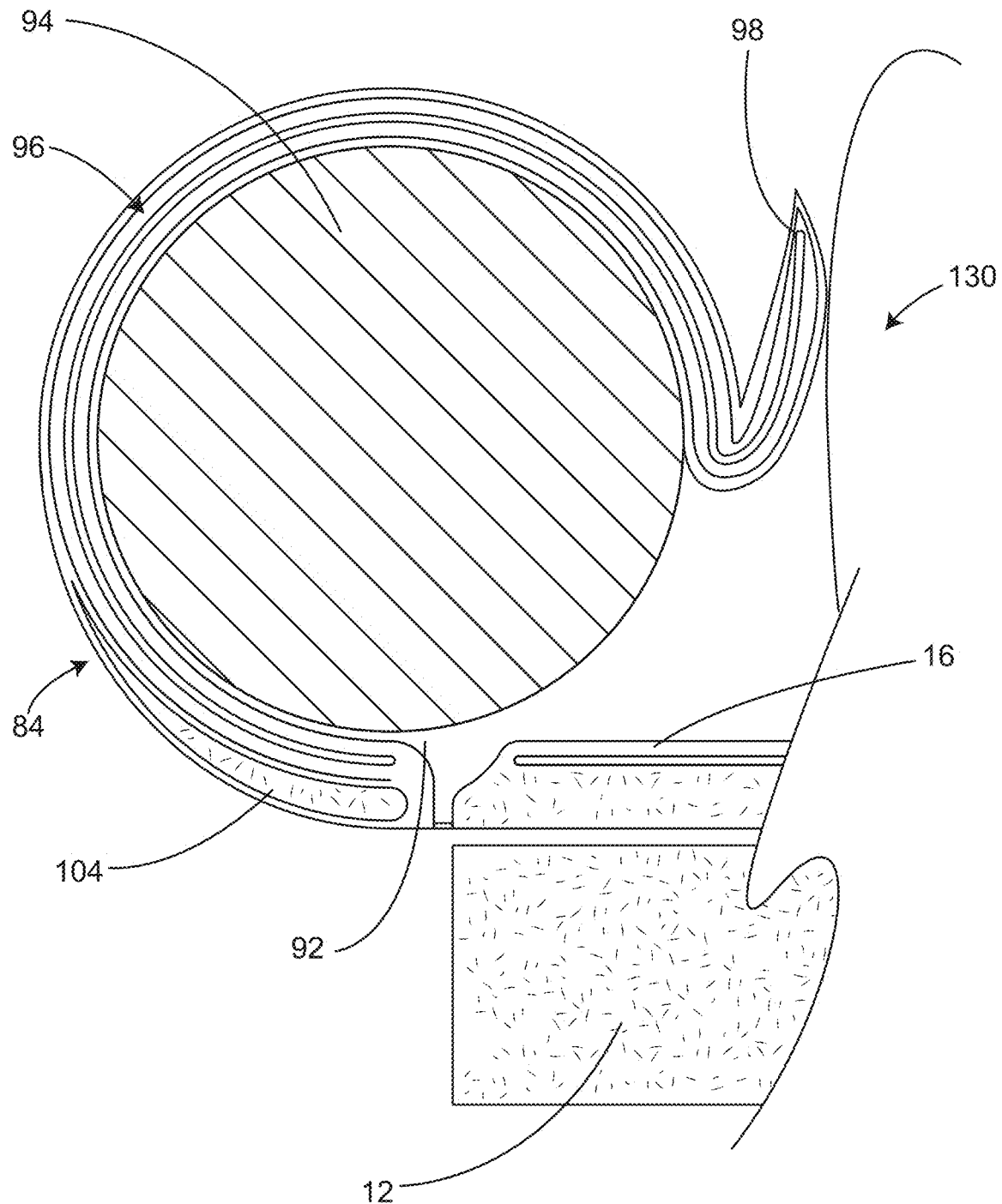
FIG. 32 is a cross-sectional view of an arm-securing flap wrapped around a patient's arm in accordance with illustrative embodiments.
Figure 33:
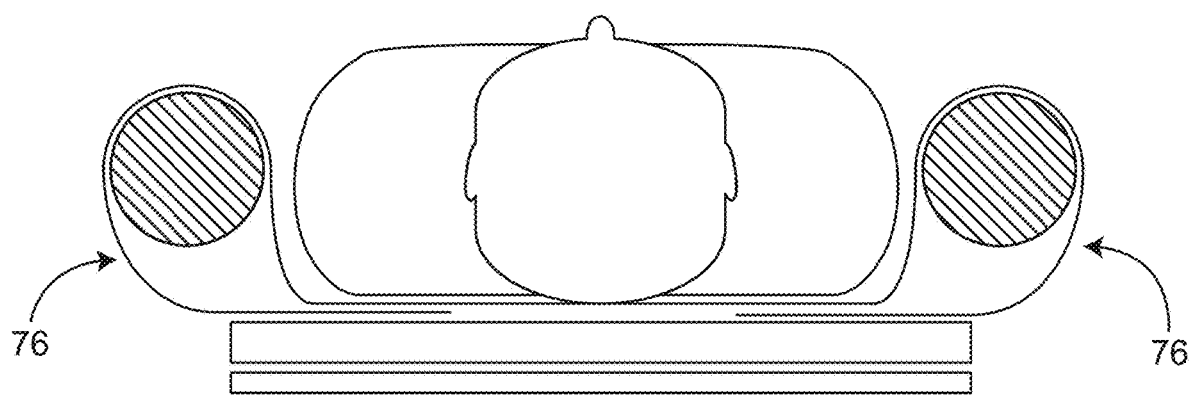
FIG. 33 is a cross-sectional view of a draw sheet wrapped around a patient's arms in accordance with illustrative embodiments.

In some embodiments, as shown in FIG. 32, the attachment of the arm-securing flap 84 to the edge of the underbody support 16 or base sheet 106, provides a shelf 92 on which the arm 94 of the patient 2 can rest (especially if the patient is obese and their arms are hanging over the edge of the surgical table). The shelf 92 is defined by the proximal side of the arm-securing flap 84 that is secured to the underbody support 16 or the base sheet 106. This shelf 92 is far more secure in supporting the weight of a heavy arm than the known arm tuck maneuver shown in FIG. 33. The known arm tuck relies entirely on the end of the draw sheet 76 not pulling out from under the patient and dropping the arm. The known arm tuck relies on the weight of the patient for retention but has no specific retention enhancing features. In contrast, the arm-securing flap 84 of the instant disclosure, as shown in FIG. 32, reliably secures the proximal side of the arm-securing flap 84 to the underbody support 16 or base sheet 106, rather than relying on the tucked end of a draw sheet 76 to stay securely tucked. The security provided by the positive connection between the arm-securing flaps 84 and the underbody support 16, is vastly more reliable than the security provided by tucking the ends of certain known draw sheets under the patient.

In some embodiments, a layer of foam 104, which can be a relatively stiff layer of foam, may be added inside the shell of the arm-securing flap 84, enhancing the shelf effect of the arm-securing flap 84. In some embodiments, the relatively stiff layer of foam 104 may be made of a closed cell polyethylene, closed cell polyurethane or closed cell PVC foam that is bendable in one direction (a simple curve) but resists bending in two directions (a compound curve). The relative security of the shelf 92 created by attaching the arm-securing flap 84 to the underbody support 16 obviates the need for metal toboggans or metal arm supports that need to be separately attached to the surgical table 4. The shelf 92 also automatically adjusts the width between the two arm supports, to fit the width of the patient. The arms of a large patient hanging over the side edges of the surgical table will be supported by the arm-securing flap 84 extending away from the sides of the underbody support 16 before wrapping upward around the arms. Wider patients with larger arms will automatically cause more of the arm-securing flap 84 to be included in the shelf 92. Conversely, thin patients with small arms may have their arms resting on the side edge of the underbody support 16 which becomes the shelf 92.

Figure 34:
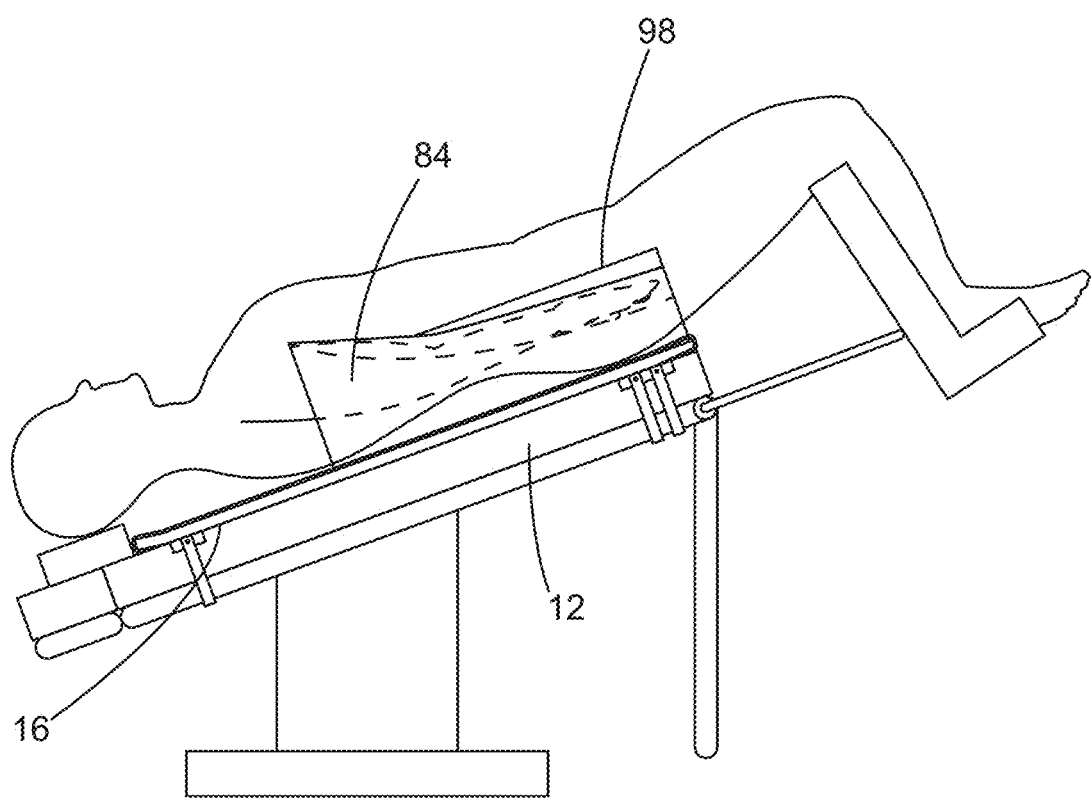
FIG. 34 is a side view of a patient laying on a surgical table and underbody support with arm-securing flaps in the lithotomy and Trendelenburg positions in accordance with illustrative embodiments.

In some embodiments, as shown in FIGS. 32 and 34, the arm-securing flap 84 is wrapped around the arm from the bottom upward toward the top of the arm and then tucked into the armpit and the space between the arm 94 and the torso 130. If the arm-securing flap 84 is too wide compared to the circumference of the arm, the distal edge 98 of the arm-securing flap 84 may be folded back on itself, leaving the folded back distal heated surface in contact with the side of the patients torso, advantageously increasing the heat transfer surface area. In some embodiments, folding the distal edge 98 of the arm-securing flap 84 back on itself allows a substantially rectangular-shaped flap with a substantially rectangular heater, to fit an upper arm that may have a large circumference and a forearm and wrist that has a relatively small circumference. The resulting folded back area will be greater at the wrist than the upper arm but the arm 94 will be uniformly surrounded by the arm-securing flap 84. The arm-securing flap 84, which can be rectangular in shape, wraps tightly around even a substantially cone-shaped arm by folding the excess heater near the hand (the point of the cone), back on itself and applying the folded back heater to the adjacent side of the torso for added heat transfer.

In some embodiments, when wrapped, the distal edge 98 of the arm-securing flap 84 at the wrist can be easily folded back on itself to reveal the hand and wrist for convenient inspection of the IV site.

Figure 35A:
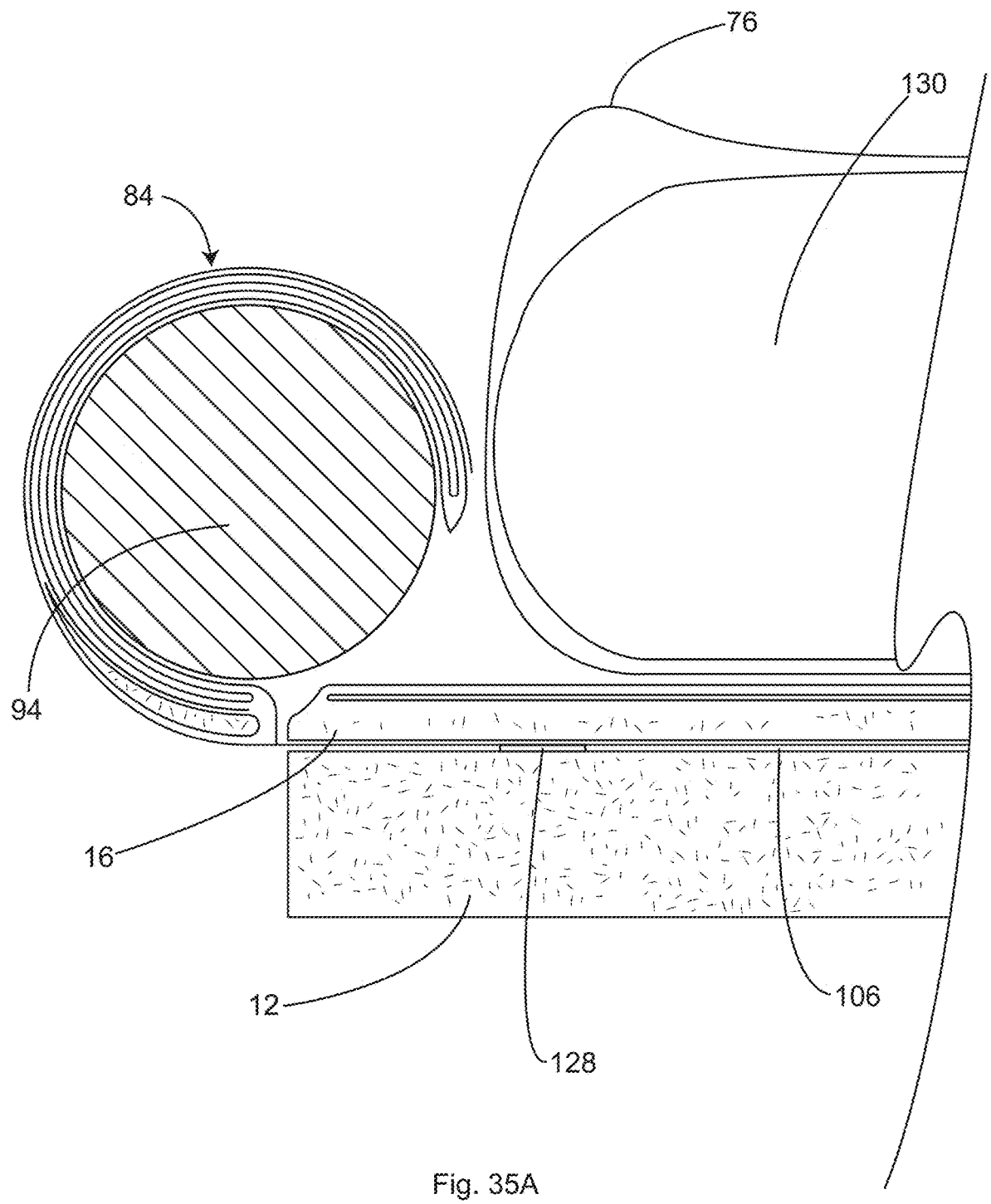
FIG. 35A is a cross-sectional view of an arm-securing flap wrapped around a patient's arm with a draw sheet in accordance with illustrative embodiments.
Figure 35B:
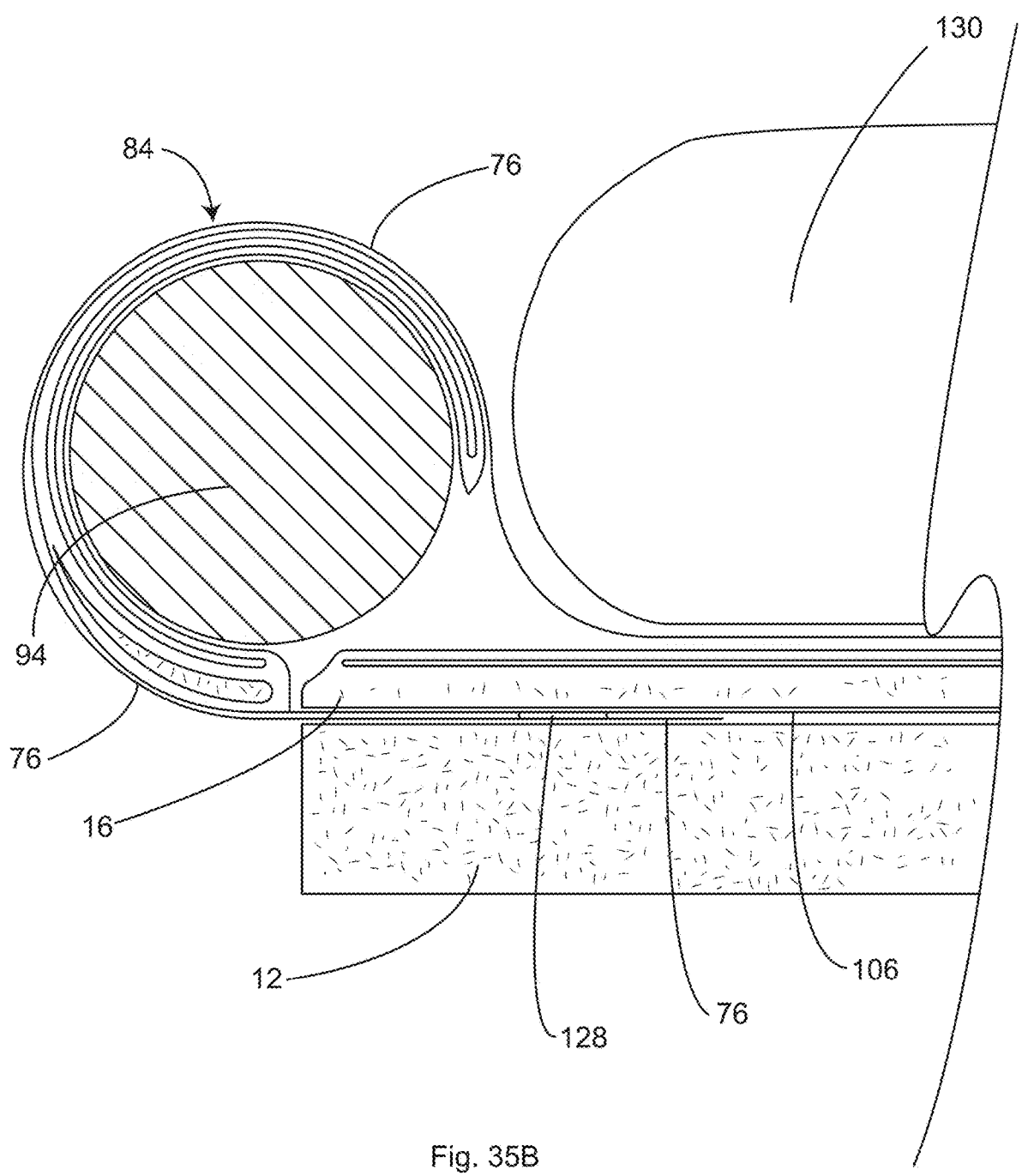
FIG. 35B is a cross-sectional view of an arm-securing flap wrapped around a patient's arm with a draw sheet in accordance with illustrative embodiments.

In some embodiments, as shown in FIGS. 35A and 35B, the draw sheet 76 may be wrapped in a conventional manner by first pulling it upward along side the torso 130 (between the arm 94 and the torso 130) and then wrapping it downward around the arm 94 from above and tucking it under the underbody support 16, surgical table mattress 30, or base sheet 106. The counter-rotational wrapping of the draw sheet 76 against the arm-securing flap 84 creates a unique and exceptionally secure arm wrap. The arm-securing flap 84 wraps from the bottom upward around the arm, and the draw sheet 76 wraps from the top downward around the arm. The arm-securing flap 84 and draw sheet 76 have their anchored edge on opposite sides of the arm and cross over each other, securing each other in place. The arm-securing flap 84 attached to underbody support 16 or base sheet 106 effectively neutralizes any forces from the patient's arm that could pull the tucked end of the draw sheet 76 out from its tucked position.

As shown in FIG. 35B, the counter-rotational wrapping of the draw sheet 76 against the arm-securing flap 84 prevents substantially all of the force that would naturally pull a conventionally tucked draw sheet out from under the patient. The force of an arm's weight that would normally pull a conventional draw sheet out from its tucked position under the patient, is totally prevented by the proximal side of the arm-securing flap 84 being attached to the underbody support 16 or base sheet 106. In some embodiments, the security of the arm wrap can be further increased if friction-enhancing elements 80 are added to the draw sheet 76 in the tucked areas that will contact the underbody support 16, surgical table mattress 30, or base sheet 106, to prevent accidental dislodgment of the draw sheet 76 when the draw sheet 76 is tucked as described above.

In some embodiments, friction-enhancing elements 80 may be added to the draw sheet 76 in areas that will contact the arm-securing flap 84, to further enhance the securing interaction of the counter-rotational wrapping of the draw sheet 76 against the arm-securing flap 84. In some embodiments, the hook portion 128 of a Velcro hook and loop fastener may be attached to the underbody support 16, surgical table mattress 30, or base sheet 106 to create a positive connection with the non-woven fabric of the draw sheet 76 which serves as the loop portion, making accidental dislodgment of the counter rotational connection between the draw sheet 76 and the arm-securing flap 84 nearly impossible. In some cases, the hook portions 128 are shown individually in the drawings as reference numerals 128A and 128B.

While the counter-rotational wrapping of the draw sheet 76 against the arm-securing flap 84 creates a unique and exceptionally secure wrap, it is also simple and intuitive to the user. Wrapping the arm-securing flap 84 from the bottom upward around the arm is intuitive and easily accomplished with two hands (in contrast to other conventional arm protection devices for the surgical patient that require three hands; one hand to hold the arm and two hands to wrap the device around the arm and secure it in place with straps). The arm-securing flap 84 hanging down from the side of the underbody support 16 effectively prevents the user from tucking the draw sheet first, prior to wrapping the arm in the arm-securing flap 84. Once the arm is wrapped with the arm-securing flap 84 from the bottom upward around the arm, the draw sheet 76 is wrapped from the top down and tucked under the underbody support 16, surgical table mattress 30, or base sheet 106 in a conventional draw sheet-tucking manner that the user is already familiar with.

In some embodiments, the three panel construction of an underbody support 16, surgical table mattress 30, or base sheet 106 with two arm-securing flaps 84 attached to the side edges of the underbody support 16 or surgical table mattress 30, as shown in FIG. 27, or to a base sheet 106 as shown in FIG. 29, or to base straps 108 as shown in FIG. 31, may be advantageous for a number of reasons compared to a single section with a single heater construction. For example, the maximum safe temperature of an underbody support that is a heated underbody support is 39° C., whereas the maximum safe temperature of an arm-securing wrap that is a heated arm-securing wrap is 43° C. Having a three panel construction allows each section to be temperature controlled independently and safely. The optimal construction of an underbody support 16 or surgical table mattress 30 includes a foam pad that may be compressible but is not particularly flexible. In contrast, the optimal construction of the arm-securing flaps 84 includes a thin fibrous thermal insulation layer that is not compressible but is very flexible for optimal wrapping and skin contact. The underbody support 16 or surgical table mattress 30 can be a fixed and predictable width that corresponds to the width of the surgical table 4. In contrast, the width of the arm-securing flaps 84 may advantageously be narrow for thinner patients and wider for bariatric patients. Arm-securing flaps 84 can be detachable or attached to a base sheet 106 and allow adjustment for varying patient widths and needs such as bariatric surgery.

Figure 36:
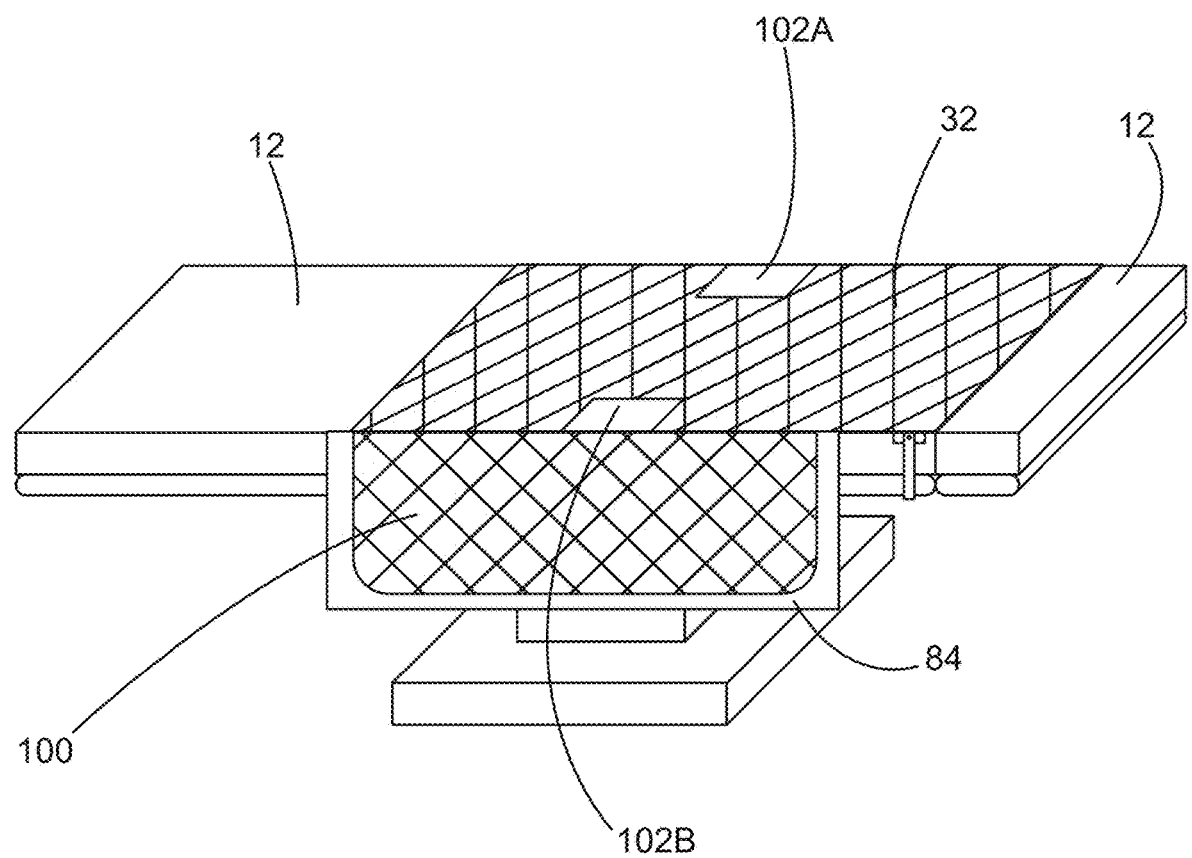
FIG. 36 is a perspective view of an underbody support with arm-securing flaps attached to a surgical table in accordance with illustrative embodiments.

In some embodiments, as shown in FIG. 36, a lateral extension 100 of the sheet of fabric 32 may extend outward to substantially cover the arm-securing flaps 84. The lateral extension 100 may approximate the size of the arm-securing flap 84. In some embodiments, the lateral extension 100 may be made of the same material as the sheet of fabric 32, including friction-enhancing elements and in some embodiments including holes or spaces in the lateral extension 100. In some embodiments, the lateral extension 100 may be made of a different material than the sheet of fabric 32, for example a woven or non-woven fabric that merely protects the skin of the patient's arm from directly contacting the heated arm-securing flap 84. In some embodiments, the lateral extension 100 may be made of a non-woven fabric that has been laminated to a layer of polymeric film. The non-woven fabric may be made of polyester fibers, for example, but other materials for the non-woven fabric are anticipated. The layer of polymeric film of the lateral extension 100 may be made of polyethylene or polypropylene, for example, but other film materials are anticipated and can be used. In some embodiments, the lateral extension 100 may be made of spunbond non-woven polypropylene fibers of approximately 1.0-1.4 oz/sqyd, extrusion coated on one side with a polypropylene film of 0.7-2.0 mill (0.0007-0.002 inches) thick. In some embodiments, when the lateral extension 100 is made of a different material than the sheet of fabric 32, the lateral extension 100 may be attached to the sheet of fabric 32 by an adhesive bond, a heat bond, an RF bond, or sewing.

In some embodiments, foam pads 102 may advantageously be attached to the lateral extension 100 where the elbows of the patient 2 are anticipated to be located. The foam pads 102 help to prevent pressure from being applied to the ulnar nerve at the elbow as it is resting on the shelf 92 created by the arm-securing flaps 84. The foam pads 102 may be made of visco-elastic "memory" foam for optimal padding of the elbow and arm. In some embodiments, the foam pads 102 may be between about 0.05-1.0 inches thick, about 4-8 inches wide, and about 6-16 inches long. In some cases, the foam pads 102 are shown individually in the drawings as reference numerals 102A and 102B.

In some embodiments, a method of supporting, protecting, and heating the arms of a patient 2 on a surgical table 4 is provided. The method includes (i) providing an underbody support 16 configured to support the patient 2 on the surgical table 4, the underbody support 16 including a compressible material layer having an upper surface configured to face the patient 2 opposite a base layer having a lower surface configured to face the surgical table 4; (ii) coupling the underbody support 16 to the surgical table 4; (iii) attaching arm-securing flaps 84 that comprise heated arm-securing flaps to the lateral side edges of the underbody support 16 or base sheet 106; (iv) placing a sheet of fabric 32 between the upper surface of the underbody support 16 and the patient 2, the sheet of fabric 32 comprising friction-enhancing elements 34 on one or both sides of the sheet of fabric 32, wherein the sheet of fabric 32 is configured to grip both the underbody support 16 and the patient 2 to prevent the patient from inadvertently slipping off the underbody support 16, and wherein the sheet of fabric 32 further includes lateral extensions 100 that substantially cover the arm-securing flaps 84; (v) positioning the patient 2 on the underbody support 16; (vi) pulling the draw sheet 76 upward alongside the torso; (vii) wrapping each arm-securing flap 84 comprising a heated arm-securing flap and its corresponding lateral extension 100 around a respective arm from the bottom upward; (viii) and then wrapping the ends of the draw sheet 76 downward around the arm from above and tucking it under the underbody support 16, surgical table mattress 30, or base sheet 106.

Figure 37:
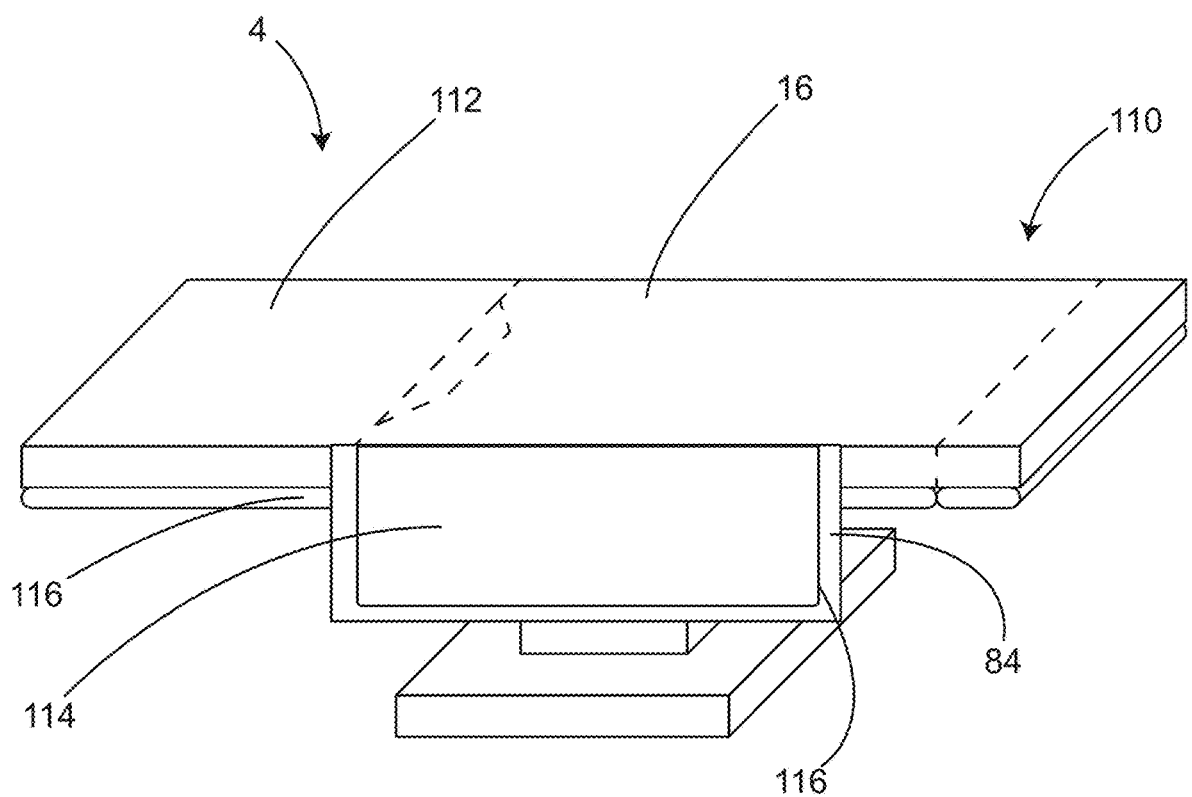
FIG. 37 is a perspective view of an underbody support with arm-securing flaps and a surgical table cover attached to a surgical table in accordance with illustrative embodiments.

In some embodiments, as shown in FIG. 37, an underbody support 16, which may be heated, is configured to support the patient 2 (not shown) on the surgical table 4 with arm-securing flaps 84 (which may also be heated) and may advantageously be used for surgical procedures that are not performed in the Trendelenburg position. For example, cardiac surgery generally requires that the patients arms are tucked at their sides and with the entire frontal surface of the patient "prepped," there is little available surface area for active surface warming. Similarly, robotic surgery of the abdomen or chest may require the arms to be tucked in order to provide adequate room for the robot to be next to the patient. Other surgical procedures are also anticipated. Warming the patient's back and arms as well as supporting and protecting the patient's arms, may be very desirable. If the patient is not going to be placed in the steep Trendelenburg position, the sheet of fabric 32 with friction-enhancing elements 34 may not be required. In this situation, the sheet of fabric 32 positioned over the underbody support 16 or surgical table mattress 30, may be replaced by a surgical table cover 110 that is modified to provide lateral extensions or barrier flaps 114 that cover the arm-securing flaps 84.

In some embodiments, the surgical table cover 110 is a piece of woven or non-woven polymeric or natural fiber fabric, sized to cover the entire top of the surgical table mattress 112, and have enough extra material to tuck the edges of the surgical table cover 110 under the surgical table mattress 112. In some embodiments, the surgical table cover 110 may be sized to have about 12-18 inches of extra material on some or all sides of the surgical table mattress 112 for tucking. In some embodiments, the surgical table cover 110 is a piece of woven or non-woven polymeric or natural fiber fabric that is laminated to a layer of plastic film to create a waterproof protector of the surgical tabletop. In some embodiments, the surgical table cover 110 may be made of spunbond non-woven polypropylene fibers of approximately 1.0-1.4 oz/sqyd, extrusion coated on one side with a polypropylene film of 0.7-2.0 mill (0.0007-0.002 inches) thick. In some embodiments, the surgical table cover 110 is made of non-woven fibers made of polyester, polyethylene, polypropylene or rayon. In some embodiments, the surgical table cover 110 is made of spunlace polymeric fibers (for example, Sontara, Jacob Holm Corp.). In some embodiments, the surgical table cover 110 is made of woven cotton or woven polymeric fibers. In some embodiments, the surgical table cover 110 may include cellulose filler materials. In some embodiments, the surgical table cover 110 may include other fluid absorbing materials.

In some embodiments, the surgical table cover 110 has two slits 116 on each side extending about 12-18 inches inward from the side edges of the surgical table cover 110. The slits 116 create two barrier flaps 114 that may correspond with the location of the arm-securing flaps 84. The innermost points of the slits 116, correspond roughly with the width of the surgical table mattress 112. When the edges of the surgical table cover 110 have been tucked under the surgical table mattress 112, the two barrier flaps 114 may be left un-tucked and covering the arm-securing flaps 84. This may be especially convenient because the arm-securing flaps 84 would prevent tucking of the surgical table cover 110 at that location. In some embodiments, the two barrier flaps 114 covering the arm-securing flaps 84, protect the patient's arms from residual cleaning fluids that may be on the arm-securing flaps 84.

In some embodiments, as shown in FIGS. 35A and 35B, if the patient is not going to be placed in the steep Trendelenburg position, the draw sheet 76 previously disclosed may not include friction-enhancing elements 80 on the upper surface of the draw sheet 76 in contact with the patient's back. In some embodiments, the draw sheet 76 for surgical procedures on a flat table may still include friction-enhancing elements 80 in the areas not under the patient's back, to aid in the security of the counter-rotating engagement with the arm-securing flaps 84 and with the security of the tucked ends of the draw sheet 76 as previously described. In some embodiments, the friction-enhancing elements 80 near the ends of the draw sheet 76 may be foam plastic or rubber three-dimensional elements applied directly to the draw sheet 76. In some embodiments, the friction-enhancing elements 80 near the ends of the draw sheet 76 may be pieces of the sheet of fabric 32 material bonded to the draw sheet 76 with an adhesive, RF, heat or sewing bond.

In some embodiments, the hook portion of a Velcro hook and loop fastener may be attached to the underbody support 16, surgical table mattress 12, or base sheet 106 to create a positive connection with the non-woven fabric of the draw sheet 76 which serves as the loop portion, making accidental dislodgment of the counter rotational connection between the draw sheet 76 and the arm-securing flap 84 nearly impossible. Making the draw sheet 76 out of non-woven fabric conveniently allows the hook portion of a Velcro hook and loop fastener to adhere anywhere along its length.

Figure 38:
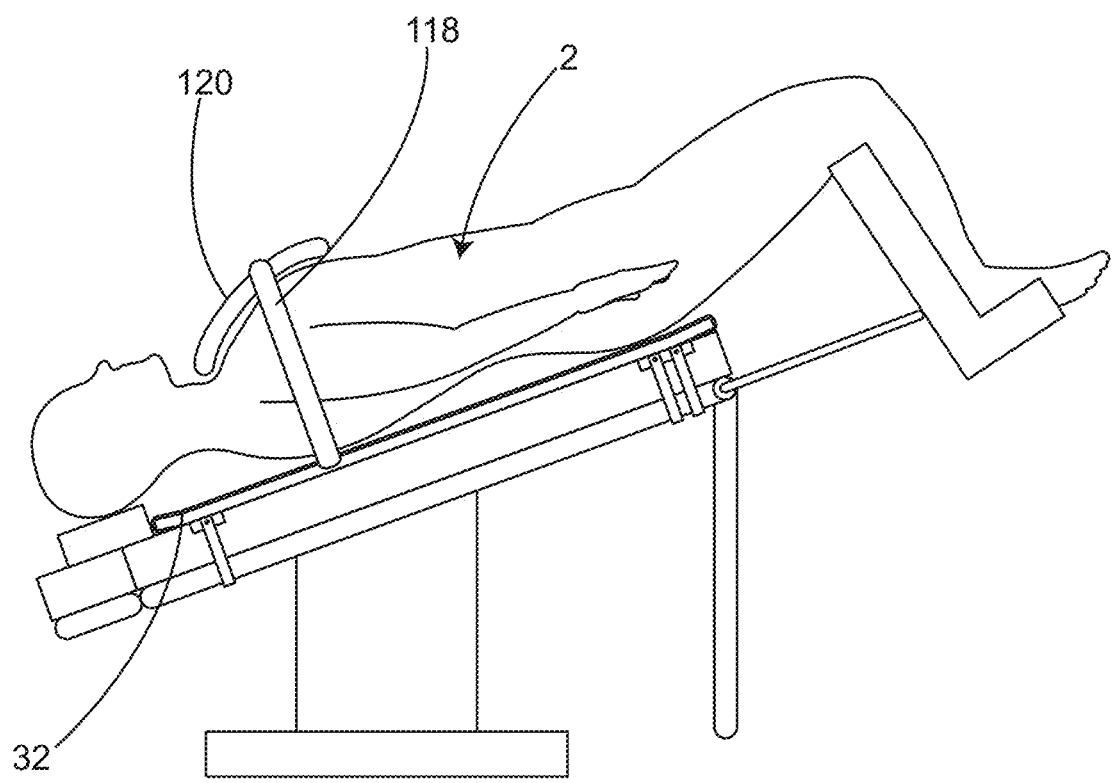
FIG. 38 is a side view of a patient laying on a surgical table and underbody support with chest straps securing a heated blanket in the lithotomy and Trendelenburg positions in accordance with illustrative embodiments.

In some embodiments, as shown in FIG. 38, two chest straps 118 may be attached to the side edges of the sheet of fabric 32, or the two chest straps 118 may be the exposed ends of a single strap extending from one side to another side of the surgical table 4 under the sheet of fabric 32. The chest straps 118 from each side can be crossed over a chest of the patient 2 and the free ends of the chest straps 118 can be secured together with Velcro or other fasteners. These chest straps 118 may be positioned to secure a heated blanket 120 over the chest of the patient 2. In some embodiments, the chest straps 118 may be made of a non-woven fibrous material that can serve as the loop side of a hook and loop (Velcro) fastener. A piece of Velcro hook material may be attached to one or both of the chest straps 118, that can engage securely anywhere along the length of the other (e.g., non-woven) chest strap 118.

As shown in FIG. 38, the two chest straps 118 may be attached to the side edges of the sheet of fabric 32. These straps 118 may replace straps that would otherwise be attached to the side rails 20 of the surgical table 4 by the nurse in the operating room. Pre-attaching these straps 118 to the sheet of fabric 32 is convenient and saves nursing time. In some embodiments, since the straps 118 are only intended to secure a heated blanket 120 over the patient's chest, they are thus relatively narrow (0.5-1.25 inches wide). The narrow straps may only be capable of securing a light object such as a heated blanket 120. Advantageously, narrow straps 118 cannot be mistaken for a safety strap meant to secure the patient to the surgical table.

Typically the patient is anesthetized with general anesthesia while their head is near the head end of the surgical table 4, to provide the anesthetist easy access to the head and airway for intubation. After the induction of anesthesia, the patient must be moved toward the foot end of the surgical table 4 for positioning in the lithotomy position. Typically, this move is accomplished by lifting the patient off of the underbody support 16 by lifting each side of the draw sheet 76 while also lifting the patient's head, shoulders, and feet. Operating room staff has suffered many back injuries lifting heavy patients. Heavy patients are very difficult to lift and therefore the movement may end up being more of a sliding movement rather than a lifting movement. The problem with sliding the patient is that sheet of fabric 32 with friction-enhancing elements 34 as well as other foam securement pads 26 are designed to prevent this sliding motion and therefore makes repositioning of the patient quite difficult.

Figure 39:
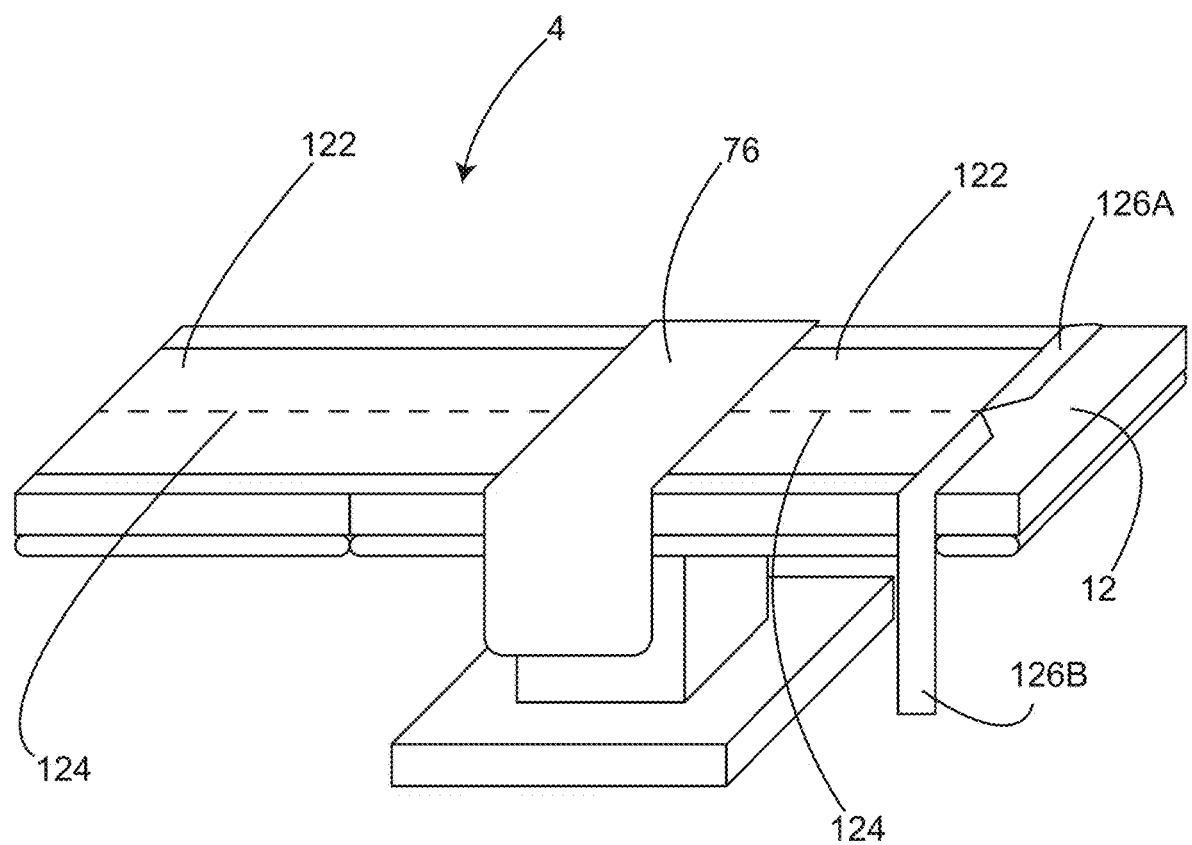
FIG. 39 is a perspective view of a surgical table with a slide sheet and draw sheet in accordance with illustrative embodiments.

In some embodiments, as shown in FIG. 39, a slide sheet 122 may be positioned over the top of the sheet of fabric 32 or other foam securement pad 26 to allow easy sliding of the patient toward the foot end of the surgical table 4. The draw sheet 76 may be placed over the top of the slide sheet 122 in order to facilitate sliding the patient toward the foot end of the surgical table 4. Both the patient and the fabric side of the draw sheet 76 easily slide against the slippery surface of the slide sheet 122 without having to be lifted, separated from the sheet of fabric 32 and the friction-enhancing elements 34. The slide sheet 122 may be made of plastic film, non-woven fabric, woven fabric, or non-woven fabric laminated to plastic film. The plastic film may be polyethylene, polypropylene or other suitable plastics. The non-woven or woven fabrics may be made of polyester or polypropylene fibers or other suitable plastic or natural fibers. In some embodiments, the nonwoven fibrous side of the slide sheet 122 is placed upward to maximize the slippery qualities of the slide sheet 122 and to be optimally comfortable for the patient to lay on. In some embodiments, the ends of the slide sheet 122 may tuck under the head and foot ends of the underbody support 16 or surgical table mattress section 12 supporting the patient's torso to help prevent the slide sheet 122 from sliding during movement of the patient 2. In some embodiments, the ends of the slide sheet 122 may tuck under the head and/or foot ends of the surgical table mattress 30 to help prevent the slide sheet 122 from sliding during movement of the patient 2.

In some embodiments, the foot end of slide sheet 122 may be used to facilitate repositioning a patient 2 from the position of sitting sideways on the surgical table 4 (e.g., for a spinal block), to laying longitudinally on the surgical table 4. This repositioning maneuver requires the patient to be rotated 90° while sitting, before being laid on their back. Rotating the sitting patient in this manner would be prevented by the friction-enhancing elements 34 of the sheet of fabric 32 and the draw sheet 76 or other foam securement pads 26. However, if the patient is sitting on the slide sheet 122, rotating the patient 90° is easy to do and the sheet of fabric 32 or the draw sheet 76 or other foam securement pads 26 are not displaced in the process.

Once the patient has been repositioned, the slide sheet 122 must be removed from under the patient 2 or the entire purpose of the friction-enhancing elements 34 of the securement device or other foam securement pads 26 will be negated. In some embodiments, as shown in FIG. 39, the slide sheet 122 may have a perforation line 124 running longitudinally substantially in the middle of the slide sheet 122 from end to end. The perforation line 124 allows the two sides of the slide sheet 122 to be separated from each other so that each side can be pulled out from under the patient independently. Each side of slide sheet 122 may advantageously be pulled out from under that side of the patient 2 without having to cross the midline. In some embodiments, a pull-tab 126 may be attached to each side of the slide sheet 122, near the perforation line 124, at either the head or foot end. In some embodiments, the pull-tab 126 may be positioned so that the pulling force is directed laterally in order to pull one half of the slide sheet 122 out from under the patient at a time, starting at the head end, for example, and ending at the foot end. In some embodiments, the pull-tab 126 may be positioned so that the pulling force slides the loose end of the slide sheet 122 over the top of the remaining slide sheet 122, separated from the friction-enhancing elements 34 by the remaining slide sheet 122, for easiest removal of the slide sheet 122 from under the patient 2. In some embodiments, the pull-tab 126 may be a bright color, such as red or yellow, in order to remind the anesthetist to remove the slide sheet 122 from under the patient before putting the patient into the Trendelenburg position. In some cases, the pull-tabs 126 are shown individually in the drawings as reference numerals 126A and 126B. The pull-tabs 126 may be extensions of the slide sheet 122 material or may be added material attached to the slide sheet 122 near the perforation line 124.

Whereas particular embodiments of the invention have been described for the purposes of illustration, it will be evident to those skilled in the art that numerous variations of the details may be made without departing from the invention as set forth in the embodiments described herein.

The invention claimed is:

1. A patient securing overlay with securement to a surgical table mattress or underbody support for use during surgery in the Trendelenburg position, comprising:
   a sheet of fabric configured to support a patient's torso on a surgical table;
   the sheet of fabric having an upper surface configured to face the patient and a lower surface configured to face the surgical table mattress or underbody support;
   the sheet of fabric includes friction enhancing elements applied to at least a portion of the upper surface;
   at least some of the friction enhancing elements include a layer of foam material that is adhesively laminated to at least a portion of the upper surface of the sheet of fabric;
   the sheet of fabric includes an extension at a foot end of the sheet of fabric that provides material to be tucked under a foot end of the surgical table mattress or underbody support for securing the foot end of the sheet of fabric to the surgical table mattress or underbody support; and
   the extension at the foot end of the sheet of fabric includes one or more friction enhancing elements that improve the friction bond between the sheet of fabric and a top of either the surgical table or the surgical table mattress;
   wherein the extension at the foot end of the sheet of fabric is narrower than the sheet of fabric; and
   the extension at the foot end includes an anchor that comprises a planar sheet of material that comprises plastic, metal or fiberboard;
   wherein the anchor is removably insertable between a bottom of the surgical table mattress and the top of the surgical table or between a bottom of the underbody support and the top of the surgical table mattress and anchors against a perineal cutout in the surgical table mattress or the underbody support such that the extension stretches to create a force vector that is directly opposite a force vector associated with the patient sliding down an incline of the surgical table when the surgical table is in the Trendelenburg position.

2. The patient securing overlay of claim 1, wherein the one or more friction enhancing elements that that improve the friction bond between the sheet of fabric and a top of either the surgical table or the surgical table mattress include an adhesive applied to the sheet of fabric.

3. The patient securing overlay of claim 1, wherein the one or more friction enhancing elements that improve the friction bond between the sheet of fabric and a top of either the surgical table or the surgical table mattress include an adhesive applied to the friction enhancing elements.

4. The patient securing overlay of claim 1, wherein the one or more friction enhancing elements that improve the friction bond between the sheet of fabric and a top of either the surgical table or the surgical table mattress include three dimensional plastic or rubber friction enhancing elements.

5. The patient securing overlay of claim 1, wherein the friction enhancing elements comprise PVC foams, silicone, viscoelastic polyurethane foams, viscoelastic polymeric foams, urethane foams, PVC, polymers or rubbers.

6. The patient securing overlay of claim 5, wherein the friction enhancing elements are open cell foams.

7. The patient securing overlay of claim 6, wherein the surgical table mattress or underbody support is heated and the heat is transferred from the heated surgical table mattress or underbody support to the patient through the open cells of the foam layer.

8. The patient securing overlay of claim 1, wherein the extension at the foot end of the sheet of fabric includes a pouch formed near a distal edge of the extension and the pouch is sized to accommodate the anchor.

9. The patient securing overlay of claim 1, wherein the extension at the foot end of the sheet of fabric is attached to the anchor by adhesive bonding, sewing, thermal welding, RF welding, rivets, staples, or Velcro.

10. A patient securing overlay with securement to a surgical table mattress or underbody support for use during surgery in the Trendelenburg position, comprising:
a sheet of fabric configured to support a patient's torso on a surgical table;
the sheet of fabric having an upper surface configured to face the patient and a lower surface configured to face the surgical table mattress or underbody support;
the sheet of fabric includes friction enhancing elements applied to at least a portion of the upper surface;
at least some of the friction enhancing elements include a layer of foam material that is adhesively laminated to at least a portion of the upper surface of the sheet of fabric;
the sheet of fabric includes an extension at a foot end of the sheet of fabric that provides material to be tucked under a foot end of the surgical table mattress or underbody support for securing the foot end of the sheet of fabric to the surgical table mattress or underbody support; and
the extension at the foot end of the sheet of fabric includes one or more friction enhancing elements that improve the friction bond between the sheet of fabric and a top of either the surgical table or the surgical table mattress;
wherein the extension at the foot end of the sheet of fabric is narrower than the sheet of fabric; and
the extension of the sheet of fabric at the foot end of the sheet of fabric anchors against a perineal cutout in the surgical table mattress or the underbody support such that the extension stretches to create a force vector that is directly opposite a force vector associated with the patient sliding down an incline of the surgical table when the surgical table is in the Trendelenburg position.

11. The patient securing overlay of claim 10, wherein the one or more friction enhancing elements that improve the friction bond between the sheet of fabric and a top of either the surgical table or the surgical table mattress include an adhesive applied to the sheet of fabric.

12. The patient securing overlay of claim 10, wherein the one or more friction enhancing elements that improve the friction bond between the sheet of fabric and a top of either the surgical table or the surgical table mattress include an adhesive applied to the friction enhancing elements.

13. The patient securing overlay of claim 10, wherein the one or more friction enhancing elements that improve the friction bond between the sheet of fabric and a top of either the surgical table or the surgical table mattress include three dimensional plastic or rubber friction enhancing elements.

14. The patient securing overlay of claim 10, wherein the friction enhancing elements comprise PVC foams, silicone, viscoelastic polyurethane foams, viscoelastic polymeric foams, urethane foams, PVC, polymers or rubbers.

15. The patient securing overlay of claim 14, wherein the friction enhancing elements are open cell foams.

16. The patient securing overlay of claim 15, wherein the surgical table mattress or underbody support is heated and the heat is transferred from the heated surgical table mattress or underbody support to the patient through the open cells of the foam layer.

17. A patient securing overlay with securement to a surgical table mattress or underbody support for use during surgery in the Trendelenburg position, comprising:
a sheet of fabric configured to support a patient's torso on a surgical table;
the sheet of fabric having an upper surface configured to face the patient and a lower surface configured to face the surgical table mattress or underbody support;
the sheet of fabric includes friction enhancing elements applied to at least a portion of the upper surface;
at least some of the friction enhancing elements include a layer of foam material that is adhesively laminated to at least a portion of the upper surface of the sheet of fabric;
the sheet of fabric includes an extension at a foot end of the sheet of fabric that provides material to be tucked under a foot end of the surgical table mattress or underbody support for securing the foot end of the sheet of fabric to the surgical table mattress or underbody support; and
the extension at the foot end of the sheet of fabric includes one or more friction enhancing elements that improve the friction bond between the sheet of fabric and a top of either the surgical table or the surgical table mattress;
wherein the extension of the sheet of fabric at the foot end of the sheet of fabric anchors to the foot end of the surgical table mattress or the underbody support such that the extension stretches to create a force vector that is directly opposite a force vector associated with the patient sliding down an incline of the surgical table when the surgical table is in the Trendelenburg position.

18. The patient securing overlay of claim 17, wherein the one or more friction enhancing elements that improve the friction bond between the sheet of fabric and a top of either the surgical table or the surgical table mattress include an adhesive applied to the sheet of fabric.

19. The patient securing overlay of claim 17, wherein the one or more friction enhancing elements that improve the friction bond between the sheet of fabric and a top of either the surgical table or the surgical table mattress include an adhesive applied to the friction enhancing elements.

20. The patient securing overlay of claim 17, wherein the one or more friction enhancing elements that improve the friction bond between the sheet of fabric and a top of either the surgical table or the surgical table mattress include three dimensional plastic or rubber friction enhancing elements.

21. The patient securing overlay of claim 17, wherein the friction enhancing elements comprise PVC foams, silicone, viscoelastic polyurethane foams, viscoelastic polymeric foams, urethane foams, PVC, polymers or rubbers.

22. The patient securing overlay of claim 21, wherein the friction enhancing elements are open cell foams.

23. The patient securing overlay of claim 22, wherein the surgical table mattress or underbody support is heated and the heat is transferred from the heated surgical table mattress or underbody support to the patient through the open cells of the foam layer.

\* \* \* \* \*